US012618117B2

(12) United States Patent
Nam et al.

(10) Patent No.: US 12,618,117 B2
(45) Date of Patent: May 5, 2026

(54) COMPOSITION FOR DISCRIMINATING LACTOBACILLUS ACIDOPHILUS STRAINS AND DISCRIMINATION METHOD USING SAME

(71) Applicant: KOREA FOOD RESEARCH INSTITUTE, Jeollabuk-do (KR)

(72) Inventors: Young-do Nam, Jeollabuk-do (KR); Won-Hyong Chung, Daejeon (KR); Mi Young Lim, Seoul (KR); So-Young Lee, Jeollabuk-do (KR); Yong-Soo Park, Seoul (KR); Jisu Kang, Gwangju (KR); Yun-Tai Kim, Jeollabuk-do (KR); Hee Soon Shin, Jeollabuk-do (KR); Ji-hee Shin, Jeollabuk-do (KR); Seungpyo Hong, Jeollabuk-do (KR)

(73) Assignee: KOREA FOOD RESEARCH INSTITUTE, Jeollabuk-do (KR)

( * ) Notice: Subject to any disclaimer, the term of this patent is extended or adjusted under 35 U.S.C. 154(b) by 1342 days.

(21) Appl. No.: 17/278,472

(22) PCT Filed: May 29, 2019

(86) PCT No.: PCT/KR2019/006460
§ 371 (c)(1),
(2) Date: Jan. 26, 2022

(87) PCT Pub. No.: WO2020/060003
PCT Pub. Date: Mar. 26, 2020

(65) Prior Publication Data
US 2022/0154250 A1 May 19, 2022

(30) Foreign Application Priority Data

| | | |
|---|---|---|
| Sep. 21, 2018 | (KR) | 10-2018-0113928 |
| Apr. 8, 2019 | (KR) | 10-2019-0040985 |
| Apr. 8, 2019 | (KR) | 10-2019-0040986 |

(51) Int. Cl.
*C12Q 1/68* (2018.01)
*C12Q 1/689* (2018.01)

(52) U.S. Cl.
CPC .................................... *C12Q 1/689* (2013.01)

(58) Field of Classification Search
CPC ....................................................... C12Q 1/68
See application file for complete search history.

(56) References Cited

U.S. PATENT DOCUMENTS

| | | | | |
|---|---|---|---|---|
| 7,919,277 B2 * | 4/2011 | Russell | ................... | C12Q 1/689 |
| | | | | 435/6.15 |
| 8,361,725 B2 * | 1/2013 | Russell | ................... | C12Q 1/689 |
| | | | | 435/6.12 |
| 2003/0050470 A1 * | 3/2003 | An | ........................ | C07H 21/00 |
| | | | | 435/6.14 |
| 2004/0023207 A1 * | 2/2004 | Polansky | ............. | A61K 48/005 |
| | | | | 435/456 |
| 2006/0199190 A1 * | 9/2006 | Russell | ................... | C12Q 1/689 |
| | | | | 435/6.15 |
| 2014/0127695 A1 * | 5/2014 | Drake | ................... | C12Q 1/6816 |
| | | | | 435/6.12 |
| 2015/0167092 A1 * | 6/2015 | Kartalov | .............. | C12Q 1/6883 |
| | | | | 506/4 |
| 2022/0154250 A1 * | 5/2022 | Nam | ....................... | C12Q 1/689 |

FOREIGN PATENT DOCUMENTS

| | | | | | |
|---|---|---|---|---|---|
| CN | 106319083 | | 1/2017 | | |
| CN | 108588245 | A * | 9/2018 | | |
| KR | 10-0775641 | | 11/2007 | | |
| KR | 10-1193410 | | 10/2012 | | |
| KR | 10-2018-0018422 | | 2/2018 | | |
| KR | 20190063376 | A * | 6/2019 | ............. | C12Q 1/689 |
| WO | WO-2020060003 | A1 * | 3/2020 | ............. | C12Q 1/689 |

OTHER PUBLICATIONS

CN10855245A_Description , english translation of CN108588245A published Sep. 28, 2018. (Year: 2018).*
Genbank Accession No. AF429668—*Lactobacillus acidophilus* strain ATCC 521 60 kDa heat shock protein (HSP60) gene, partial cds, submitted Oct. 3, 2001, retrieved on Mar. 6, 2025, from http://www.ncbi.nlm.nih.gov/nuccore/AF429668). (Year: 2001).*
Genbank Accession No. CP017062—*Lactobacillus acidophilus* strain LA1, complete genome, submitted Aug. 26, 2016, retrieved on Mar. 6, 2025, from http://www.ncbi.nlm.nih.gov/nuccore/CP017062). (Year: 2016).*
Genbank Accession No. CP025200—*Lactobacillus acidophilus* strain YT1 chromosome, complete genome, submitted Dec. 7, 2017 , retrieved on Feb. 25, 2025, from http://www.ncbi.nlm.nih.gov/nuccore/CP025200). (Year: 2017).*
Herbel, S.R., Von Nickisch-Rosenegk, M., Kuhn, M., Murugaiyan, J., Wieler, L.H. and Guenther, S., 2014. Specific TaqMan probes for the identification and quantification of *Lactobacilli* in pharmaceuticals. J Prob Health, 2(115), pp. 1402-1410. (Year: 2014).*
Horvath et al., 2009. Comparative analysis of CRISPR loci in lactic acid bacteria genomes. International journal of food microbiology, 131(1), pp. 62-70. (Year: 2009).*
SantaLucia Jr, John. Physical principles and visual-OMP software for optimal PCR design. PCR Primer Design. Humana Press, 2007: pp. 3-33. (Year: 2007).*

(Continued)

*Primary Examiner* — Gary Benzion
*Assistant Examiner* — Olayinka A Oyeyemi
(74) *Attorney, Agent, or Firm* — DUANE MORRIS LLP; Gregory M. Lefkowitz; Brandon A. Chan

(57) ABSTRACT

The present disclosure relates to a composition for discriminating the species *Lactobacillus acidophilus*, which enables microorganisms belonging to the species *Lactobacillus acidophilus* to be discriminated, detected and identified simply, quickly and accurately from a target sample. Therefore, the present disclosure can be effectively used in the development of fermented milk, baby food, dairy products, livestock feed, cosmetics, health supplements, drugs for intestinal disorders, raw materials, etc. using the *Lactobacillus acidophilus* sp. strain.

10 Claims, 24 Drawing Sheets
Specification includes a Sequence Listing.

(56) References Cited

OTHER PUBLICATIONS

Singh, S., Goswami, P., Singh, R. and Heller, K.J., 2009. Application of molecular identification tools for *Lactobacillus*, with a focus on discrimination between closely related species: A review. LWT-Food Science and Technology, 42(2), pp. 448-457. (Year: 2009).*

You, I. and Kim, E.B., 2020. Genome-based species-specific primers for rapid identification of six species of *Lactobacillus acidophilus* group using multiplex PCR. PloS one, 15(3), e0230550, pp. 1-9. (Year: 2020).*

Yu et al., 2012. Phylogenetic study of *Lactobacillus acidophilus* group, *L. casei* group and *L. plantarum* group based on partial hsp 60, phe S and tuf gene sequences. European Food Research and Technology, 234, pp. 927-934. (Year: 2012).*

Genbank Accession No. CP000033.3—*Lactobacillus acidophilus* NCFM, complete genome, submitted Oct. 15, 2004, retrieved on Sep. 18, 2025, from http://www.ncbi.nlm.nih.gov/nuccore/CP000033). (Year: 2004).*

Genbank Accession No. CP005926.2—*Lactobacillus acidophilus* La-14, complete genome, submitted Apr. 12, 2013, retrieved on Sep. 18, 2025, from http://www.ncbi.nlm.nih.gov/nuccore/CP005926). (Year: 2013).*

Genbank Accession No. CP156988—*Lactobacillus acidophilus* strain NCFM chromosome, complete genome, submitted May 21, 2024, retrieved on Sep. 18, 2025, from http://www.ncbi.nlm.nih.gov/nuccore/CP156988). (Year: 2024).*

KR2019-0063376A—Description pub. Jun. 7, 2019, file Sep. 21, 2018. English Translation of KR2019-063376A. (Year: 2019).*

Sattler, V.A., Mohnl, M. and Klose, V., 2014. Development of a strain-specific real-time PCR assay for enumeration of a probiotic *Lactobacillus reuteri* in chicken feed and intestine. PLoS One, 9(2), e90208, pp. 1-7. (Year: 2014).*

Sheu et al., 2009. Development and use of tuf gene-based primers for the multiplex PCR detection of *Lactobacillus acidophilus*, *Lactobacillus casei* group, *Lactobacillus delbrueckii*, and Bifidobacterium longum in commercial dairy products. Journal of food protection, 72(1), pp. 93-100. (Year: 2009).*

Shin et al., 2022. Detection and identification of *Lactobacillus acidophilus* species and its commercial probiotic strains using CRISPR loci-based amplicon analysis. LWT, 171, 114166, pp. 1-10. (Year: 2022).*

Zihao et al., 2016. Detection of *Lactobacillus acidophilus* in fermented material by real-time fluorescent quantitative PCR. Animal Husbandry and Feed Science, 8(1), pp. 54-57. (Year: 2016).*

NCBI, GenBank Accession No. CP017062.1, '*Lactobacillus acidophilus* strain LA1, complete genome,' Oct. 21, 2017.

NCBI, GenBank Accession No. CP025200.1, '*Lactobacillus acidophilus* strain YT1 chromosome, complete genome,' Dec. 17, 2019.

Eun Yeong Lim, et al. "Attenuating Effects of *Lactobacillus acidophilus* YT1 on Menopausal Symptoms in Ovariectomized Rats," (Oct. 20, 2018) Journal of the Korean Society for Food and Nutrition, vol. 47, No. 12.1225-1233.

NCBI, GenBank Accession No. CP020620, '*Lactobacillus acidophilus* strain DSM 20079 chromosome, complete genome' Apr. 10, 2018.

* cited by examiner

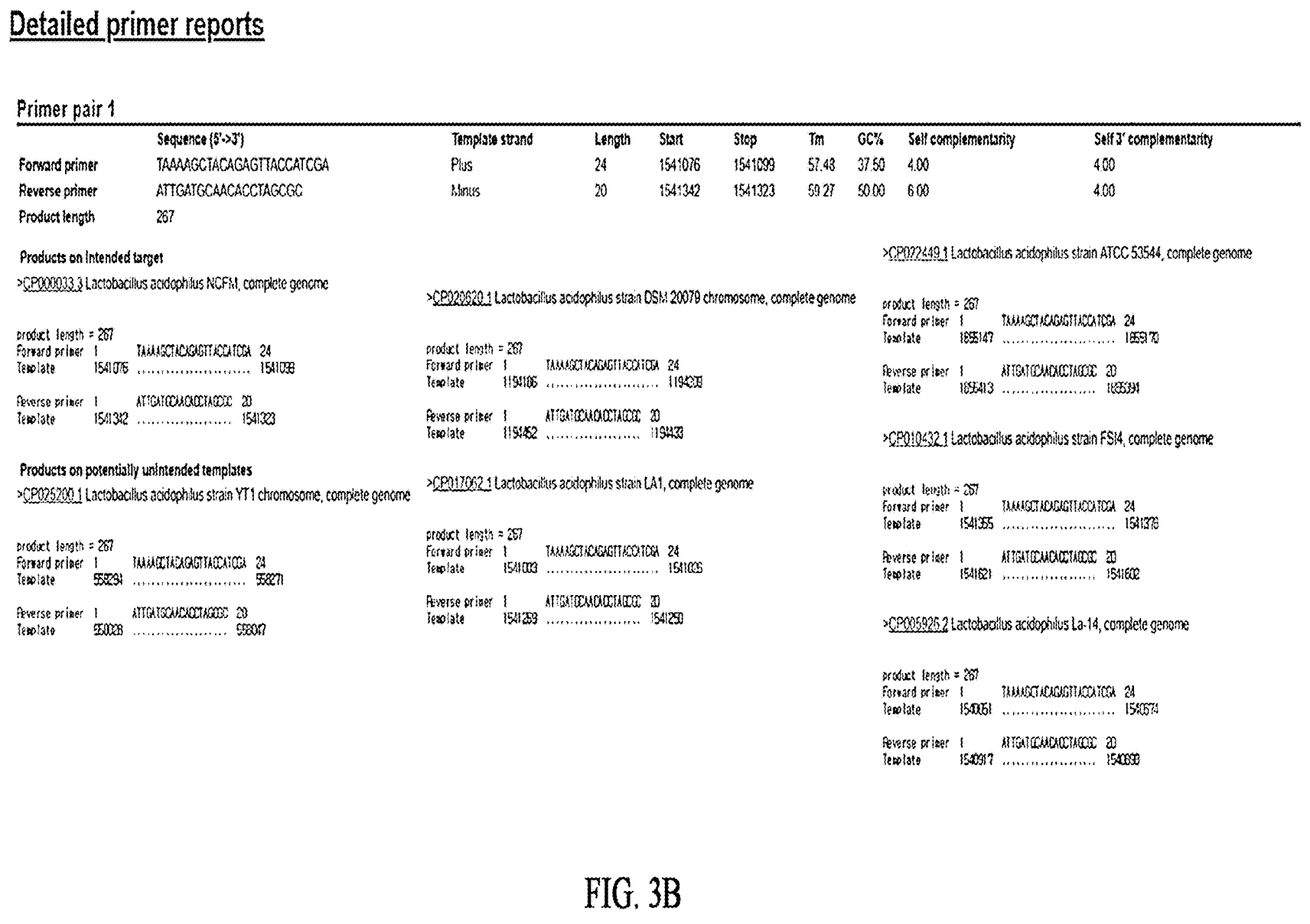

Detailed primer reports

Primer pair 1

| | Sequence (5'->3') | Template strand | Length | Start | Stop | Tm | GC% | Self complementarity | Self 3' complementarity |
|---|---|---|---|---|---|---|---|---|---|
| Forward primer | TAAAAGCTACAGAGTTACCATCGA | Plus | 24 | 1541076 | 1541099 | 57.48 | 37.50 | 4.00 | 4.00 |
| Reverse primer | ATTGATGCAACACCTAGCCGC | Minus | 20 | 1541342 | 1541323 | 59.27 | 50.00 | 6.00 | 4.00 |
| Product length | 267 | | | | | | | | |

Products on Intended target

>CP000033.3 Lactobacillus acidophilus NCFM, complete genome

>CP072449.1 Lactobacillus acidophilus strain ATCC 53544, complete genome

Products on potentially unintended templates

>CP028620.1 Lactobacillus acidophilus strain DSM 20079 chromosome, complete genome >CP017062.1 Lactobacillus acidophilus strain LA1, complete genome >CP010432.1 Lactobacillus acidophilus strain FSI4, complete genome >CP025200.1 Lactobacillus acidophilus strain YT1 chromosome, complete genome >CP005926.2 Lactobacillus acidophilus La-14, complete genome

FIG. 3B

Site for 16S comparison

- With reference to 16S rRNA of L. acidophilus NCFM
- Location : 18~784
- Length : 767 bp
- Hypervariable region: V1~V4
- Outgroup: *L. helveticus* CAUH18

FIG. 11

YT1 amplification site: spacers 5-d of CRISPR 1 region
Left primer: 6-25 bp of spacer 5
Right primer: 1-20 bp of spacer d (reverse complement)

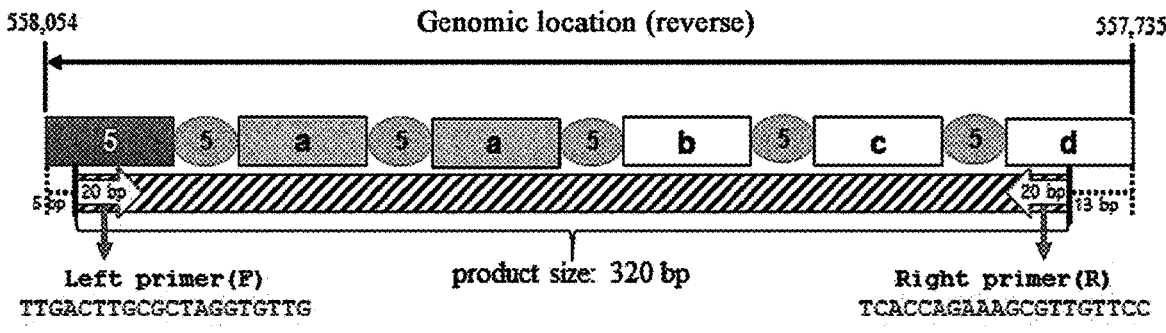

558,054            Genomic location (reverse)            557,735

Left primer (F)
TTGACTTGCGCTAGGTGTTG product size: 320 bp

Right primer (R)
TCACCAGAAAGCGTTGTTCC

Sequence data

DR5: GGATCACCTCCACATACGTGGAGAAAAT
Spacer 5: CCAGGTTGACTTGCGCTAGGTGTTGCATCAATA
Spacer a: GACACCAAAAAGGGCGGTGGAAAACTTTTCAAA
Spacer b: ACTTCAACTAATCCTAATTATCCTGGCAATCCA
Spacer c: GCCTAGTGCCTTACCAGCCTCGGCAAAACTGTG
Spacer d: GGAACAACGCTTTCTGGTGAATATATTGACTTG M : Sizer™ 100bp DNA Marker(Cat .No. 24073)
1 : *Lactobacillus helveticus* ATCC 13866
2 : *Lactobacillus amylovorus* ATCC 33620
3 : *Lactobacillus acidophilus* ATCC 4356
4 : *Lactobacillus acidophilus* NCFM
5 : *Lactobacillus acidophilus* CB_LA1
6 : *Lactobacillus acidophilus* YT1

M : Sizer™ 100bp DNA Marker(Cat. No. 24073)

Uni-a : *Lactobacillus acidophilus* YT1

Uni-b : *Lactobacillus acidophilus* YT1

M : Sizer™ 100bp DNA Marker(Cat. No. 24073)

M : Sizer™ 100bp DNA Marker(Cat .No. 24073)
1 : *Lactobacillus helveticus* ATCC 13866
2 : *Lactobacillus  amylovorus* ATCC 33620
3 : *Lactobacillus acidophilus* ATCC 4356
4 : *Lactobacillus acidophilus* NCFM
5 : *Lactobacillus acidophilus* CB_LA1

FIG. 20

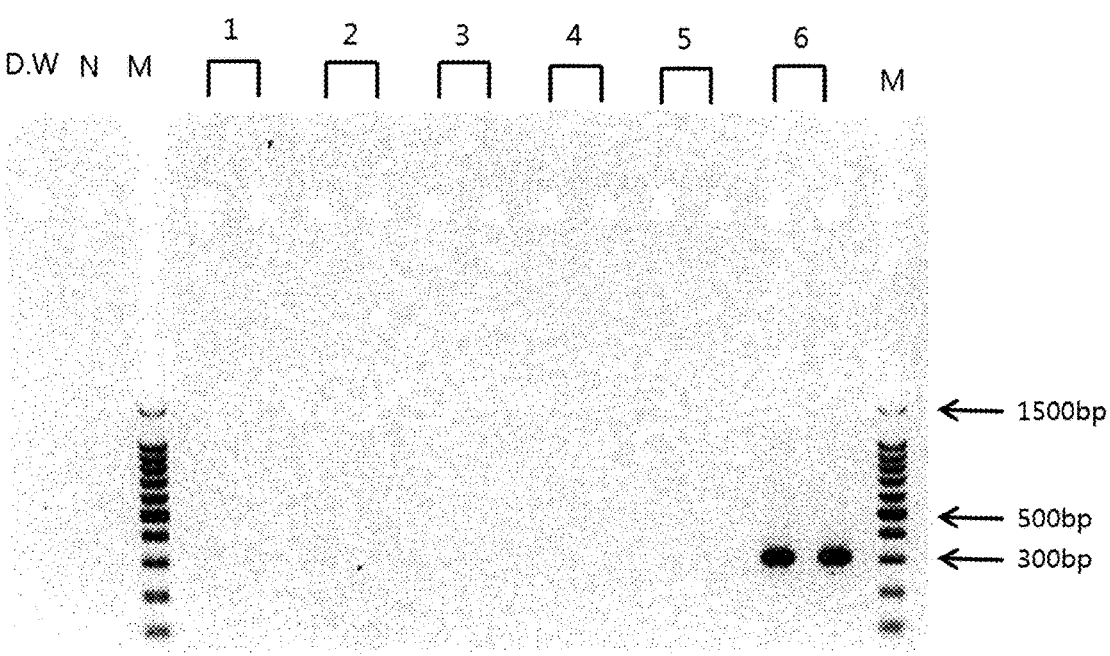

M : Sizer™ 100bp DNA Marker(Cat .No. 24073)
1 : *Lactobacillus helveticus* ATCC 13866
2 : *Lactobacillus amylovorus* ATCC 33620
3 : *Lactobacillus acidophilus* ATCC 4356
4 : *Lactobacillus acidophilus* NCFM
5 : *Lactobacillus acidophilus* CB_LA1
6 : *Lactobacillus acidophilus* YT1

• Target Primer : YT1
• Expected YT1 band size : 320bp (Primer length포함)
• Left Sequence : TTGACTTGCGCTAGGTGTTG
• Right Sequence : TCACCAGAAAGCGTTGTTCC M : Sizer™ 100bp DNA Marker(Cat. No. 24073)

N : Blank

YT1-a : *Lactobacillus acidophilus* YT1

YT1-b : *Lactobacillus acidophilus* YT1

M : Sizer™ 100bp DNA Marker(Cat. No. 24073)

SEQUENCE LISTING

<160> NUMBER OF SEQ ID NOS: 42

<210> SEQ ID NO 1
<211> LENGTH: 24
<212> TYPE: DNA
<213> ORGANISM: Artificial Sequence
<220> FEATURE:
<223> OTHER INFORMATION: CRISPR_LA_uni_F

```
<400> SEQUENCE: 1
taaaagctac agagttacca tcga                                                24

<210> SEQ ID NO 2
<211> LENGTH: 25
<212> TYPE: DNA
<213> ORGANISM: Artificial Sequence
<220> FEATURE:
<223> OTHER INFORMATION: CRISPR_LA_uni_S1-S4_F

<400> SEQUENCE: 2
ggctctaaaa gctacagagt tacca                                               25

<210> SEQ ID NO 3
<211> LENGTH: 25
<212> TYPE: DNA
<213> ORGANISM: Artificial Sequence
<220> FEATURE:
<223> OTHER INFORMATION: CRISPR_LA_uni_S1-S3_F

<400> SEQUENCE: 3
ggctctaaaa gctacagagt tacca                                               25

<210> SEQ ID NO 4
<211> LENGTH: 24
<212> TYPE: DNA
<213> ORGANISM: Artificial Sequence
<220> FEATURE:
<223> OTHER INFORMATION: CRISPR_LA_uni_S2-S5_F

<400> SEQUENCE: 4
tcatcgtaag aaataagtcg cata                                                24

<210> SEQ ID NO 5
<211> LENGTH: 26
<212> TYPE: DNA
<213> ORGANISM: Artificial Sequence
<220> FEATURE:
<223> OTHER INFORMATION: CRISPR_LA_uni_S2-S4_F

<400> SEQUENCE: 5
tctcatcgta agaaataagt cgcata                                              26

<210> SEQ ID NO 6
<211> LENGTH: 24
<212> TYPE: DNA
<213> ORGANISM: Artificial Sequence
<220> FEATURE:
<223> OTHER INFORMATION: CRISPR_LA_uni_S3-S5_F

<400> SEQUENCE: 6
ccttttccta ggatcttcat aagc                                                24

<210> SEQ ID NO 7
<211> LENGTH: 20
<212> TYPE: DNA
<213> ORGANISM: Artificial Sequence
<220> FEATURE:
<223> OTHER INFORMATION: CRISPR_YT1_F

<400> SEQUENCE: 7
ttgacttgcg ctaggtgttg                                                     20

<210> SEQ ID NO 8
<211> LENGTH: 20
```

```
<212> TYPE: DNA
<213> ORGANISM: Artificial Sequence
<220> FEATURE:
<223> OTHER INFORMATION: CRISPR_LA_F

<400> SEQUENCE: 8
ttgacttgcg ctaggtgttg                                                    20

<210> SEQ ID NO 9
<211> LENGTH: 20
<212> TYPE: DNA
<213> ORGANISM: Artificial Sequence
<220> FEATURE:
<223> OTHER INFORMATION: CRISPR_LA_uni_R

<400> SEQUENCE: 9
attgatgcaa cacctagcgc                                                    20

<210> SEQ ID NO 10
<211> LENGTH: 22
<212> TYPE: DNA
<213> ORGANISM: Artificial Sequence
<220> FEATURE:
<223> OTHER INFORMATION: CRISPR_LA_uni_S1-S4_R

<400> SEQUENCE: 10
cagggtggtt ttaagtacga ga                                                 22

<210> SEQ ID NO 11
<211> LENGTH: 20
<212> TYPE: DNA
<213> ORGANISM: Artificial Sequence
<220> FEATURE:
<223> OTHER INFORMATION: CRISPR_LA_uni_S1-S3_R

<400> SEQUENCE: 11
tggcgagaag cttatgaaga                                                    20

<210> SEQ ID NO 12
<211> LENGTH: 20
<212> TYPE: DNA
<213> ORGANISM: Artificial Sequence
<220> FEATURE:
<223> OTHER INFORMATION: CRISPR_LA_uni_S2-S5_R

<400> SEQUENCE: 12
caacacctag cgcaagtcaa                                                    20

<210> SEQ ID NO 13
<211> LENGTH: 22
<212> TYPE: DNA
<213> ORGANISM: Artificial Sequence
<220> FEATURE:
<223> OTHER INFORMATION: CRISPR_LA_uni_S2-S4_R

<400> SEQUENCE: 13
cagggtggtt ttaagtacga ga                                                 22

<210> SEQ ID NO 14
<211> LENGTH: 21
<212> TYPE: DNA
<213> ORGANISM: Artificial Sequence
<220> FEATURE:
<223> OTHER INFORMATION: CRISPR_LA_uni_S3-S5_R

<400> SEQUENCE: 14
```

-continued

```
atgcaacacc tagcgcaagt c                                              21

<210> SEQ ID NO 15
<211> LENGTH: 20
<212> TYPE: DNA
<213> ORGANISM: Artificial Sequence
<220> FEATURE:
<223> OTHER INFORMATION: CRISPR_YT1_R

<400> SEQUENCE: 15
tcaccagaaa gcgttgttcc                                                20

<210> SEQ ID NO 16
<211> LENGTH: 20
<212> TYPE: DNA
<213> ORGANISM: Artificial Sequence
<220> FEATURE:
<223> OTHER INFORMATION: CRISPR_LA_R

<400> SEQUENCE: 16
gcgtggcaaa tgaatggttg                                                20

<210> SEQ ID NO 17
<211> LENGTH: 267
<212> TYPE: DNA
<213> ORGANISM: Artificial Sequence
<220> FEATURE:
<223> OTHER INFORMATION: amplicon sequence

<400> SEQUENCE: 17
taaaagctac agagttacca tcgaggatca cctccacttt cgtggagaaa attggaatct     60
catcgtaaga aataagtcgc atataggatc acctccacat acgtggagaa aatccttttc    120
ctaggatctt cataagcttc tcgccaggat cacctccaca tacgtggaga aaatatcgta    180
gtcaatctcg tacttaaaac caccctggga tcacctccac atacgtggag aaaatccagg    240
ttgacttgcg ctaggtgttg catcaat                                        267

<210> SEQ ID NO 18
<211> LENGTH: 897
<212> TYPE: DNA
<213> ORGANISM: Artificial Sequence
<220> FEATURE:
<223> OTHER INFORMATION: amplicon sequence

<400> SEQUENCE: 18
catcaatagg atcacctcca catacgtgga gaaaattagg caaatagcca atttttatca     60
tacattccgg gatcacctcc acatacgtgg agaaaatcgg caattttttga aacaaacaac    120 tatgtatata ggatcacctc cacatacgtg gagaaaataa ataaggaaga tattgccacc    180
ctcggtaccc aggatcacct ccacatacgt ggagaaaata caagtttttgc tctaaccatg    240 atgttgtaaa caggatcacc tccacatacg tggagaaaat acgttaaagc ggacaataag    300
cttcaacgtt ttaggatcac ctccacatac gtggagaaaa tcgtgcttga aattgctctc    360
ggggtttcgc ctaaggatca cctccacata cgtggagaaa atatttgctg cgagtaactc    420
tgacttgttt acccgggatc acctccacat acgtggagaa aatttttagct aagtttaaga    480 ccgaagatgg ccaaagggat cacctccaca tacgtggaga aaatcggcaa tttttgaaac    540
aaacaactat gtatatagga tcacctccac atacgtggag aaaatcggca atttttgaaa    600
caaacaacta tgtatatagg atcacctcca catacgtgga gaaaatacaa gttttgctct    660
aaccatgatg ttgtaaacag gatcacctcc acatacgtgg agaaaatagc tatccaaata    720
```

-continued

```
ttaaatttgc actagttaag gggatcacct ccacatacgt ggagaaaatg aagaatttta     780
tcttctaggt ggctttttg tgggatcacc tccacatacg tggagaaaat agaaatattt     840
gattttgata gtgaaaaaga ataggatcac ctccacatac gtggagaaat tcagtcc       897

<210> SEQ ID NO 19
<211> LENGTH: 837
<212> TYPE: DNA
<213> ORGANISM: Artificial Sequence
<220> FEATURE:
<223> OTHER INFORMATION: amplicon sequence

<400> SEQUENCE: 19
catcaatagg atcacctcca catacgtgga gaaaattagg caaatagcca atttttatca      60
tacattccgg gatcacctcc acatacgtgg agaaaatcgg caatttttga aacaaacaac     120
tatgtatata ggatcacctc cacatacgtg gagaaaataa ataaggaaga tattgccacc     180
ctcggtaccc aggatcacct ccacatacgt ggagaaaata cgttaaagcg gacaataagc     240
ttcaacgttt taggatcacc tccacatacg tggagaaat cgtgcttgaa attgctctcg      300
gggtttcgcc taaggatcac ctccacatac gtggagaaaa tatttgctgc gagtaactct     360
gacttgttta cccgggatca cctccacata cgtggagaaa attttagcta agtttaagac     420
cgaagatggc caaagggatc acctccacat acgtggagaa aatcggcaat ttttgaaaca     480
aacaactatg tatataggat cacctccaca tacgtggaga aaatcggcaa tttttgaaac     540
aaacaactat gtatatagga tcacctccac atacgtggag aaaatacaag ttttgctcta     600
accatgatgt tgtaaacagg atcacctcca catacgtgga gaaaatagct atccaaatat     660
taaatttgca ctagttaagg ggatcacctc cacatacgtg gagaaaatga agaattttat     720
cttctaggtg gctttttgt gggatcacct ccacatacgt ggagaaaata gaaatatttg     780
attttgatag tgaaaagaa taggatcacc tccacatacg tggagaaatt cagatac        837

<210> SEQ ID NO 20
<211> LENGTH: 165
<212> TYPE: DNA
<213> ORGANISM: Artificial Sequence
<220> FEATURE:
<223> OTHER INFORMATION: amplicon sequence

<400> SEQUENCE: 20
catcaatagg atcacctcca catacgtgga gaaatgaag aattttatct tctaggtggc      60 tttttgtgg gatcacctcc acatacgtgg agaaaataga aatatttgat tttgatagtg     120
aaaaagaata ggatcacctc cacatacgtg gagaaaattc aagat                    165

<210> SEQ ID NO 21
<211> LENGTH: 320
<212> TYPE: DNA
<213> ORGANISM: Artificial Sequence
<220> FEATURE:
<223> OTHER INFORMATION: amplicon sequence

<400> SEQUENCE: 21
ttgacttgcg ctaggtgttg catcaatagg atcacctcca catacgtgga gaaatgaca      60 ccaaaaaggg cggtggaaaa cttttcaaag gatcacctcc acatacgtgg agaaaatgac     120
accaaaaagg gcggtggaaa acttttcaaa ggatcacctc cacatacgtg gagaaaatac     180
ttcaactaat cctaattatc ctggcaatcc aggatcacct ccacatacgt ggagaaaatg     240
```

```
cctagtgcct taccagcctc ggcaaaactg tgggatcacc tccacatacg tggagaaaat        300
ggaacaacgc tttctggtga                                                    320

<210> SEQ ID NO 22
<211> LENGTH: 33
<212> TYPE: DNA
<213> ORGANISM: Artificial Sequence
<220> FEATURE:
<223> OTHER INFORMATION: synthetic construct

<400> SEQUENCE: 22
ccaggttgac ttgcgctagg tgttgcatca ata                                       33

<210> SEQ ID NO 23
<211> LENGTH: 33
<212> TYPE: DNA
<213> ORGANISM: Artificial Sequence
<220> FEATURE:
<223> OTHER INFORMATION: synthetic construct

<400> SEQUENCE: 23
ccaggttgac ttgcgctagg tgttgcatca ata                                       33

<210> SEQ ID NO 24
<211> LENGTH: 33
<212> TYPE: DNA
<213> ORGANISM: Artificial Sequence
<220> FEATURE:
<223> OTHER INFORMATION: synthetic construct

<400> SEQUENCE: 24
gctggtgacc ttgcgctagg tgttgcaaca att                                       33

<210> SEQ ID NO 25
<211> LENGTH: 33
<212> TYPE: DNA
<213> ORGANISM: Artificial Sequence
<220> FEATURE:
<223> OTHER INFORMATION: synthetic construct

<400> SEQUENCE: 25
agctcctgac ttgcgctagg tgttgaaaaa aca                                       33

<210> SEQ ID NO 26
<211> LENGTH: 33
<212> TYPE: DNA
<213> ORGANISM: Artificial Sequence
<220> FEATURE:
<223> OTHER INFORMATION: synthetic construct

<400> SEQUENCE: 26
tcaagatcaa ccattcattt gccacgcaaa tcg                                       33

<210> SEQ ID NO 27
<211> LENGTH: 33
<212> TYPE: DNA
<213> ORGANISM: Artificial Sequence
<220> FEATURE:
<223> OTHER INFORMATION: synthetic construct

<400> SEQUENCE: 27
tcaagatcaa ccatttattt gccacgcaaa tcg                                       33

<210> SEQ ID NO 28
<211> LENGTH: 33
```

-continued

```
<212> TYPE: DNA
<213> ORGANISM: Artificial Sequence
<220> FEATURE:
<223> OTHER INFORMATION: synthetic construct

<400> SEQUENCE: 28
ccaagatcaa ccatttattt gccacgcaaa tcg                          33

<210> SEQ ID NO 29
<211> LENGTH: 33
<212> TYPE: DNA
<213> ORGANISM: Artificial Sequence
<220> FEATURE:
<223> OTHER INFORMATION: synthetic construct

<400> SEQUENCE: 29
tcagaaccaa ccattcattt gtcacgcaaa tcg                          33

<210> SEQ ID NO 30
<211> LENGTH: 33
<212> TYPE: DNA
<213> ORGANISM: Artificial Sequence
<220> FEATURE:
<223> OTHER INFORMATION: synthetic construct

<400> SEQUENCE: 30
gcaagatcaa ccattcattt gattttctgt caa                          33

<210> SEQ ID NO 31
<211> LENGTH: 33
<212> TYPE: DNA
<213> ORGANISM: Artificial Sequence
<220> FEATURE:
<223> OTHER INFORMATION: synthetic construct

<400> SEQUENCE: 31
tcaagatcaa cctttcattt gccgtgctaa ccg                          33

<210> SEQ ID NO 32
<211> LENGTH: 33
<212> TYPE: DNA
<213> ORGANISM: Artificial Sequence
<220> FEATURE:
<223> OTHER INFORMATION: synthetic construct

<400> SEQUENCE: 32
gttggatcaa ccattcattt gccgcaaaac tgt                          33

<210> SEQ ID NO 33
<211> LENGTH: 33
<212> TYPE: DNA
<213> ORGANISM: Artificial Sequence
<220> FEATURE:
<223> OTHER INFORMATION: synthetic construct

<400> SEQUENCE: 33
aagccatcaa ccattcattt gccaatacaa tca                          33

<210> SEQ ID NO 34
<211> LENGTH: 33
<212> TYPE: DNA
<213> ORGANISM: Artificial Sequence
<220> FEATURE:
<223> OTHER INFORMATION: synthetic construct

<400> SEQUENCE: 34
```

-continued aacgcatcaa ccattcattt gccattcgac tat                                33

<210> SEQ ID NO 35
<211> LENGTH: 33
<212> TYPE: DNA
<213> ORGANISM: Artificial Sequence
<220> FEATURE:
<223> OTHER INFORMATION: synthetic construct

<400> SEQUENCE: 35
tcaagatcaa ccattcattt gccacgcaaa tcg                                33

<210> SEQ ID NO 36
<211> LENGTH: 33
<212> TYPE: DNA
<213> ORGANISM: Artificial Sequence
<220> FEATURE:
<223> OTHER INFORMATION: synthetic construct

<400> SEQUENCE: 36
gctcagtcaa ccattcattt gccactctga cct                                33

<210> SEQ ID NO 37
<211> LENGTH: 33
<212> TYPE: DNA
<213> ORGANISM: Artificial Sequence
<220> FEATURE:
<223> OTHER INFORMATION: synthetic construct

<400> SEQUENCE: 37
atttattttg gcattcattt gccacgcaaa cgt                                33

<210> SEQ ID NO 38
<211> LENGTH: 33
<212> TYPE: DNA
<213> ORGANISM: Artificial Sequence
<220> FEATURE:
<223> OTHER INFORMATION: synthetic construct

<400> SEQUENCE: 38
acaagatcaa ccattcattt tcgtttagac ctt                                33

<210> SEQ ID NO 39
<211> LENGTH: 33
<212> TYPE: DNA
<213> ORGANISM: Artificial Sequence
<220> FEATURE:
<223> OTHER INFORMATION: synthetic construct

<400> SEQUENCE: 39
aaaccatcaa ccattcattt gccaatacaa tca                                33

<210> SEQ ID NO 40
<211> LENGTH: 33
<212> TYPE: DNA
<213> ORGANISM: Artificial Sequence
<220> FEATURE:
<223> OTHER INFORMATION: synthetic construct

<400> SEQUENCE: 40
tcaagatcaa ccattcatta agccctgctt gcc                                33

<210> SEQ ID NO 41
<211> LENGTH: 33
<212> TYPE: DNA
<213> ORGANISM: Artificial Sequence -continued

```
<220> FEATURE:
<223> OTHER INFORMATION: synthetic construct

<400> SEQUENCE: 41
ttaagatcaa ccattcattt gtgaattaca ggc                                          33

<210> SEQ ID NO 42
<211> LENGTH: 33
<212> TYPE: DNA
<213> ORGANISM: Artificial Sequence
<220> FEATURE:
<223> OTHER INFORMATION: synthetic construct

<400> SEQUENCE: 42
tcattggcaa ccattcattt gtcacgcaaa acc                                          33
```

COMPOSITION FOR DISCRIMINATING *LACTOBACILLUS ACIDOPHILUS* STRAINS AND DISCRIMINATION METHOD USING SAME

CROSS-REFERENCE TO RELATED APPLICATIONS

This application is a § 371 national stage entry of International Application No. PCT/KR2019/006460, filed May 29, 2019, which claims priority to Korean Patent Application No. 10-2018-0113928, filed on Sep. 21, 2018, Korean Patent Application No. 10-2019-0040985, filed on Apr. 8, 2019, and Korean Patent Application No. 10-2019-0040986, filed on Apr. 8, 2019, the entire contents of which are incorporated herein by reference.

SEQUENCE LISTING

The instant application contains a Sequence Listing, which has been submitted electronically in ASCII format, and is hereby incorporated by reference in its entirety. Said ASCII copy, created on Jun. 6, 2025, is named G1035-19001_SequenceListing.txt and is 11,449 bytes in size.

TECHNICAL FIELD

The present disclosure relates to a composition for discriminating the species *Lactobacillus acidophilus*, more particularly to a universal primer composition capable of specifically discriminating and identifying the species *acidophilus* from the genus *Lactobacillus* quickly and accurately, a primer composition for discriminating and identifying individual *Lactobacillus acidophilus* strains, and a primer composition for discriminating a *Lactobacillus acidophilus* YT1 strain. The present disclosure also relates to a kit including the primer composition and a discrimination method using the same.

BACKGROUND ART

Lactic acid bacteria are bacteria which degrade carbohydrates into lactic acid through metabolism. They are used to ferment foods such as yogurt, lactic acid bacteria drinks, kimchi, etc.

Lactic acid bacteria exhibit various effects depending on strains. They can be classified into the five genera of *Streptococcus, Lactobacillus, Leuconostoc*, Bifidobacteria and *Pediococcus*. The microorganisms belonging to the genus *Lactobacillus* among them are homofermentative or heterofermentative *lactobacillus* bacteria and are usually found during fermentation of dairy products or vegetables. The microorganisms in the genus *Leuconostoc* are heterofermentative and are mainly involved in the fermentation of vegetables.

Among the microorganisms belonging to the genus *Lactobacillus*, the species *Lactobacillus acidophilus* is used in various products because it has strong adherence ability to human small intestine, can endure gastric acid or bile acid due to excellent acid resistance and has many probiotic characteristics of lactic acid bacteria, such as lowering of cholesterol, improvement of diarrhea and constipation, enhancement of immunity, etc. In addition, with proven usability through various researches on applicability as probiotics, production of useful products, inhibition of the growth of harmful microorganisms, co-culture with other lactic acid bacteria or yeasts, change in gut flora, antibiotic adaptability, assimilation of cholesterol, etc., development and utilization of more functional food additives, sanitary goods, cosmetics, etc. are expected.

Therefore, the importance of detection, discrimination and identification methods capable of specifically discriminating the species *acidophilus* from the genus *Lactobacillus* is increasing gradually.

The most representative method of discriminating the species of microorganisms developed thus far is the analysis of the gene base sequence information of 16S rRNA. This method is disadvantageous in that the criteria for determining the 16S rRNA gene base sequence are not applicable to some *Lactobacillus acidophilus* strains and the method is time-consuming and labor-intensive.

Recently, Genesig (UK) developed a kit for discriminating the species *Lactobacillus acidophilus* based on the base sequence of the recombinase A (recA) gene of *Lactobacillus acidophilus*. However, it is limited in that only 95% of the *Lactobacillus acidophilus* strains in the NCBI database can be detected. In addition, since many mutations can be made to the specific genes of the microorganisms, the methods targeting specific genes are limited in detecting the various microorganisms of the species *Lactobacillus acidophilus*.

In addition, although the NGS analysis technology allows discrimination of the species of a specific microorganism based on the whole genome analysis result of the microorganism, it is disadvantageous in that the complicated process of comparing genome data and identifying the species and drawing up the genealogy of each strain is necessary and the method is time-consuming and labor-intensive. Also, the method is limited in detecting a number of species at the same time.

The inventors of the present disclosure have made efforts to develop a species-specific universal primer composition capable of specifically detecting *Lactobacillus acidophilus* by identifying the CRISPR region of *Lactobacillus acidophilus* having useful effects for human body, which is distinguished from the microorganisms of other species, and a specific primer composition capable of specifically detecting individual *Lactobacillus acidophilus* strains by analyzing the CRISPR region, and have completed the present disclosure.

DISCLOSURE

Technical Problem

The present disclosure is directed to providing a primer composition for discriminating the species *Lactobacillus acidophilus*, which includes a primer set consisting of one or more forward primer selected from SEQ ID NOS: 1-8 and one or more reverse primer selected from SEQ ID NOS: 9-16.

The present disclosure is also directed to providing a primer composition for discriminating individual *Lactobacillus acidophilus* strains.

The present disclosure is also directed to providing a primer composition for discriminating a *Lactobacillus acidophilus* YT1 strain.

The present disclosure is also directed to providing a kit including the primer composition.

The present disclosure is also directed to providing a method for discriminating the species *Lactobacillus acidophilus*.

The present disclosure is also directed to providing a method for discriminating individual *Lactobacillus acidophilus* strains.

The present disclosure is also directed to providing a method for discriminating a *Lactobacillus acidophilus* YT1 strain.

The present disclosure is also directed to providing a method for detecting the presence of a *Lactobacillus acidophilus* strain in a clinical, environmental or food sample.

The present disclosure is also directed to providing a method for detecting the presence of individual *Lactobacillus acidophilus* strains in a clinical, environmental or food sample.

The present disclosure is also directed to providing a method for detecting the presence of a *Lactobacillus acidophilus* YT1 strain in a clinical, environmental or food sample.

The present disclosure is also directed to providing a use of a primer set consisting of one or more forward primer selected from SEQ ID NOS: 1-8 and one or more reverse primer selected from SEQ ID NOS: 9-16 for detection of a *Lactobacillus acidophilus* strain.

Technical Solution

The present disclosure provides a primer composition for discriminating the species *Lactobacillus acidophilus*, which includes a primer set consisting of one or more forward primer selected from SEQ ID NOS: 1-8 and one or more reverse primer selected from SEQ ID NOS: 9-16.

According to an exemplary embodiment of the present disclosure, the forward primer may further include one or more label selected from a group consisting of a fluorophore, a chromophore, a chemiluminophore, a magnetic particle and a radioisotope linked to the 5'-end.

The present disclosure also provides a primer composition for discriminating individual *Lactobacillus acidophilus* strains, which includes a primer set consisting of a forward primer represented by SEQ ID NO: 8 and a reverse primer represented by SEQ ID NO: 16.

According to another exemplary embodiment of the present disclosure, the composition may further include a primer set consisting of a forward primer represented by SEQ ID NO: 7 and a reverse primer represented by SEQ ID NO: 15.

The present disclosure also provides a primer composition for discriminating a *Lactobacillus acidophilus* YT1 strain, which includes a primer set consisting of a forward primer represented by SEQ ID NO: 7 and a reverse primer represented by SEQ ID NO: 15.

The present disclosure also provides a kit including the primer composition.

According to another exemplary embodiment of the present disclosure, the kit may be used for discrimination of the species *Lactobacillus acidophilus*, discrimination of individual *Lactobacillus acidophilus* strains or discrimination of a *Lactobacillus acidophilus* YT1 strain depending on the primer set included in the primer composition.

According to another exemplary embodiment of the present disclosure, the kit may include a buffer, a DNA polymerase and a dNTP.

The present disclosure also provides a method for discriminating the species *Lactobacillus acidophilus*, which includes: a) a step of obtaining a PCR product through polymerase chain reaction (PCR) by using a DNA isolated from a target sample to be discriminated as a template and using a primer set consisting of one or more forward primer selected from SEQ ID NOS: 1-8 and one or more reverse primer selected from SEQ ID NOS: 9-16; and b) a step of identifying the presence of the PCR product.

The present disclosure also provides a method for discriminating individual *Lactobacillus acidophilus* strains, which includes: A) a step of obtaining a PCR product through polymerase chain reaction (PCR) by using a DNA isolated from a target sample to be discriminated as a template and using a primer set consisting of a forward primer represented by SEQ ID NO: 8 and a reverse primer represented by SEQ ID NO: 16; and b) a step of identifying the presence of the PCR product.

According to another exemplary embodiment of the present disclosure, a primer set consisting of a forward primer represented by SEQ ID NO: 7 and a reverse primer represented by SEQ ID NO: 15 may be further used in the step A).

The present disclosure also provides a method for discriminating a *Lactobacillus acidophilus* YT1 strain, which includes: 1) a step of obtaining a PCR product through polymerase chain reaction (PCR) by using a DNA isolated from a target sample to be discriminated as a template and using a primer set consisting of a forward primer represented by SEQ ID NO: 7 and a reverse primer represented by SEQ ID NO: 15; and 2) a step of identifying the presence of the PCR product.

The present disclosure also provides a method for detecting the presence of a *Lactobacillus acidophilus* strain in a clinical, environmental or food sample, which includes: i) a step of performing polymerase chain reaction (PCR) by using a primer set consisting of one or more forward primer selected from SEQ ID NOS: 1-8 and one or more reverse primer selected from SEQ ID NOS: 9-16; and ii) a step of identifying the formation of a PCR product.

The present disclosure also provides a method for detecting the presence of individual *Lactobacillus acidophilus* strains in a clinical, environmental or food sample, which includes: I) a step of performing polymerase chain reaction (PCR) by using a primer set consisting of a forward primer represented by SEQ ID NO: 8 and a reverse primer represented by SEQ ID NO: 16; and II) a step of identifying the formation of a PCR product.

In the step I), a primer set consisting of a forward primer represented by SEQ ID NO: 7 and a reverse primer represented by SEQ ID NO: 15 may be further used.

The present disclosure also provides a method for detecting a *Lactobacillus acidophilus* YT1 strain from a clinical, environmental or food sample, which includes: a) a step of performing polymerase chain reaction (PCR) by using a primer set consisting of a forward primer represented by SEQ ID NO: 8 and a reverse primer represented by SEQ ID NO: 16; and b) a step of identifying the formation of a PCR product.

The present disclosure also provides a use of a primer set consisting of one or more forward primer selected from SEQ ID NOS: 1-8 and one or more reverse primer selected from SEQ ID NOS: 9-16 for detection of a *Lactobacillus acidophilus* strain.

Advantageous Effects

A composition according to the present disclosure can discriminate, detect and identify the microorganisms belonging to the species *Lactobacillus acidophilus* from a target sample simply, quickly and accurately. Accordingly, it can be usefully used in the development of fermented milk, baby food, dairy products, livestock feed, cosmetics, health supplements, drugs for intestinal disorders, raw materials, etc. using the *Lactobacillus acidophilus* sp. strain.

In addition, the composition according to the present disclosure can discriminate the presence of individual *Lactobacillus acidophilus* strains in a target sample and can, in particular, identify a *Lactobacillus acidophilus* LA1 strain or a *Lactobacillus acidophilus* YT1 strain specifically and accurately.

BRIEF DESCRIPTION OF DRAWINGS

FIG. 3b shows a result of analyzing the sequence of a primer set represented by SEQ ID NOS: 1 and 9, which is capable of specifically detecting *Lactobacillus acidophilus*, using a sequence search program called Primer-BLAST by comparing with the NCBI database.

FIG. 11 shows a primer set capable of specifically detecting *Lactobacillus acidophilus* YT1 and the size of a PCR product obtained by performing PCR using the primer set, analyzed by in silico analysis.

FIG. 13 shows the genealogy of a total of 414 16S rRNA sequences confirmed to having 97% or higher similarity to

6

Figure 13:
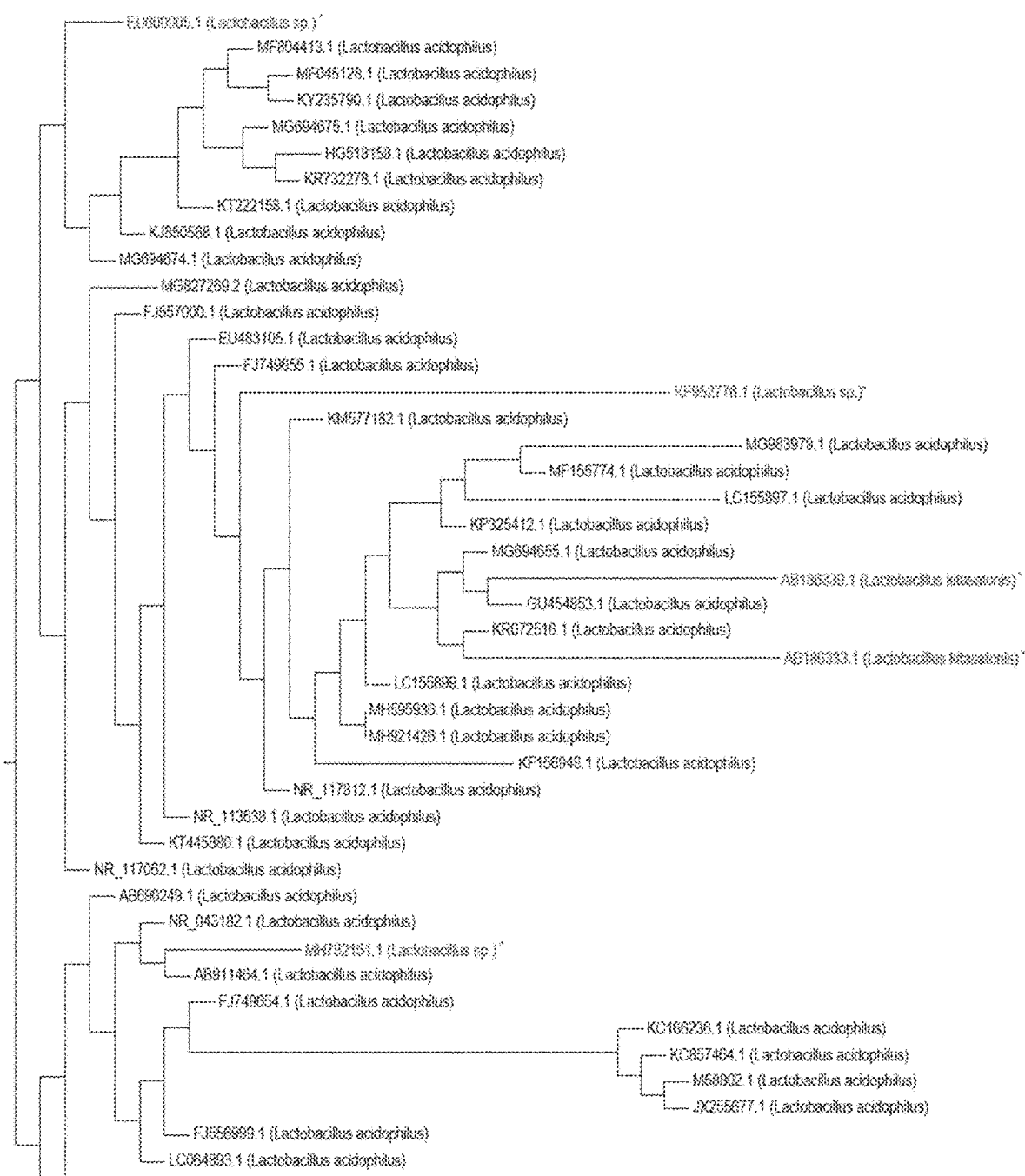

*Lactobacillus acidophilus* NCFM in Test Example 1. In FIG. 13, the sequences other than that of the species *Lactobacillus acidophilus* are shown in red colors and marked with asterisks (*).

Figure 14:
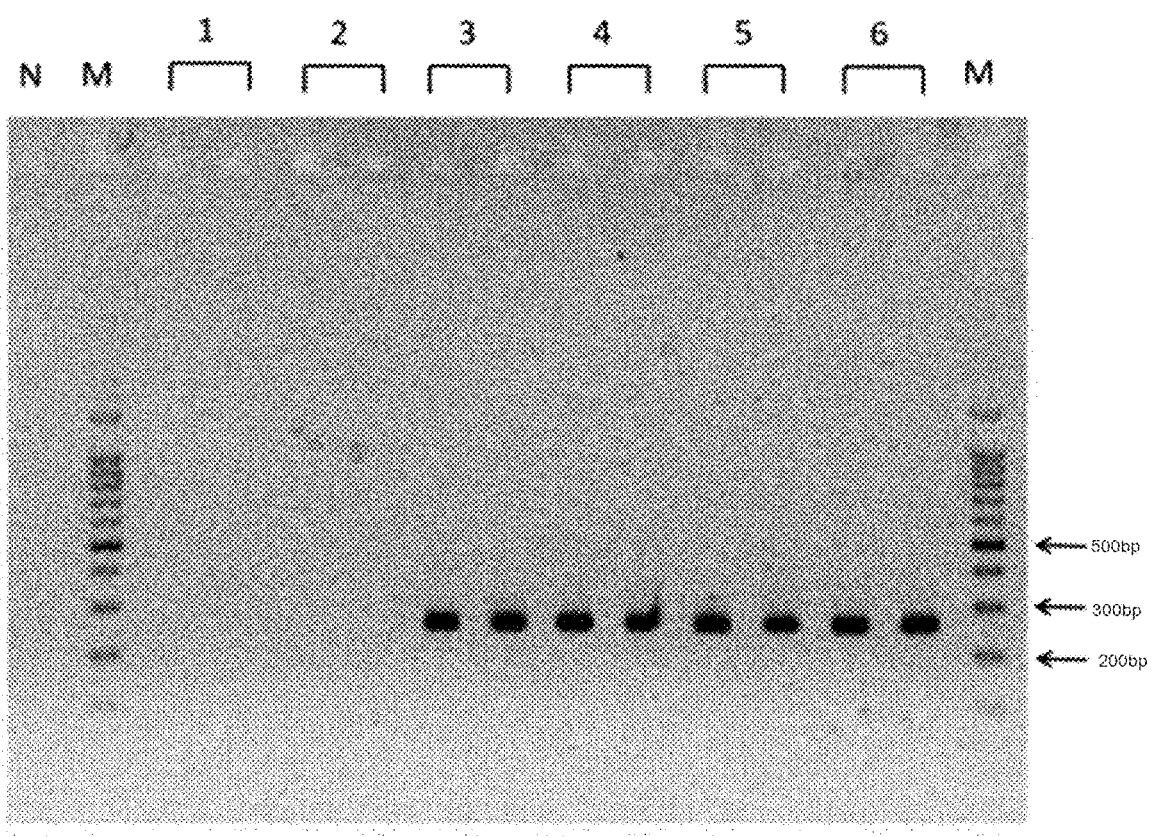

FIG. 14 shows a result of performing PCR for different strains (*Lactobacillus helveticus* ATCC 13866, *Lactobacillus amylovorus* ATCC 33620, *Lactobacillus acidophilus* ATCC 4356, *Lactobacillus acidophilus* NCFM, *Lactobacillus acidophilus* CB_LA1 and *Lactobacillus acidophilus* YT1) using a primer set represented by SEQ ID NOS: 1 and 9 of the present disclosure.

Figure 15:
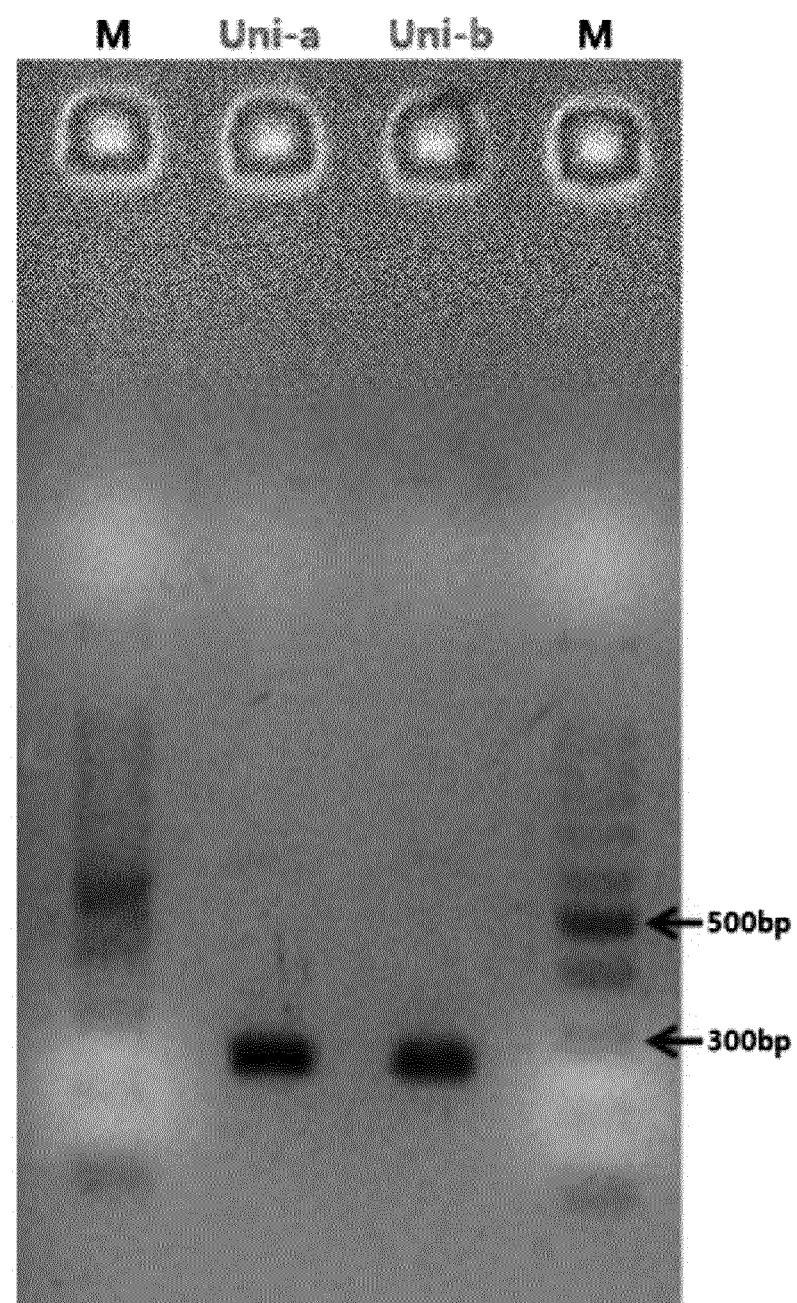

FIG. 15 shows a result of repeating a process of purifying a PCR amplification product obtained by performing PCR for a *Lactobacillus acidophilus* YT1 strain using a primer set represented by SEQ ID NOS: 1 and 9 of the present disclosure and then analyzing the same by agarose gel electrophoresis twice (Uni-a, Uni-b).

Figure 16:
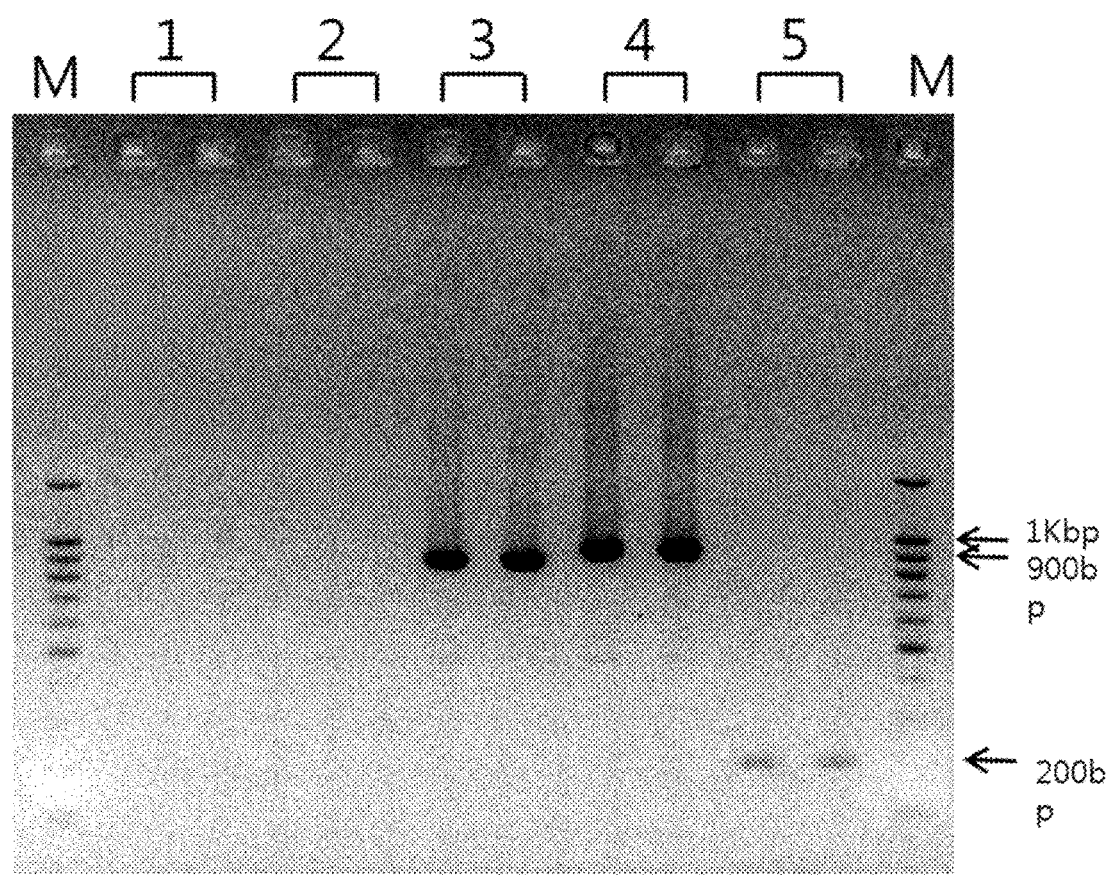

FIG. 16 shows a result of performing PCR for different strains (*Lactobacillus acidophilus* LA1, *Lactobacillus helveticus* ATCC 13866, *Lactobacillus amylovorus* ATCC 33620, *Lactobacillus acidophilus* ATCC 4356 and *Lactobacillus acidophilus* NCFM) using a primer set for discriminating a *Lactobacillus acidophilus* LA1 strain of the present disclosure.

Figure 17:
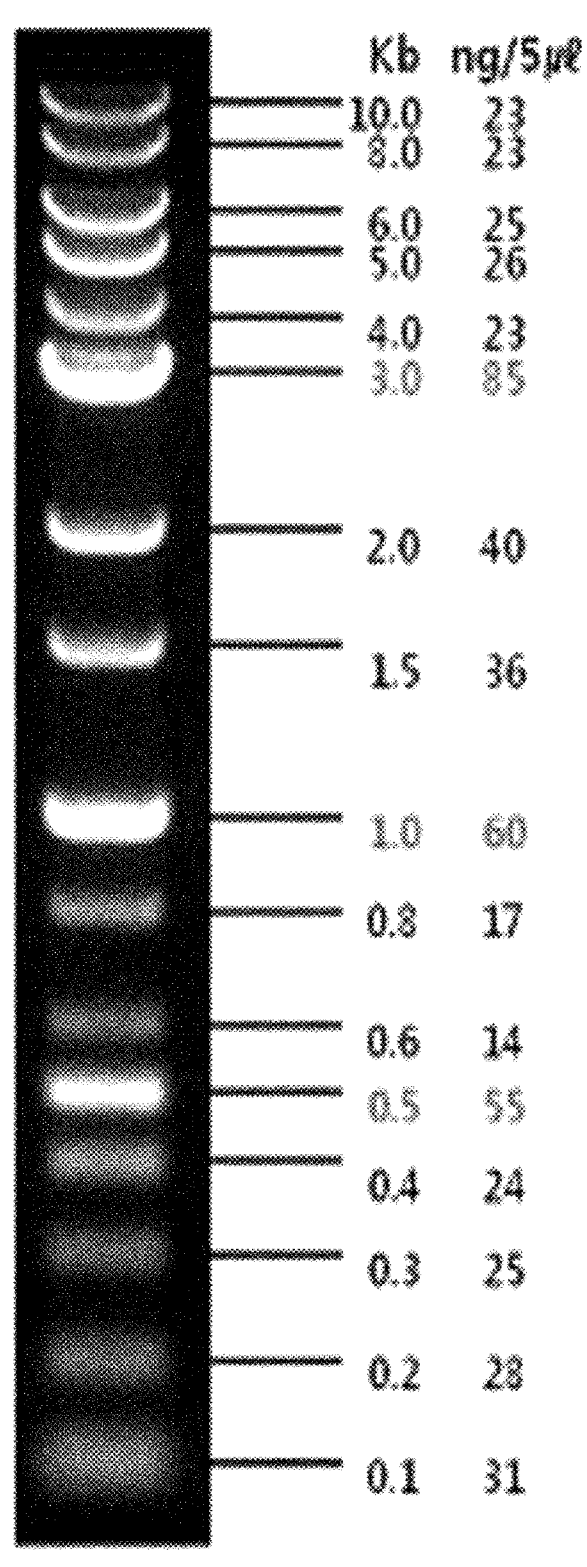

FIG. 17 shows a result of performing PCR for DNA size markers.

Figure 18:
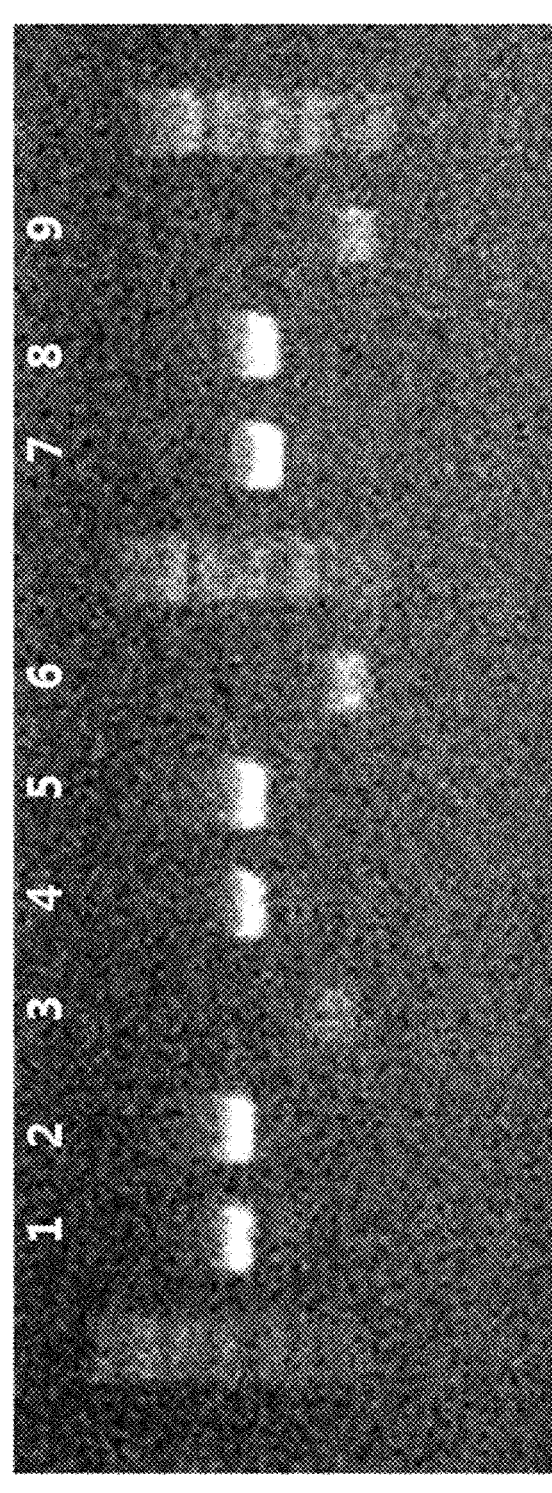

FIG. 18 shows a result of performing PCR for different strains (*Lactobacillus acidophilus* LA1, *Lactobacillus acidophilus* ATCC 4356 and *Lactobacillus acidophilus* NCFM) using a primer set for discriminating a *L. acidophilus* strain of the present disclosure and conducting agarose gel electrophoresis.

Figure 19:
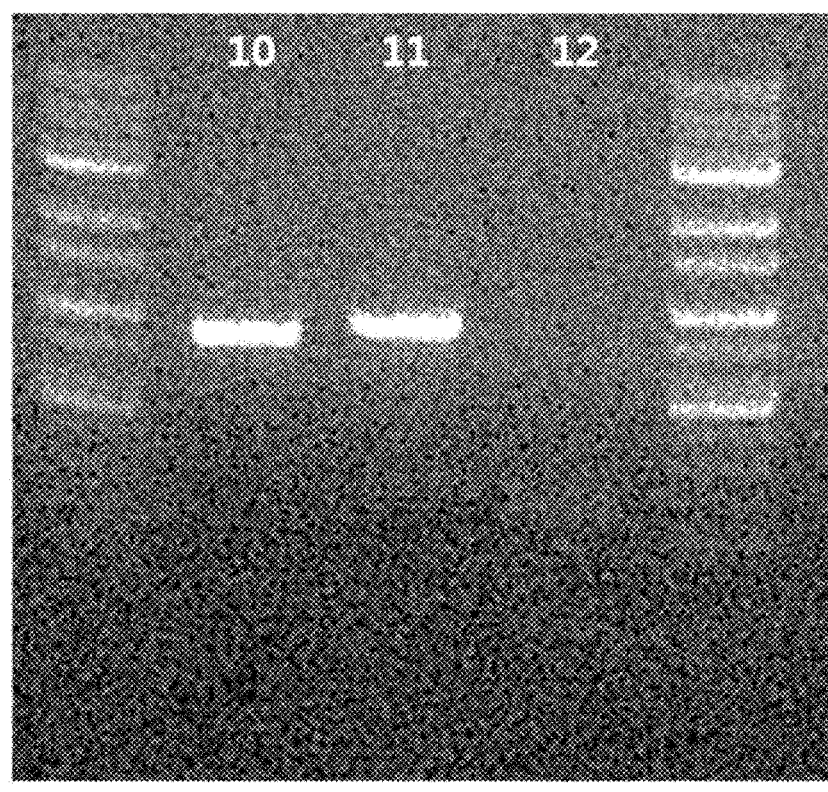

FIG. 19 shows a result of purifying a PCR amplification product obtained by performing PCR for different strains (*Lactobacillus acidophilus* LA1, *Lactobacillus acidophilus* ATCC 4356 and *Lactobacillus acidophilus* NCFM) using a primer set for discriminating a *L. acidophilus* strain of the present disclosure and then analyzing the same by agarose gel electrophoresis.

FIG. 20 shows a result of performing PCR for different strains (*Lactobacillus helveticus* ATCC 13866, *Lactobacillus amylovorus* ATCC 33620, *Lactobacillus acidophilus* ATCC 4356, *Lactobacillus acidophilus* NCFM, *Lactobacillus acidophilus* LA1 and *Lactobacillus acidophilus* YT1) using a primer set for discriminating a *Lactobacillus acidophilus* YT1 strain of the present disclosure.

Figure 21:
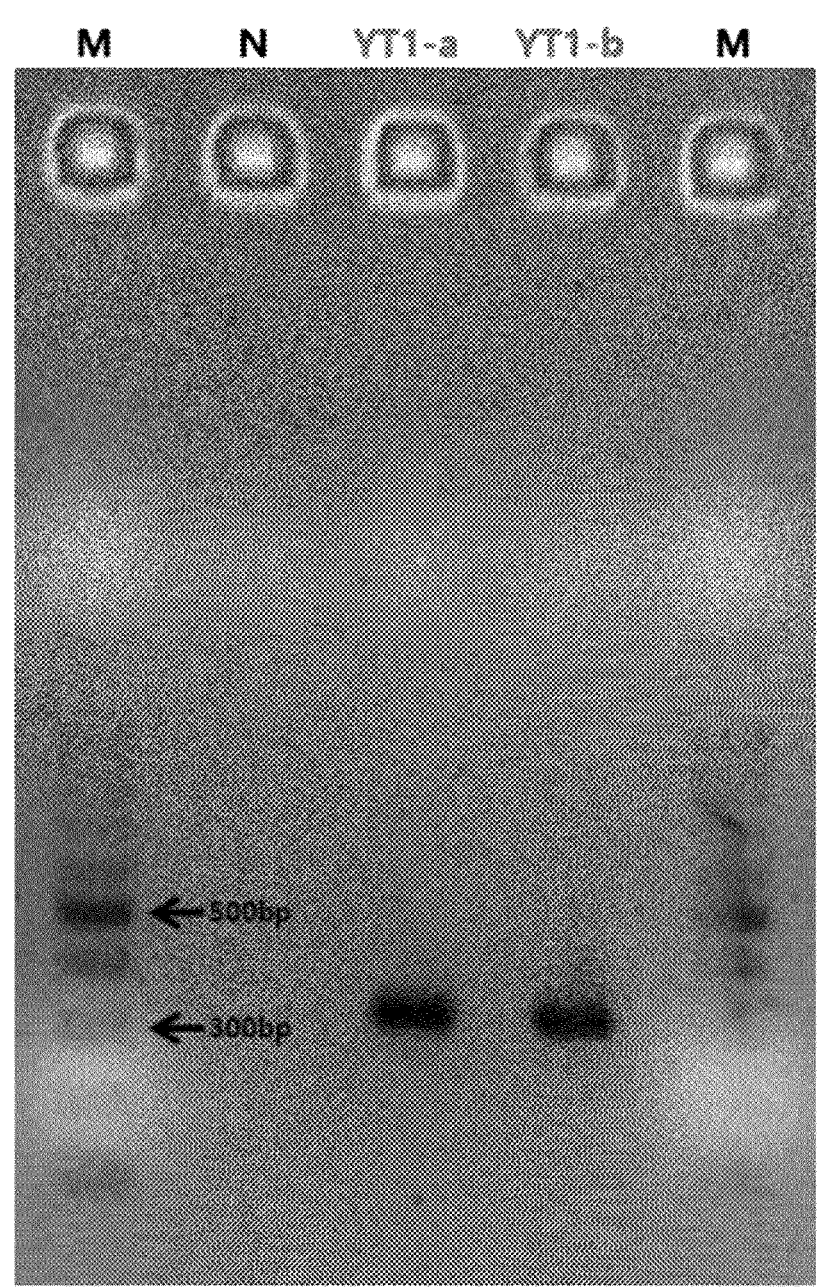

FIG. 21 shows a result of purifying a PCR amplification product obtained by performing PCR for a *Lactobacillus acidophilus* YT1 strain using a primer set for discriminating a *Lactobacillus acidophilus* YT1 strain of the present disclosure and analyzing the same by agarose gel electrophoresis. A representative result of 10 repeated experiments is shown.

BEST MODE

Hereinafter, various aspects and exemplary embodiments of the present disclosure will be described more specifically.

In the present disclosure, a primer refers to a short nucleic acid sequence having a short free 3' hydroxyl group, wherein the nucleic acid sequence can form base pairs with a complementary template and acts as a starting point for replication of the nucleic acid template. The primer may initiate DNA synthesis in the presence of a reagent for polymerization (i.e., DNA polymerase) under the condition of an appropriate buffer and temperature.

In the present disclosure, a primer set refers to a combination of primers for amplifying a specific sequence DNA. One primer set usually includes two primers (a forward primer and a reverse primer, or a left primer and a right primer) but may also include more than two primers.

In the present disclosure, an oligonucleotide refers to a single-stranded or double-stranded deoxyribooligonucleotide or ribooligonucleotide, and includes an analogue of a natural nucleotide unless specially mentioned otherwise.

In an aspect, the present disclosure relates to a primer composition for discriminating the species *Lactobacillus acidophilus*, which includes a primer set consisting of one or more forward primer selected from SEQ ID NOS: 1-8 and one or more reverse primer selected from SEQ ID NOS: 9-16.

In another aspect, the present disclosure relates to a use of a primer set consisting of one or more forward primer selected from SEQ ID NOS: 1-8 and one or more reverse primer selected from SEQ ID NOS: 9-16 for detecting a *Lactobacillus acidophilus* strain.

The primer composition includes a primer set consisting of primers selected from SEQ ID NOS: 1-8 and SEQ ID NOS: 9-16, which is capable of specifically detecting a strain belonging to the species *Lactobacillus acidophilus*.

Specifically, the primer set may be one or more selected from a primer set consisting of SEQ ID NOS: 1 and 9, a primer set consisting of SEQ ID NOS: 2 and 10, a primer set consisting of SEQ ID NOS: 3 and 11, a primer set consisting of SEQ ID NOS: 4 and 12, a primer set consisting of SEQ ID NOS: 5 and 13, a primer set consisting of SEQ ID NOS: 6 and 14, a primer set consisting of SEQ ID NOS: 7 and 15, and a primer set consisting of SEQ ID NOS: 8 and 16.

The primer composition of the present disclosure may include a primer set capable of specifically detecting a strain of the species *Lactobacillus acidophilus* even in a sample in which strains similar to the species *Lactobacillus acidophilus* or strains belonging to the same species or genus are mixed.

As confirmed in the test examples described below, the primer composition of the present disclosure synthesizes a PCR product using the 'CRISPR' region gene of the species *Lactobacillus acidophilus* as a template and does not synthesize a PCR product for strains other than the species *Lactobacillus acidophilus*. Therefore, the presence of a strain of the species *Lactobacillus acidophilus* in a sample can be discriminated specifically using the primer composition.

The species *Lactobacillus acidophilus* can be identified specifically by using the primer composition. For example, when a primer composition including a forward primer represented by SEQ ID NO: 1 and a reverse primer represented by SEQ ID NO: 9 is used, a PCR product with a size of 100-300 bp, specifically 267 bp, is detected if a strain of the species *Lactobacillus acidophilus* is present in the sample. Accordingly, the presence of the species *Lactobacillus acidophilus* can be discriminated specifically based on the detection of a PCR product by each primer composition and the size of the PCR product. It synthesizes a PCR product on when a 'CRISPR' region gene of the species *Lactobacillus acidophilus* is present in the target of detection or diagnosis by using the same as a template.

For the primer composition including a forward primer represented by SEQ ID NO: 1 and a reverse primer represented by SEQ ID NO: 9, a PCR product with a size of 100-400 bp, specifically 267 bp, is detected for a strain belonging to the species *Lactobacillus acidophilus*.

That is to say, the primer composition of the present disclosure is capable of specifically discriminating a specific species (*acidophilus*) from the genus *Lactobacillus*.

The primers included in the primer composition of the present disclosure may have a length of 20-30 bp. Specifically, the forward primers represented by SEQ ID NOS: 1-8 may have a length of 24-26 bp, and the reverse primers represented by SEQ ID NOS: 9-16 may have a length of 20-22 bp. A target sequence may be amplified by performing amplification reaction using a primer set including the primers. Specifically, melting temperature ($T_m$) may be 55-65° C., the maximum difference in $T_m$ between primers may be 3-5° C., and GC % may be 30-70%.

Specifically, the primer composition may be a primer set consisting of one or more forward primer selected from SEQ ID NOS: 1-6 and one or more reverse primer selected from SEQ ID NOS: 9-14, which is a universal primer set capable of specifically discriminating, identifying and detecting all the species of *Lactobacillus acidophilus*.

Methods for amplifying the target sequence include polymerase chain reaction (PCR), ligase chain reaction, nucleic acid sequence-based amplification, transcription-based amplification, strand displacement amplification, Q5 replicase amplification, or other suitable methods for amplification of nucleic acid molecules well known in the art. Among them, PCR is a method of amplifying a target nucleic acid from a primer pair binding specifically to the target nucleic acid using a polymerase. The PCR method is well known in the art, and a commercially available kit may also be used.

In a specific example of the present disclosure, it was confirmed that, among the primer sets, a primer set including one or more forward primer selected from SEQ ID NOS: 1-8 and one or more reverse primer selected from SEQ ID NOS: 9-16 synthesizes PCR products for the strains of *Lactobacillus acidophilus* belonging to the same genus and species, whereas it never synthesizes PCR products for the strain belonging to different genus and species (*Lactobacillus helveticus* ATCC 13866 and *Lactobacillus* amylovorus ATCC 33620) under the same conditions of annealing temperature and time. In particular, it was confirmed that the primer sets including one or more forward primer selected from SEQ ID NOS: 1-6 and one or more reverse primer selected from SEQ ID NOS: 9-14 synthesize the same PCR products for the species *Lactobacillus acidophilus*.

Through this, it can be seen that the time and effort required for discrimination of the presence of a strain of the species *Lactobacillus acidophilus* in a sample can be saved.

The primer composition may further include one or more label selected from a group consisting of a fluorophore, a chromophore, a chemiluminophore, a magnetic particle and a radioisotope, which is linked to the 5'-end or 3'-end of the forward primer or the reverse primer.

The "label" or "detectable label" may refer to any chemical moiety bonded to a nucleotide, a nucleotide polymer or a nucleic acid-binding factor, and the bonding may be covalent or non-covalent bonding. Specifically, the label is detectable and renders the nucleotide or the nucleotide polymer to be detected by a practitioner of the present disclosure. Detectable labels include luminescent molecules, chemiluminescent molecules, fluorochromes, fluorescent quenching agents, colored molecules, radioisotopes or scintillants. The detectable labels also include any useful linker molecules (e.g., biotin, avidin, streptavidin, HRP, protein A, protein G, antibodies or fragments thereof, Grb2, polyhistidine, $Ni^{2+}$, FLAG tag and myc tag), heavy metals, enzymes (e.g., alkaline phosphatase, peroxidase and luciferase), electron donors/acceptors, acridinium esters, dyes and calorimetric substrates. In addition, the change in mass may be considered as a detectable label as in surface plasmon resonance detection. Those skilled in the art would readily recognize useful detectable labels that are not mentioned above, which may be used in the exemplary embodiments of the present disclosure.

In another aspect, the present disclosure relates to a primer composition for discriminating individual *Lactobacillus acidophilus* strains, which includes a primer set consisting of a forward primer represented by SEQ ID NO: 8 and a reverse primer represented by SEQ ID NO: 16.

Specifically, among the primer compositions, a primer set consisting of a forward primer represented by SEQ ID NO: 8 and a reverse primer represented by SEQ ID NO: 16 can discriminate and distinguish individual *Lactobacillus acidophilus* strains based on the size of the PCR product. For example, it can specifically identify *Lactobacillus acidophilus* ATCC 4356, *Lactobacillus acidophilus* NCFM and *Lactobacillus acidophilus* LA1 strains.

In addition, the primer composition may further include a primer set consisting of a forward primer represented by SEQ ID NO: 7 and a reverse primer represented by SEQ ID NO: 15 in order to clearly discriminate and distinguish a *Lactobacillus acidophilus* YT1 strain.

Specifically, if a PCR product with a size of about 100-1000 bp is detected after performing PCR using the primer set, the corresponding strain belongs to the species *Lactobacillus acidophilus*, specifically *Lactobacillus acidophilus* ATCC 4356, *Lactobacillus acidophilus* NCFM or *Lactobacillus acidophilus* LA1 strain.

When the composition is used, *Lactobacillus acidophilus* ATCC 4356, *Lactobacillus acidophilus* NCFM and *Lactobacillus acidophilus* LA1 strains may be identified specifically. The presence of the *Lactobacillus acidophilus* strain may be discriminated specifically based on the detection of a PCR product with a size of about 100-1000 bp. When only the 'CRISPR' region gene of the *Lactobacillus acidophilus* strain which is the target of detection or diagnosis is present, the PCR product is synthesized using the same as a template and a PCR product with a size of 100-1000 bp is detected.

The PCR product of the *Lactobacillus acidophilus* LA1 strain has a size of about 100-250 bp, differently from the PCR products of the strains of other species in the same genus. Since the difference in size is 750 bp at the maximum from other species in the same genus, the presence of the *Lactobacillus acidophilus* LA1 strain in the sample can be clearly discriminated specifically using the composition.

In other words, the target for DNA amplification is the "gene sequence of the CRISPR region" of the *Lactobacillus acidophilus* strain, and the *Lactobacillus acidophilus* strain may include various strains such as *L. acidophilus* ATCC 4356, *L. acidophilus* NCFM, *L. acidophilus* La-14, *L. acidophilus* FSI4 and *L. acidophilus* LA1, although not being specially limited thereto.

Figure 6:
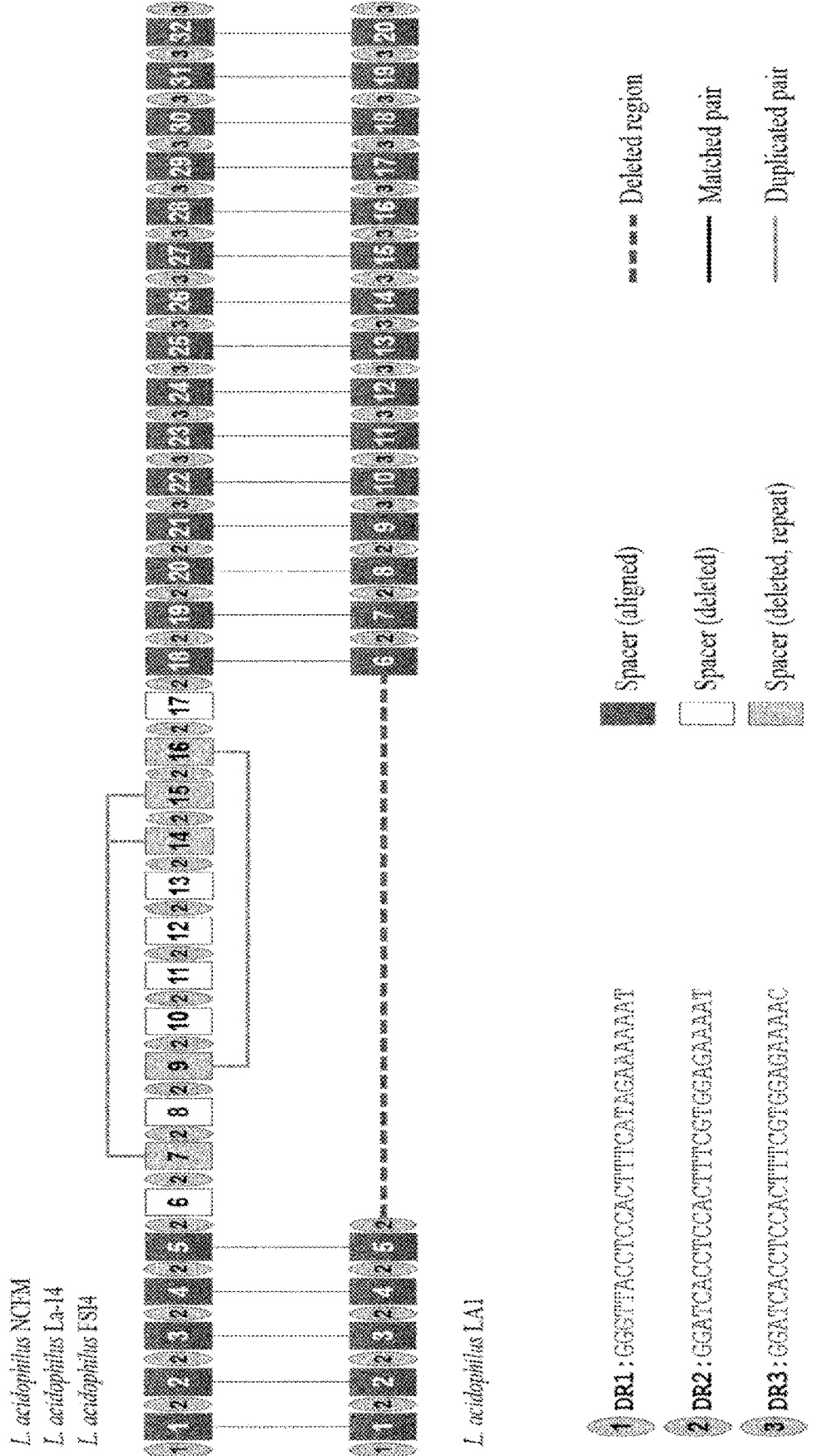
FIG. 6 shows a CRISPR structure analysis result for *Lactobacillus acidophilus* NCFM, *Lactobacillus acidophilus* La-14, *Lactobacillus acidophilus* FSI4 and *Lactobacillus acidophilus* LA1 from among 10 sp. strains including *Lactobacillus acidophilus* LA1 confirmed in Example 4.
Figure 7:
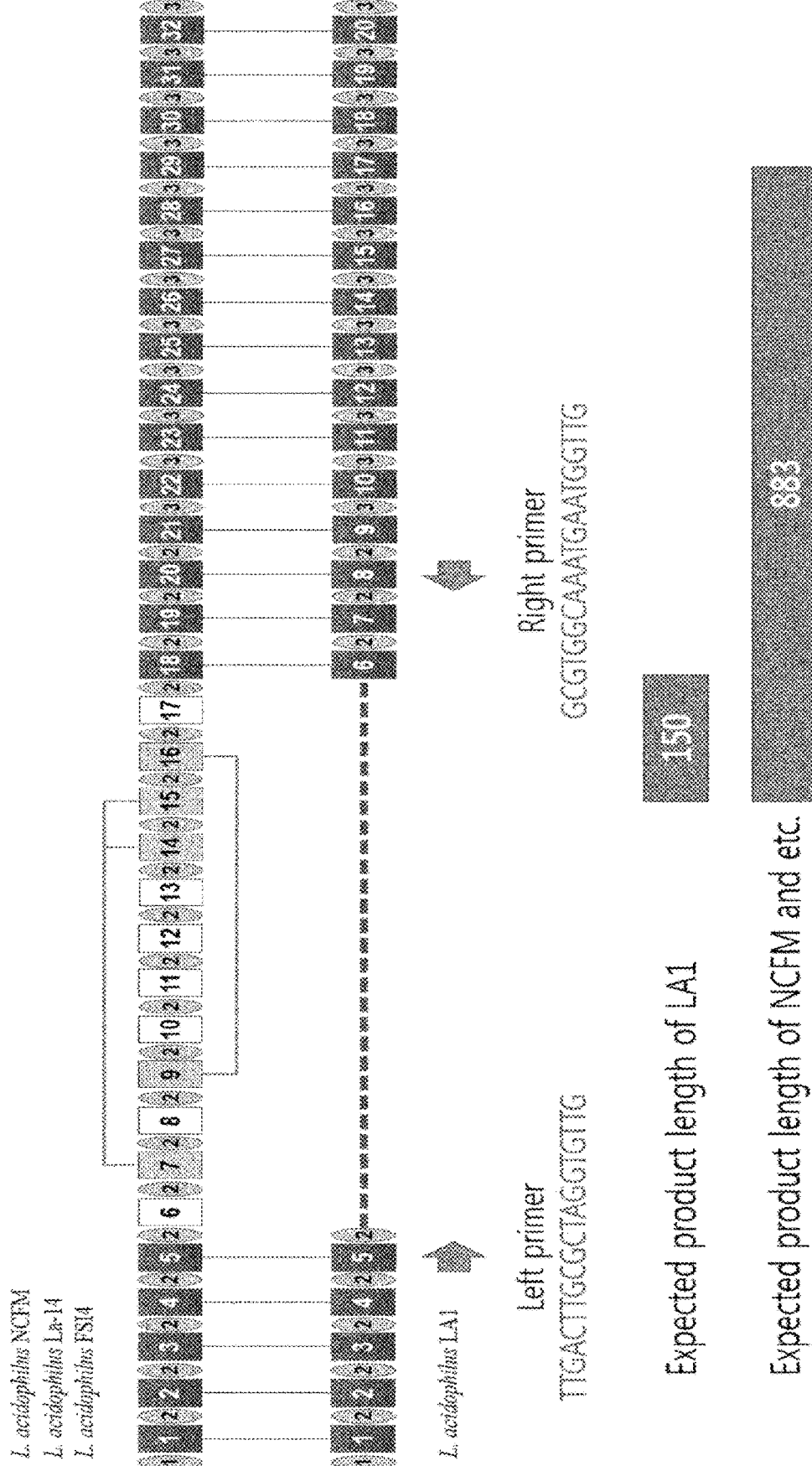
FIG. 7 shows a primer set capable of specifically detecting *Lactobacillus acidophilus* LA1 and the size of the PCR product of each strain obtained using the primer set, analyzed by in silico analysis.

The "gene sequence of the CRISPR region" which is exemplified as a target for amplification according to the present disclosure is schematically shown in FIGS. 6 and 7. An exemplary nucleotide sequence of the whole genome of *Lactobacillus acidophilus* LA1 can be found in Genbank Accession No. NZ_CP017062 and exemplary nucleotide sequences of the whole genomes of the CRISPR regions of *L. acidophilus* NCFM, *L. acidophilus* La-14 and *L. acidophilus* FSI4 can be found in Genbank Accession Nos. NC_006814.3, NC_021181.2 and NZ_CP010432.1, respectively.

In general, the primer set included in the composition of the present disclosure has a total primer length of 18-23 bp (optimal length: 20 bp), a melting temperature ($T_m$) of 57-62° C., the maximum difference in $T_m$ between primers of 5° C. or smaller, and GC % of 35-65%.

In a specific example of the present disclosure, it was confirmed that the primer set including a forward primer represented by SEQ ID NO: 8 and a reverse primer represented by SEQ ID NO: 16 of the present disclosure synthesizes PCR products with different sizes of 165 bp, 837 bp, 898 bp, 900 bp and 1000 bp for the *Lactobacillus acidophilus* strains of the same genus and species under the same annealing temperature and time condition, but it synthesizes no PCR product at all for the strains of different species of the same genus (*Lactobacillus helveticus* ATCC 13866 and *Lactobacillus* amylovorus ATCC 33620). Through this, it can be seen that the present disclosure enables accurate detection and discrimination of the *Lactobacillus acidophilus* strain from among many strains of the same genus present in a sample and allows discrimination of *Lactobacillus acidophilus* ATCC 4356, *Lactobacillus acidophilus* NCFM and *Lactobacillus acidophilus* LA1 strains in a sample based on the size of the PCR product, and that the time and efforts required for discrimination of *Lactobacillus acidophilus* strains can be saved.

In particular, since the PCR product of the *Lactobacillus acidophilus* LA1 strain synthesized by the primer set including a forward primer represented by SEQ ID NO: 8 and a reverse primer represented by SEQ ID NO: 16 of the present disclosure has a size of 150-250 bp, which is clearly distinguished from that of other *Lactobacillus acidophilus* strains, the presence of the *Lactobacillus acidophilus* LA1 strain in a sample can be specifically discriminated using the composition.

The PCR product of the *Lactobacillus acidophilus* LA1 strain has a size of about 150-250 bp, specifically 150-200 bp, which is significantly different from the PCR product size of other strains of the same species in the same genus, and thus can detect, distinguish and discriminate the *Lactobacillus acidophilus* LA1 strain specifically by analyzing the size of PCR products. Accordingly, the time and efforts required for discriminating the presence of the *Lactobacillus acidophilus* LA1 strain in a sample can be saved.

The primer composition may further include one or more label selected from a group consisting of a fluorophore, a chromophore, a chemiluminophore, a magnetic particle and a radioisotope, which is linked to the 5'-end or 3'-end of the forward primer or the reverse primer.

The "label" or "detectable label" may refer to any chemical moiety bonded to a nucleotide, a nucleotide polymer or a nucleic acid-binding factor, and the bonding may be covalent or non-covalent bonding. Specifically, the label is detectable and renders the nucleotide or the nucleotide polymer to be detected by a practitioner of the present disclosure. Detectable labels include luminescent molecules, chemiluminescent molecules, fluorochromes, fluorescent quenching agents, colored molecules, radioisotopes or scintillants. The detectable labels also include any useful linker molecules (e.g., biotin, avidin, streptavidin, HRP, protein A, protein G, antibodies or fragments thereof, Grb2, polyhistidine, $Ni^{2+}$, FLAG tag and myc tag), heavy metals, enzymes (e.g., alkaline phosphatase, peroxidase and luciferase), electron donors/acceptors, acridinium esters, dyes and calorimetric substrates. In addition, the change in mass may be considered as a detectable label as in surface plasmon resonance detection. Those skilled in the art would readily recognize useful detectable labels that are not mentioned above, which may be used in the exemplary embodiments of the present disclosure.

In another aspect, the present disclosure relates to a primer composition for discriminating a *Lactobacillus acidophilus* YT1 strain, which includes a primer set consisting of a forward primer represented by SEQ ID NO: 7 and a reverse primer represented by SEQ ID NO: 15.

Specifically, the primer set consisting of a forward primer represented by SEQ ID NO: 7 and a reverse primer represented by SEQ ID NO: 15 can specifically discriminate the *Lactobacillus acidophilus* YT1 strain from the species *Lactobacillus acidophilus*.

The *Lactobacillus acidophilus* YT1 strain has a genomic structural characteristic that it has two CRISPR regions. All the known strains of the species *Lactobacillus acidophilus* other than *Lactobacillus acidophilus* YT1 have one CRISPR region. Based on this difference, a specific primer set capable of identifying a sequence at an entirely different location from the previously known *Lactobacillus acidophilus* strains and amplifying the same was designed, and the distinct difference in the length of the amplified product was confirmed.

A primer composition including the primer set (SEQ ID NOS: 7 and 15) can specifically detect the *Lactobacillus acidophilus* YT1 strain from a sample wherein strains similar to the *Lactobacillus acidophilus* YT1 strain or strain of the same species and genus are mixed.

As confirmed in the test examples described below, because the composition synthesizes no PCR product for *Lactobacillus* strains and *Lactobacillus acidophilus* strains other than the *Lactobacillus acidophilus* YT1 strain and synthesizes a PCR product only when the 'CRISPR' region gene of the *Lactobacillus acidophilus* YT1 strain is present by using the same as a template, the presence of the *Lactobacillus acidophilus* YT1 strain can be discriminated specifically from a sample by using the composition.

The primer set (SEQ ID NOS: 7 and 15) can specifically identify the *Lactobacillus acidophilus* YT1 strain and can specifically discriminate the presence of the *Lactobacillus acidophilus* YT1 strain based on the detection of a PCR product with a size of 300-350 bp, specifically 320 bp. Since the primer set synthesizes a PCR product only when the 'CRISPR' region gene of the *Lactobacillus acidophilus* YT1 strain, which is a target of detection or diagnosis, is present by using the same as a template, only the *Lactobacillus acidophilus* YT1 strain with a size of 300-350 bp, specifically 320 bp, is detected as a PCR product.

The *Lactobacillus acidophilus* YT1 strain (accession number KCCM11808P), which is a target of the composition of the present disclosure, is a strain disclosed in Korean Patent Publication No. 10-2018-0052569. It is the strain which exhibits the largest difference from among the microorganisms with the distribution of which is decreased in an ovariectomized menopausal animal model, and has been confirmed to have the effect of preventing or therapeutic depression in menopausal women.

Figure 10:
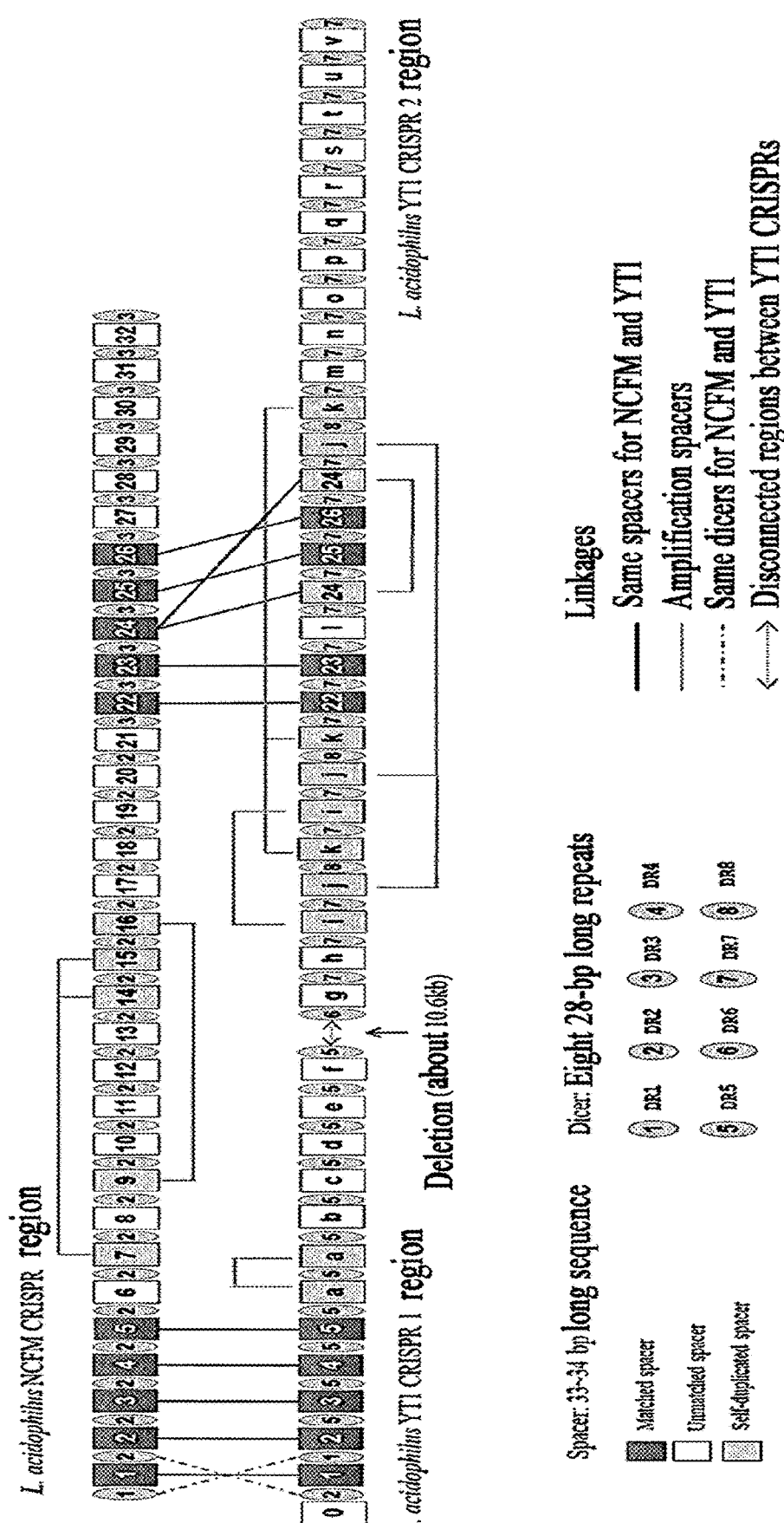
FIG. 10 shows a CRISPR structure analysis result for the reference strains *Lactobacillus acidophilus* NCFM and *Lactobacillus acidophilus* YT1 from among 22 sp. strains including *Lactobacillus acidophilus* YT1 confirmed in Example 7.

The "gene sequence of the CRISPR region", which is an exemplary target for amplification according to the present disclosure, is schematically shown in FIGS. 10 and 11. An exemplary nucleotide sequence of the whole genome of *Lactobacillus acidophilus* YT1 can be found in Genbank Accession No. CP025200.1. Meanwhile, the whole genome nucleotide sequence of the CRISPR region of the *Lactobacillus acidophilus* NCFM strain, which is used as a control group for analysis of the specificity of the composition of the present disclosure, can be found in Genbank Accession No. NC_006814.3. The whole genome nucleotide sequences of other strains for comparison can also be found in the Genbank database.

The primer set included in the composition of the present disclosure has an optimal primer length of 20 bp, a melting temperature ($T_m$) of 60° C., the maximum difference in $T_m$ between primers of 5° C. or smaller, and GC % of 50%.

In a specific example of the present disclosure, it was confirmed that the primer set including a forward primer represented by SEQ ID NO: 7 and a reverse primer represented by SEQ ID NO: 15 of the present disclosure synthesizes no PCR product at all for the *Lactobacillus acidophilus* strains of the same genus and species under the same annealing temperature and time but synthesizes a 320-bp PCR product only for the *Lactobacillus acidophilus* YT1 strain. Through this, it can be seen that the time and efforts required for discriminating the presence of the *Lactobacillus acidophilus* strain in a sample can be saved remarkably since only the *Lactobacillus acidophilus* YT1 strain can be detected and discriminated specifically and clearly even when strains belonging to the same genus are present in the sample.

The primer composition may further include one or more label selected from a group consisting of a fluorophore, a chromophore, a chemiluminophore, a magnetic particle and a radioisotope, which is linked to the 5'-end or 3'-end of the forward primer or the reverse primer.

The "label" or "detectable label" may refer to any chemical moiety bonded to a nucleotide, a nucleotide polymer or a nucleic acid-binding factor, and the bonding may be covalent or non-covalent bonding. Specifically, the label is detectable and renders the nucleotide or the nucleotide polymer to be detected by a practitioner of the present disclosure. Detectable labels include luminescent molecules, chemiluminescent molecules, fluorochromes, fluorescent quenching agents, colored molecules, radioisotopes or scintillants. The detectable labels also include any useful linker molecules (e.g., biotin, avidin, streptavidin, HRP, protein A, protein G, antibodies or fragments thereof, Grb2, polyhistidine, $Ni^{2+}$, FLAG tag and myc tag), heavy metals, enzymes (e.g., alkaline phosphatase, peroxidase and luciferase), electron donors/acceptors, acridinium esters, dyes and calorimetric substrates. In addition, the change in mass may be considered as a detectable label as in surface plasmon resonance detection. Those skilled in the art would readily recognize useful detectable labels that are not mentioned above, which may be used in the exemplary embodiments of the present disclosure.

In another aspect, the present disclosure relates to a kit for discriminating the species *Lactobacillus acidophilus*, which includes the primer composition.

The kit may be used for discrimination of the species *Lactobacillus acidophilus*, discrimination of individual *Lactobacillus acidophilus* strains or discrimination of the *Lactobacillus acidophilus* YT1 strain depending on the primer set included in the primer composition.

The kit may further include a reagent for performing amplification reactions. For example, it may further include a buffer, a DNA polymerase, a dNTP, distilled water, etc., and a solution, an enzyme, etc. commonly used in the art may be used without limitation. In addition, the kit may be prepared as a plurality of packages or compartments including the reagent.

The buffer is a compound which is added to an amplification reaction to change the stability, activity and/or lifetime of one or more elements of the amplification reaction. The buffer of the present disclosure may be compatible with PCR amplification and RNase H cleavage activities. Specifically, the buffer includes HEPES (4-(2-hydroxyethyl)-1-piperazineethanesulfonic acid), MOPS (3-(N-morpholino)

propanesulfonic acid), an acetate buffer, a phosphate buffer, etc., although not being limited thereto. In addition, a PCR buffer may generally contain about 70 mM or lower of KCl, about 1.5 mM or more of $MgCl_2$, and about 50-200 UM of dATPs, dCTPs, dGTPs and dTTPs. The buffer of the present disclosure may include an additive for effective reverse transcriptase PCR or for optimized PCR reaction.

The additive affects the inactivation of contaminated enzymes, stabilization of protein folding and/or reduction of aggregation. Examples of the additive that may be used in amplification reaction include betaine, formamide, KCl, $CaCl_2$), MgOAc, $MgCl_2$, NaCl, $NH_4OAc$, NaI, $Na(CO_3)_2$, LiCl, MnOAc, NMP, trehalose, dimethyl sulfoxide (DMSO), glycerol, ethylene glycol, dithiothreitol (DTT), pyrophosphatase (including but not limited to Thermoplasma *acidophilum* inorganic pyrophosphatase, TAP), bovine serum albumin (BSA), propylene glycol, glycinamide, CHES, Percoll, aurintricarboxylic acid, Tween 20, Tween 21, Tween 40, Tween 60, Tween 85, Brij 30, NP-40, Triton X-100, CHAPS, CHAPSO, Mackernium, LDAO (N-dodecyl-N,N-dimethylamine-N-oxide), Zwittergent 3-10, Zwittergent 3-14, Zwittergent SB 3-16, Empigen, NDSB-20, T4G32, *E. Coli* SSB, RecA, nicking endonucleases, 7-diazaG, dUTPs, anionic detergents, cationic detergents, nonionic detergents, Zwittergent, sterol, osmolytes, cations, and other compounds, proteins or cofactors capable of changing the efficiency of amplification, although not being limited thereto. In a specific exemplary embodiment, two or more additives may be used in the amplification reaction. As long as the additive does not interfere with the activity of RNase H, the additive may be added selectively for improving the selectivity of primer annealing.

The inventors of the present disclosure have developed a primer set (a forward primer and a reverse primer, or a left primer and a right primer) targeting the CRISPR region gene of the species *Lactobacillus acidophilus* from among the microorganisms present in a sample, and have developed a method capable of not only accurately detecting the presence of the species *Lactobacillus acidophilus* but also accurately and quickly specifying, discriminating and distinguishing a specific strain by comparing and analyzing the presence and length of the base sequences of the amplified CRISPR region. A primer set consisting of one or more forward primer selected from SEQ ID NOS: 1-8 and one or more reverse primer selected from SEQ ID NOS: 9-16 can amplify the CRISPR gene of *Lactobacillus acidophilus*. Especially, a primer set consisting of one or more forward primer selected from SEQ ID NOS: 1-6 and one or more reverse primer selected from SEQ ID NOS: 9-14 can universally discriminate the species *Lactobacillus acidophilus* using a primer which amplifies one or more region selected from the regions of spacers 1 to 5, which are shared by all the strains of the species *Lactobacillus acidophilus*. It was confirmed that, when the primer composition of SEQ ID NO: 1 and SEQ ID NO: 9 was used for actual PCR analysis, the strain of the species *Lactobacillus acidophilus* was found to show a PCR product with a size of 100-400 bp, specifically 267 bp. Since it corresponds to the sum of 223 bp of the PCR product for the CRISPR region of the *Lactobacillus acidophilus* sp. strain (spacers 1-5), which is amplified with the primer set, and the sequence of the primer set of SEQ ID NOS: 1 and 9 (44 bp), it can be discriminate that the strain exhibiting a PCR product with a size of 267 bp belongs to the species *Lactobacillus acidophilus*.

Since the primer composition produces PCR products only for the strains belonging to the species *Lactobacillus acidophilus* (e.g., a PCR product of 200-300 bp, specifically 267 bp, for the primer composition of SEQ ID NOS: 1 and 9) and does not produce PCR products for other strains, it allows clear and distinct identification of the strain without sequencing of the PCR product.

In addition, the inventors of the present disclosure have confirmed that, since the sequence length of the CRISPR region gene of the *Lactobacillus acidophilus* LA1 strain is 165 bp (150 bp+8 bp primer+7 bp dicer) unlike other strains, the *Lactobacillus acidophilus* LA1 strain can be discriminated based thereon. Among the primer sets designed based on this, a primer set consisting of SEQ ID NO: 8 and SEQ ID NO: 16 could discriminate the *Lactobacillus acidophilus* ATCC 4356, *Lactobacillus acidophilus* NCFM and *Lactobacillus acidophilus* LA1 strains among the species *Lactobacillus acidophilus* based on the PCR product size. In addition, the *Lactobacillus acidophilus* YT1 could be distinguished when a primer set consisting of SEQ ID NO: 7 and SEQ ID NO: 15 was used in combination.

Specifically, when a PCR product with a size of about 150-200 bp was detected when a primer set consisting of SEQ ID NO: 8 and SEQ ID NO: 16 was used, the corresponding strain may be identified as the *Lactobacillus acidophilus* LA1 strain. Because the 165 bp PCR product (150 bp+8 bp primer+7 bp dicer) for the CRISPR region of the *Lactobacillus acidophilus* LA1 strain amplified with the primer set includes the primer set sequence (40 bp) of SEQ ID NOS: 8 and 16, a PCR product with a size of 150-250 bp may be discriminated as the *Lactobacillus acidophilus* LA1 strain. Other *Lactobacillus acidophilus* strains are clearly and distinctly distinguishable because the PCR product has a size of 800-1500 bp, specifically 800-1000 bp, unlike the *Lactobacillus acidophilus* LA1 strain.

In addition, the inventors of the present disclosure have identified that, among the amplified CRISPR region genes, only the *Lactobacillus acidophilus* YT1 strain has a size of 320 bp and have developed a primer set of SEQ ID NO: 7 and SEQ ID NO: 15, which is capable of discriminating the *Lactobacillus acidophilus* YT1 strain based thereon. Since the 165 bp PCR product (150 bp+8 bp primer+7 bp dicer) for the CRISPR region of the *Lactobacillus acidophilus* YT1 strain amplified with the primer set includes the primer set sequence (40 bp) of SEQ ID NOS: 7 and 15, a PCR product with a size of 320 bp may be discriminated as the *Lactobacillus acidophilus* YT1 strain. Other *Lactobacillus acidophilus* strains are clearly and distinctly distinguishable because they do not produce a PCR product unlike the *Lactobacillus acidophilus* YT1 strain.

In another aspect, the present disclosure relates to a method for discriminating the species *Lactobacillus acidophilus* using the primer composition, which includes: a) a step of obtaining a PCR product through polymerase chain reaction (PCR) by using a DNA isolated from a target sample to be discriminated as a template and using a primer set consisting of one or more forward primer selected from SEQ ID NOS: 1-8 and one or more reverse primer selected from SEQ ID NOS: 9-16; and b) a step of identifying the presence of the PCR product.

In another aspect, the present disclosure relates to method for detecting the presence of a *Lactobacillus acidophilus* strain in a clinical, environmental or food sample, which includes: i) a step of performing polymerase chain reaction (PCR) by using a primer set consisting of one or more forward primer selected from SEQ ID NOS: 1-8 and one or more reverse primer selected from SEQ ID NOS: 9-16; and ii) a step of identifying the formation of a PCR product.

First, a PCR product is obtained by performing polymerase chain reaction (PCR) by using the DNA isolated from a target sample to be discriminated as a template and using a primer set consisting of one or more forward primer selected from SEQ ID NOS: 1-8 and one or more reverse primer selected from SEQ ID NOS: 9-16.

The DNA may be isolated from the sample using a method known in the art. The DNA may be extracted specifically by alkaline extraction, hot water extraction, column extraction or phenol/chloroform extraction, more specifically by alkaline extraction.

The target sample to be discriminated may include various samples wherein the presence of a strain belonging to the species *Lactobacillus acidophilus* is desired to be detected. Specifically, it may be a clinical, environmental or food sample.

When the primer is designed and the DNA is prepared from the target sample to be discriminated as described above, DNA amplification may be performed by various methods including polymerase chain reaction (PCR), nucleic acid sequence-based amplification (NASBA), ligase chain reaction (LCR) and rolling circle amplification (RCA). However, polymerase chain reaction (PCR) is the most general and desired method of amplifying a specific target DNA sequence.

And, the PCR may be real-time PCR, qRT-PCR or RT-PCR, although not being limited thereto.

In the present disclosure, "polymerase chain reaction" or "PCR" generally refers to a method of amplifying a desired target sequence in vitro, and is not specially limited as long as it is a process commonly used in the art. For example, the PCR process includes a step of adding an excess amount (2 molar equivalents or more) of oligonucleotide primers complementary to the double-stranded target sequence to a reaction mixture containing the desired target sequence(s). The reaction mixture is subjected to thermal cycling in the presence of a DNA polymerase, so that the desired target sequence is amplified between the DNA primer set.

A PCR product obtained through the above process is also called a "PCR fragment", a "reverse transcriptase PCR fragment" or an "amplicon", and refers to a polynucleotide molecule (or molecules) produced from amplification of a specific target nucleic acid. The PCR fragment generally refers to a DNA PCR fragment, although not being limited thereto. The PCR fragment may be a single-stranded fragment, a double-stranded fragment or a mixture thereof at any ratios. The PCR fragment or the reverse transcriptase PCR fragment may be 100-500 nucleotides or longer.

The presence of the species *Lactobacillus acidophilus* may be identified and discriminated by analyzing the amplified PCR product. The analysis may be performed by analyzing the base sequence of the PCR product or the size of the amplification product (e.g., for a primer composition of SEQ ID NOS: 1 and 9, the size of the PCR product is identified to be 100-400 bp, specifically 260-280 bp, most specifically 267 bp).

In the present disclosure, the presence of a strain belonging to the species *Lactobacillus acidophilus* may be identified or detected by analyzing the amplified PCR product and it may be determined whether an unknown strain belongs to the species *Lactobacillus acidophilus*.

That is to say, the information about the PCR product appearing specifically in the species *Lactobacillus acidophilus* may be acquired and the species *Lactobacillus acidophilus* may be specifically discriminated and analyzed quickly with high reliability.

When a PCR product with a size of 100-400 bp is observed, it can be clearly discriminated that a strain belonging to the species *Lactobacillus acidophilus* is present in the sample.

Specifically, if a strain belonging to the species *Lactobacillus acidophilus* is present in a sample, a 267 bp PCR product is observed when a forward primer of SEQ ID NO: 1 and a reverse primer of SEQ ID NO: 9 are used, a 208 bp PCR product is observed when a forward primer of SEQ ID NO: 2 and a reverse primer of SEQ ID NO: 10 are used, a 147 bp PCR product is observed when a forward primer of SEQ ID NO: 3 and a reverse primer of SEQ ID NO: 11 are used, a 207 bp PCR product is observed when a forward primer of SEQ ID NO: 4 and a reverse primer of SEQ ID NO: 12 are used, a 148 bp PCR product is observed when a forward primer of SEQ ID NO: 5 and a reverse primer of SEQ ID NO: 13 are used, and a 146 bp PCR product is observed when a forward primer of SEQ ID NO: 6 and a reverse primer of SEQ ID NO: 14 are used. In addition, a 300-350 bp, specifically 320 bp, PCR product is observed when a forward primer of SEQ ID NO: 7 and a reverse primer of SEQ ID NO: 15 are used. Through this, the presence of a strain belonging to the species *Lactobacillus acidophilus*, especially the presence of the *Lactobacillus acidophilus* YT1 strain, may be detected or discriminated.

In addition, a 150-250 bp, specifically 150-200 bp, PCR product is observed when a forward primer of SEQ ID NO: 8 and a reverse primer of SEQ ID NO: 16 are used. In this case, the presence of the *Lactobacillus acidophilus* LA1 strain in a sample can be discriminated clearly.

In another aspect, the present disclosure relates to a method for discriminating individual *Lactobacillus acidophilus* strains, which includes: A) a step of obtaining a PCR product through polymerase chain reaction (PCR) by using a DNA isolated from a target sample to be discriminated as a template and using a primer set consisting of a forward primer represented by SEQ ID NO: 8 and a reverse primer represented by SEQ ID NO: 16; and b) a step of identifying the presence of the PCR product.

In another aspect, the present disclosure relates to a method for detecting individual *Lactobacillus acidophilus* strains from a clinical, environmental or food sample, which includes: I) a step of performing polymerase chain reaction (PCR) by using a primer set consisting of a forward primer represented by SEQ ID NO: 8 and a reverse primer represented by SEQ ID NO: 16; and II) a step of identifying the formation of a PCR product.

First, a PCR product is obtained by performing polymerase chain reaction (PCR) by using the DNA isolated from a target sample to be discriminated as a template.

The DNA may be isolated from the sample using a method known in the art. The DNA may be extracted specifically by alkaline extraction, hot water extraction, column extraction or phenol/chloroform extraction, more specifically by alkaline extraction.

The target sample to be discriminated may include various samples wherein the presence of individual *Lactobacillus acidophilus* strains or the *Lactobacillus acidophilus* LA1 strain is desired to be detected. Specifically, it may be a clinical, environmental or food sample.

When the primer is designed and the DNA is prepared from the target sample to be discriminated as described above, DNA amplification may be performed by various methods including polymerase chain reaction (PCR), nucleic acid sequence-based amplification (NASBA), ligase chain reaction (LCR) and rolling circle amplification (RCA).

However, polymerase chain reaction (PCR) is the most general and desired method of amplifying a specific target DNA sequence.

And, the PCR may be real-time PCR, qRT-PCR or RT-PCR, although not being limited thereto.

In the present disclosure, "polymerase chain reaction" or "PCR" generally refers to a method of amplifying a desired target sequence in vitro, and is not specially limited as long as it is a process commonly used in the art. For example, the PCR process includes a step of adding an excess amount (2 molar equivalents or more) of oligonucleotide primers complementary to the double-stranded target sequence to a reaction mixture containing the desired target sequence(s). The reaction mixture is subjected to thermal cycling in the presence of a DNA polymerase, so that the desired target sequence is amplified between the DNA primer set.

A PCR product obtained through the above process is also called a "PCR fragment", a "reverse transcriptase PCR fragment" or an "amplicon", and refers to a polynucleotide molecule (or molecules) produced from amplification of a specific target nucleic acid. The PCR fragment generally refers to a DNA PCR fragment, although not being limited thereto. The PCR fragment may be a single-stranded fragment, a double-stranded fragment or a mixture thereof at any ratios. The PCR fragment or the reverse transcriptase PCR fragment may be 100-500 nucleotides or longer.

The presence of individual *Lactobacillus acidophilus* strains may be identified and detected by analyzing the amplified PCR product. The *Lactobacillus acidophilus* strain may be specifically a *Lactobacillus acidophilus* ATCC 4356, *Lactobacillus acidophilus* NCFM or *Lactobacillus acidophilus* LA1 strain.

In order to identify and detect *Lactobacillus acidophilus* YT1 with the above-described method, it is desired that the primer set further includes a primer set consisting of SEQ ID NO: 7 and SEQ ID NO: 15.

In the present disclosure, the presence of a *Lactobacillus acidophilus* strain may be detected or discriminated by analyzing the amplified PCR product. Furthermore, in the present disclosure, individual *Lactobacillus acidophilus* strains may be discriminated by analyzing the gene fragment of the amplified PCR product or the size of the amplification product. Specifically, since the *Lactobacillus acidophilus* strains belonging to the same genus and species synthesize PCR products with different sizes of 165 bp, 837 bp, 898 bp, 900 bp and 1000 bp under the same condition of annealing temperature and time, the individual *Lactobacillus acidophilus* strains existing in the sample can be identified and discriminated based thereon.

That is to say, a PCR product of about 898 bp corresponds to *Lactobacillus acidophilus* ATCC 4356 and *Lactobacillus acidophilus* NCFM, and a PCR product of 165 bp may be discriminated as *Lactobacillus acidophilus* LA1.

The method according to the present disclosure enables accurate and fast discrimination and analysis of the *Lactobacillus acidophilus* LA1 strain with high reliability through acquisition of the information of the PCR product specific for the *Lactobacillus acidophilus* LA1 strain and comparison of the gene data of the *Lactobacillus acidophilus* LA1 strain with the strains of the same species and genus based on the acquired information.

If there is a PCR product with a size of 150-250 bp, specifically 150-200 bp, it can be clearly discriminated that the *Lactobacillus acidophilus* LA1 strain is present in the sample.

In another aspect, the present disclosure relates to a method for discriminating a *Lactobacillus acidophilus* YT1 strain, which includes: 1) a step of obtaining a PCR product through polymerase chain reaction (PCR) by using a DNA isolated from a target sample to be discriminated as a template and using a primer set consisting of a forward primer represented by SEQ ID NO: 7 and a reverse primer represented by SEQ ID NO: 15; and 2) a step of identifying the presence of the PCR product.

The present disclosure also relates to a method for detecting a *Lactobacillus acidophilus* YT1 strain from a clinical, environmental or food sample, which includes: a) a step of performing polymerase chain reaction (PCR) by using a primer set consisting of a forward primer represented by SEQ ID NO: 8 and a reverse primer represented by SEQ ID NO: 16; and b) a step of identifying the formation of a PCR product.

First, a PCR product is obtained by performing polymerase chain reaction (PCR) using the DNA isolated from the target sample to be discriminated as a template and using the composition.

The DNA may be isolated from the sample using a method known in the art. The DNA may be extracted specifically by alkaline extraction, hot water extraction, column extraction or phenol/chloroform extraction, more specifically by alkaline extraction.

The target sample to be discriminated may include various samples wherein the presence of the *Lactobacillus acidophilus* YT1 strain is desired to be detected.

When the primer is designed and the DNA is prepared from the target sample to be discriminated as described above, DNA amplification may be performed by various methods including polymerase chain reaction (PCR), nucleic acid sequence-based amplification (NASBA), ligase chain reaction (LCR) and rolling circle amplification (RCA). However, polymerase chain reaction (PCR) is the most general and desired method of amplifying a specific target DNA sequence.

And, the PCR may be real-time PCR, qRT-PCR or RT-PCR, although not being limited thereto.

In the present disclosure, "polymerase chain reaction" or "PCR" generally refers to a method of amplifying a desired target sequence in vitro, and is not specially limited as long as it is a process commonly used in the art. For example, the PCR process includes a step of adding an excess amount (2 molar equivalents or more) of oligonucleotide primers complementary to the double-stranded target sequence to a reaction mixture containing the desired target sequence(s). The reaction mixture is subjected to thermal cycling in the presence of a DNA polymerase, so that the desired target sequence is amplified between the DNA primer set.

A PCR product obtained through the above process is also called a "PCR fragment", a "reverse transcriptase PCR fragment" or an "amplicon", and refers to a polynucleotide molecule (or molecules) produced from amplification of a specific target nucleic acid. The PCR fragment generally refers to a DNA PCR fragment, although not being limited thereto. The PCR fragment may be a single-stranded fragment, a double-stranded fragment or a mixture thereof at any ratios. The PCR fragment or the reverse transcriptase PCR fragment may be 100-500 nucleotides or longer.

The presence of the *Lactobacillus acidophilus* YT1 strain may be identified and discriminated by analyzing the amplified PCR product. The analysis may be performed by analyzing the base sequence of the PCR product or the size of the amplification product (for the *Lactobacillus acidophilus* YT1 strain, the size of the PCR product is 300-350 bp, specifically 320 bp).

In the present disclosure, the *Lactobacillus acidophilus* YT1 strain may be identified and discriminated by analyzing the amplified PCR product. Furthermore, in the present disclosure, the *Lactobacillus acidophilus* YT1 strain may be accurately discriminated by analyzing the gene fragment of the amplified PCR product.

That is to say, the *Lactobacillus acidophilus* YT1 strain may be identified and analyzed accurately and quickly with high reliability by acquiring the information about the PCR product appearing specifically in the *Lactobacillus acidophilus* YT1 strain and comparing with the gene information of the strains belonging to the same species and genus as the *Lactobacillus acidophilus* YT1 strain.

If there is a PCR product with a size of 300-350 bp, specifically 320 bp, it can be clearly discriminated that the *Lactobacillus acidophilus* YT1 strain is present in the sample.

MODE FOR INVENTION

Hereinafter, the present disclosure will be described in more detail through examples, etc. However, it should be construed that the content and scope of the present disclosure are reduced or limited by the examples, etc. In addition, it will be obvious that those of ordinary skill can easily carry out the present disclosure even for the matter the experimental result of which is not presented specifically based on the disclosure of the present disclosure including the examples, and that such modification and change are within the scope of the present disclosure.

The experimental results presented below are the results of representative examples and comparative examples.

Example 1. Analysis of CRISPR Structure of *Lactobacillus acidophilus* and Design of Primer Set The genomes of 21 strains belonging to the species *Lactobacillus acidophilus*, the genome information of which is known, were comparatively analyzed. Specifically, the 21 sp. strains are as follows: *L. acidophilus* YT1, *L. acidophilus* NCFM (GCA 000011985.1), *L. acidophilus* ATCC 4796 (GCA 000159715.1), *L. acidophilus* La-14 (GCA 000389675.2), *L. acidophilus* DSM 20242 (GCA 000442825.1), *L. acidophilus* CIRM-BIA 442 (GCA 000442865.1), *L. acidophilus* DSM 9126 (GCA 000469745.1), *L. acidophilus* CIRM-BIA 445 (GCA 000469765.1), *L. acidophilus* CFH (GCA 000497795.1), *L. acidophilus* JCM 1132 (GCA 000615165.1), *L. acidophilus* ATCC 4356 (GCA 000786395.1), *L. acidophilus* FSI4 (GCA 000934625.1), *L. acidophilus* DSM 20079 (GCA 001433895.1), *L. acidophilus* NBRC 13951 (GCA 001591845.1), *L. acidophilus* WG-LB-IV (GCA 001639165.1), *L. acidophilus* KLDS 1.0901 (GCA 001868765.1), *L. acidophilus* L-55 (GCA 001950045.1), *L. acidophilus* ATCC 53544 (GCA 002224305.1), *L. acidophilus* LA1 (GCA 002286215.1), *L. acidophilus* P2 (GCA 002406675.1) and *L. acidophilus* LMG P-21904 (GCA 002914945.1).

The genomes of the 21 sp. strains were acquired from the NCBI Genome site (https://www.ncbi.nlm.nih.gov/genome/genomes/1099). From the genome information of each strain, the CRISPR region indicative of evolutionary history was analyzed using CRISPRCasFinder (version 1.0), and the sequence shared by all *Lactobacillus acidophilus* was identified by comparing the CRISPR structure of the strains.

Figure 1:
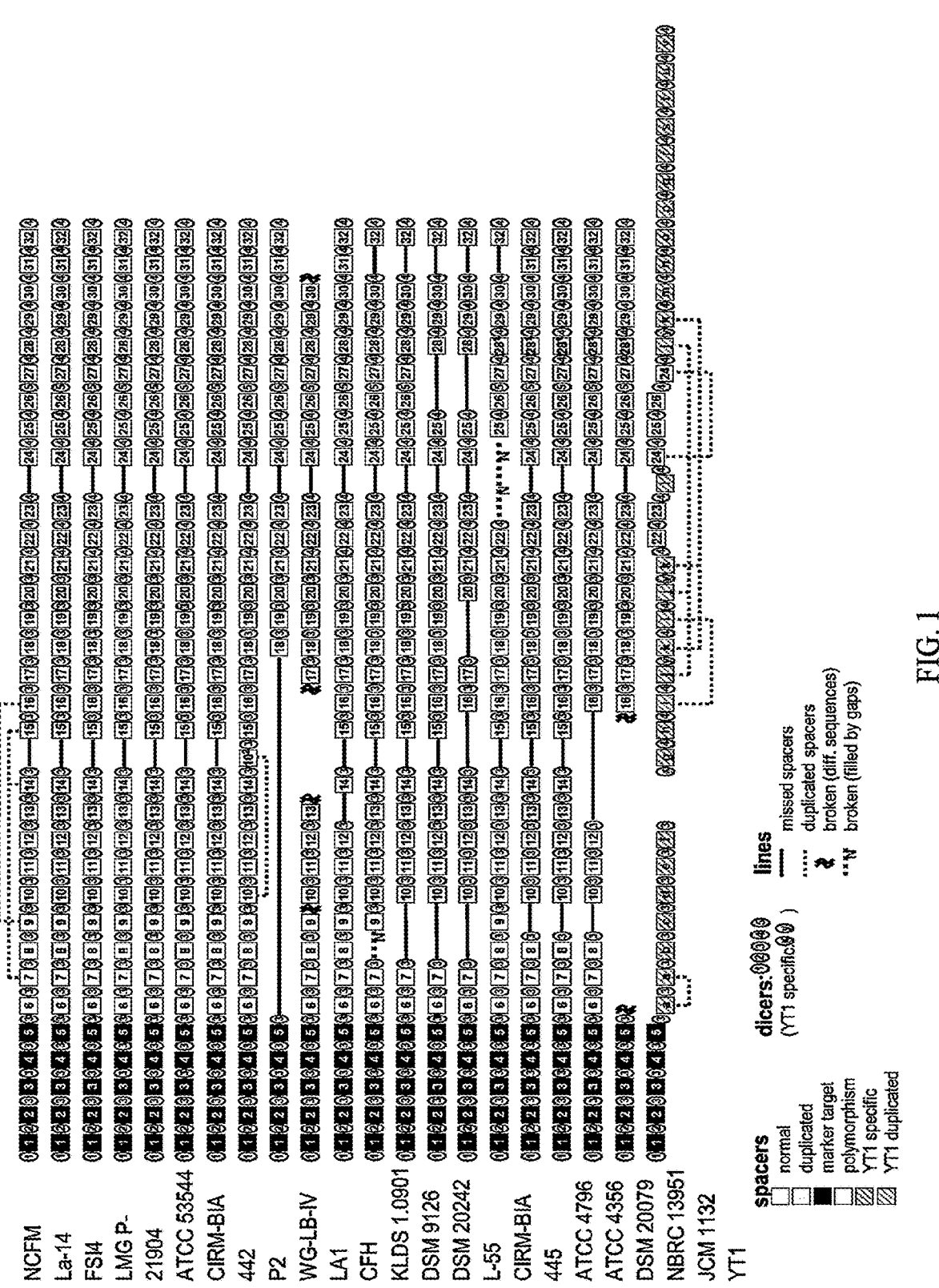
FIG. 1 shows a CRISPR structure analysis result for *Lactobacillus acidophilus* strains (21 species) identified in Example 1.

FIG. 1 shows a CRISPR structure analysis result of *Lactobacillus acidophilus* strains (21 species) identified in Example 1.

It was confirmed that the CRISPR region of the 21 sp. strains belonging to the species *Lactobacillus acidophilus* share spacers 1-5.

Accordingly, the inventors of the present disclosure have intended to design markers (primer sets) capable of specifically detecting strains belonging to the species *Lactobacillus acidophilus* using the CRISPR spacers 1-5 shared by the strains belonging to the species *Lactobacillus acidophilus*. As a result, they have finally designed a primer set of SEQ ID NOS: 1 and 9, a primer set of SEQ ID NOS: 2 and 10, a primer set of SEQ ID NOS: 3 and 11, a primer set of SEQ ID NOS: 4 and 12, a primer set of SEQ ID NOS: 5 and 13, and a primer set of SEQ ID NOS: 5 and 14.

Figure 2:
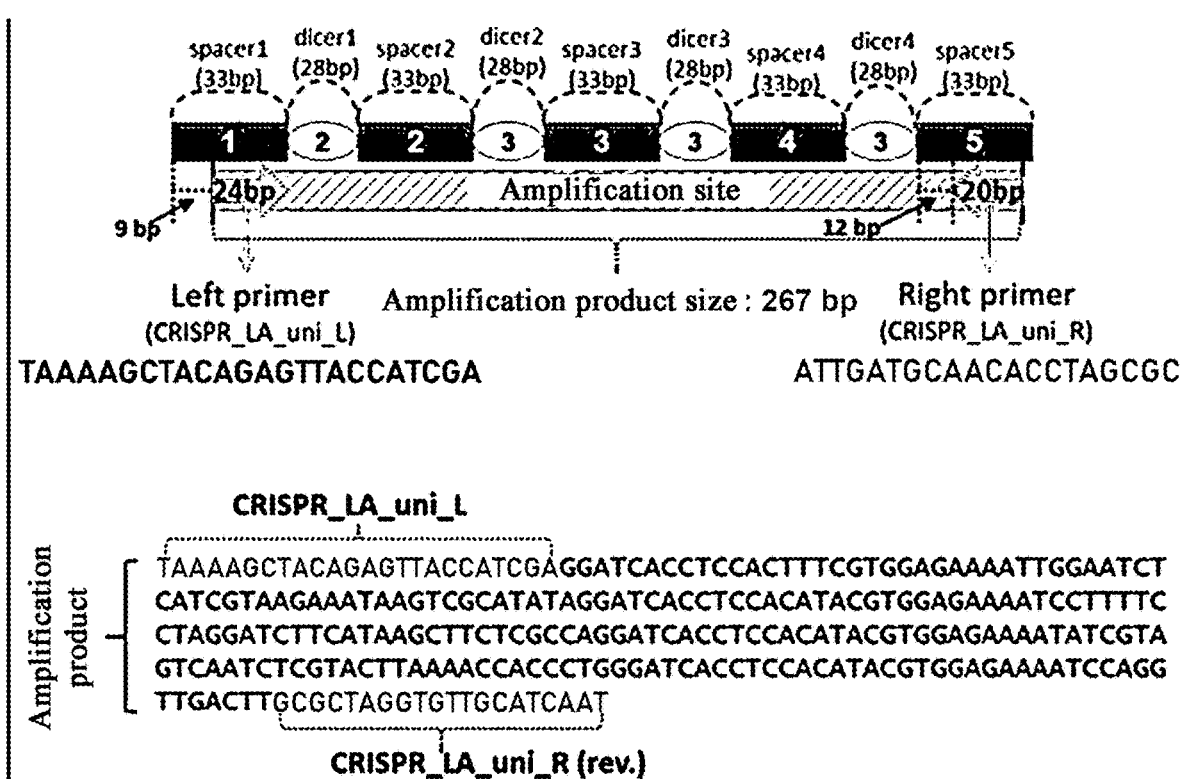
FIG. 2 schematically shows a primer set represented by SEQ ID NOS: 1 and 9, which is capable of specifically detecting all *Lactobacillus acidophilus* and the size of a PCR product of a strain, obtained by performed PCR using the primer set, which was analyzed by in silico analysis.

Among the primer sets, the primer set represented by SEQ ID NOS: 1 and 9 and the size of a PCR amplification product that can be obtained therefrom are shown in FIG. 2. More specifically, FIG. 2 schematically shows the primer set represented by SEQ ID NOS: 1 and 9, which is capable of specifically detecting all *Lactobacillus acidophilus* and the size of a PCR product of a strain, obtained by performed PCR using the primer set, which was analyzed by in silico analysis.

As shown in FIG. 2, the primer set includes a forward primer represented by SEQ ID NO: 1 and a reverse primer represented by SEQ ID NO: 9. As shown in FIG. 2, the inventors have prepared a marker capable of specifically detecting the strains belonging to the species *Lactobacillus acidophilus* by developing a primer including the spacers of the CRISPR region shared by the strains belonging to the species *Lactobacillus acidophilus*. Specifically, a left primer was prepared from the 10 bp to 24 bp of the spacer 1 of *Lactobacillus acidophilus* and a right primer was prepared from the 20 bp of the spacer 5. It was confirmed that the primer can be applied universally to all the strains belonging to the species *Lactobacillus acidophilus* and enables distinct distinction from the strains of other species or genera.

In addition, a PCR product was obtained by performing PCR using the designed primer set and the length of the PCR product was analyzed by in silico modeling. The result is shown in FIG. 3. As a result of the analysis, it was confirmed that the length of the PCR product of the strains belonging to the species *Lactobacillus acidophilus* was 267 bp.

That is to say, it was confirmed that the presence of a strain belonging to the species *Lactobacillus acidophilus* in a sample can be detected using the primer set according to the present disclosure.

In the present disclosure, for preparation of a primer set for discriminating a strain belonging to the species *Lactobacillus acidophilus*, a primer set with a total primer length of 20-30 bp was designed. Specifically, the primers of the primer set may have the same or different length. Specifically, a forward primer represented by SEQ ID NO: 1 may have a length of 24 bp, and a reverse primer represented by SEQ ID NO: 9 may have a length of 20 bp. The primers were designed to have a melting temperature ($T_m$) of 57-63° C., specifically 60° C., the maximum difference in $T_m$ between the primers of 3-5° C. or smaller, and GC % of 50-37.5%.

The specificity of a composition of the primer set of SEQ ID NOS: 1 and 9 for the strains belonging to the species *Lactobacillus acidophilus* was analyzed through in silico analysis and sequence matching on the NCBI DB. As a result (FIG. 3), it was confirmed that the primer set composition designed in the present disclosure can amplify only the strains belonging to the species *Lactobacillus acidophilus* among the sequences listed in the NCBI DB.

Figure 3A:
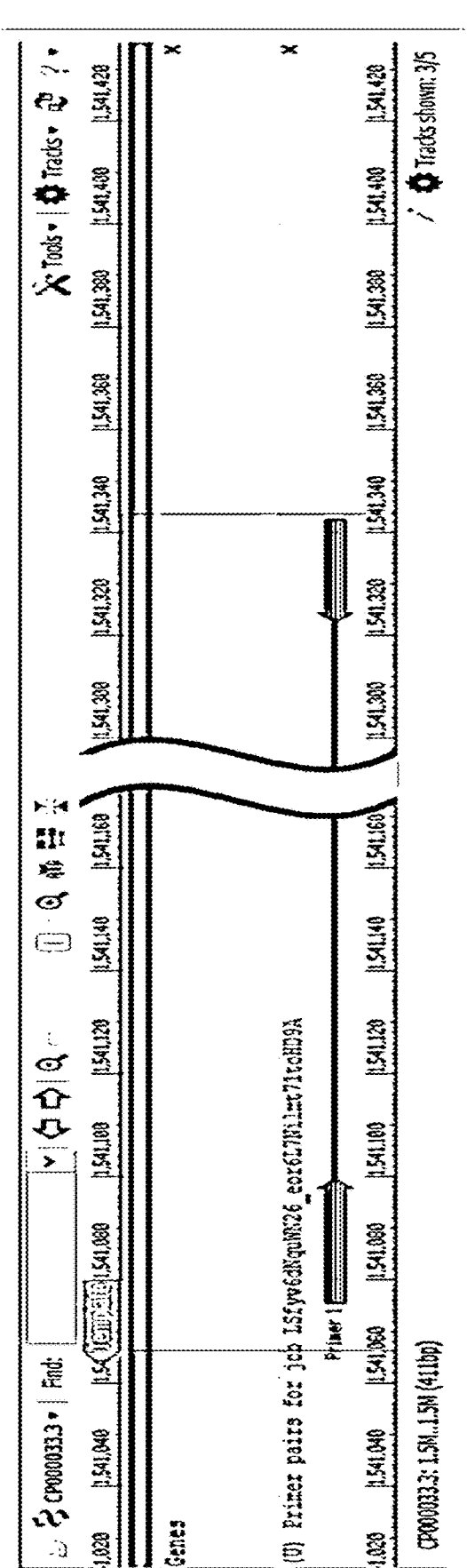
FIG. 3a shows a result of analyzing the sequence of a primer set represented by SEQ ID NOS: 1 and 9, which is capable of specifically detecting *Lactobacillus acidophilus*, using a sequence search program called Primer-BLAST by comparing with the NCBI database.

FIGS. 3*a* and 3*b* shows a result of analyzing the sequence of the primer set represented by SEQ ID NOS: 1 and 9, which is capable of specifically detecting *Lactobacillus acidophilus*, using a sequence search program called Primer-BLAST by comparing with the NCBI database. FIG. 3*a* shows the upper screen of the program, and FIG. 3*b* shows the analysis result. On the Primer-BLAST website, PCR template was designated as CP000033.3 (accession number of the *L. acidophilus* NCFM genome), forward primer region as 1,541,067-1,541,099 (location of spacer 1 on the genome), and reverse primer region as 1,541,311-1,541,343 (location of spacer 5 on the genome). As the primer parameters, CRISPR_LA_uni_F (SEQ ID NO: 1) was inputted for the forward primer sequence and CRISPR_LA_uni_R (SEQ ID NO: 9) for the reverse primer sequence. The database was designated as "nr" (or nucleotide collection) and the target organism was designated as none. The program was executed with the remaining setting as default setting.

As a result, it was confirmed that the universal primer set for discriminating strains belonging to the species *Lactobacillus acidophilus* amplifies *Lactobacillus acidophilus* YT1, *Lactobacillus acidophilus* DSM 20079, *Lactobacillus acidophilus* LA1, *Lactobacillus acidophilus* ACTC 53544, *Lactobacillus acidophilus* FSI14, *Lactobacillus acidophilus* La-14 and *Lactobacillus acidophilus* NCFM among the sequences listed in the NCBI database. Specifically, it was stated that "Primer may not be specific to the input PCR template as targets were found in selected database: Nucleotide collection (nt)" in the "Specificity of primers" section of FIGS. 3*a* and 3*b*. This means that although specific strains belonging to the species *Lactobacillus acidophilus* are not amplified, the primer may be used as a universal primer for the species *Lactobacillus acidophilus* because all the detected sequences correspond to the strains belonging to the species *Lactobacillus acidophilus*.

Example 2. Culturing of *Lactobacillus acidophilus* LA1 Strain

For genome sequencing of a *Lactobacillus acidophilus* LA1 strain, a *Lactobacillus acidophilus* LA1 strain was cultured in MRS medium (Difco, 288110) at 37° C. for 18 hours.

Example 3. Securing of Genome of *Lactobacillus acidophilus* LA1 Strain

For genome sequencing of a *Lactobacillus acidophilus* LA1 strain, a colony was recovered from the culture medium of Example 2 and genomic DNA was extracted with a QIAamp DNA Mini kit (Qiagen, Germany). Then, whole genome base sequence was obtained using a PacBio RS II sequencing platform.

Sequence read assembly was performed using HGAP 3.0, and the location of the chromosomal replication initiator gene dnaA was identified to determine the initiation point of the whole genome.

Example 4. Comparison of Genome of *Lactobacillus acidophilus* LA1 Strain

The NCBI Prokaryotic Genome Annotation Pipeline (PGAAP) was used to identify the function of the genes existing in the genome of *Lactobacillus acidophilus* LA1.

Then, the genome of 9 similar sp. strains belonging to the same species as *Lactobacillus acidophilus* LA1 was compared. Specifically, the 9 sp. strains are as follows: *L. acidophilus* NCFM (assembly accession: GCF_000011985.1), *L. acidophilus* La-14 (GCF_000389675.2), *L. acidophilus* FSI4 (GCF_000934625.1), *L. gallinarum* HFD4 (GCF_001314245.2), *L. helveticus* CNRZ32 (GCF_000422165.1), *L. crispatus* ST1 (GCF_000091765.1), *L. kefiranofaciens* ZW3 (GCF_000214785.1), *L. amylovorus* GRL1118 (GCF_000194115.1) and *L. acetotolerans* NBRC 13120 (GCF_001042405.1). Then, the whole genome information was analyzed in the same way as the *Lactobacillus acidophilus* LA1 strain.

Molecular genealogy was constructed by the maximum likelihood method based on the Tamura-Nei model using the 16S rRNA gene information of the 9 sp. strains. For similarity analysis of the whole genome, molecular genealogy based on the whole genome information was constructed using orthologous average nucleotide identity (OrthoANI) to investigate the relationship between the *Lactobacillus acidophilus*-related microorganisms.

Additionally, the CRISPR region providing information about phage infection of each strain was analyzed with a CRISPR finder, and the CRISPR structure of each strain was compared.

Figure 4:
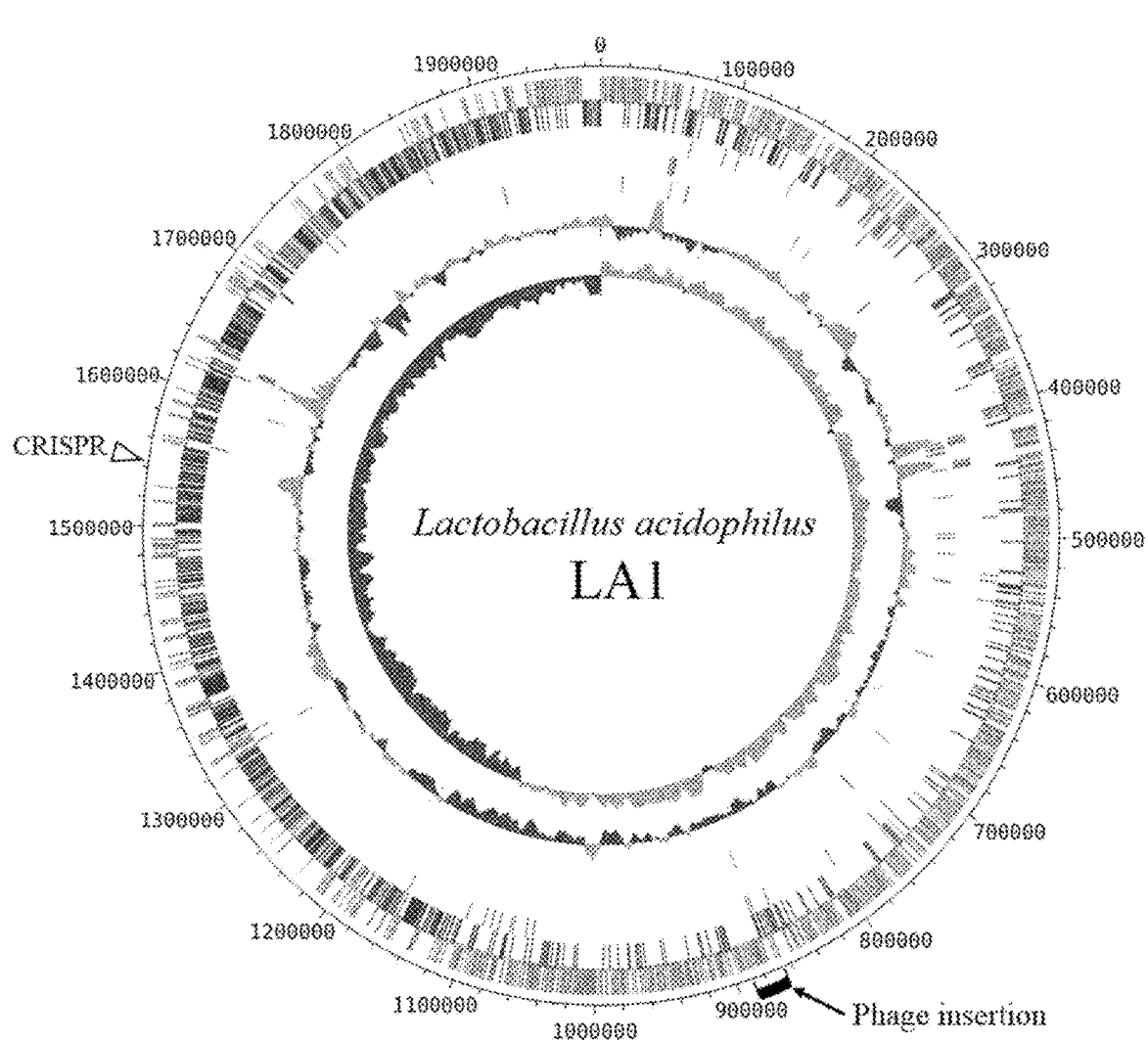
FIG. 4 shows the whole genome configuration of *Lactobacillus acidophilus* LA1 analyzed in Example 3.

FIG. 4 shows the whole genome configuration of *Lactobacillus acidophilus* LA1 analyzed in Example 3. From the analysis result of the *Lactobacillus acidophilus* LA1 genome, it was confirmed that the whole genome of LA1 is a 1.99 Mbp circular chromosome (34.7% G+C content), with 1,953 functional genes, 76 RNA genes and 33 pseudogenes.

Figure 5A:
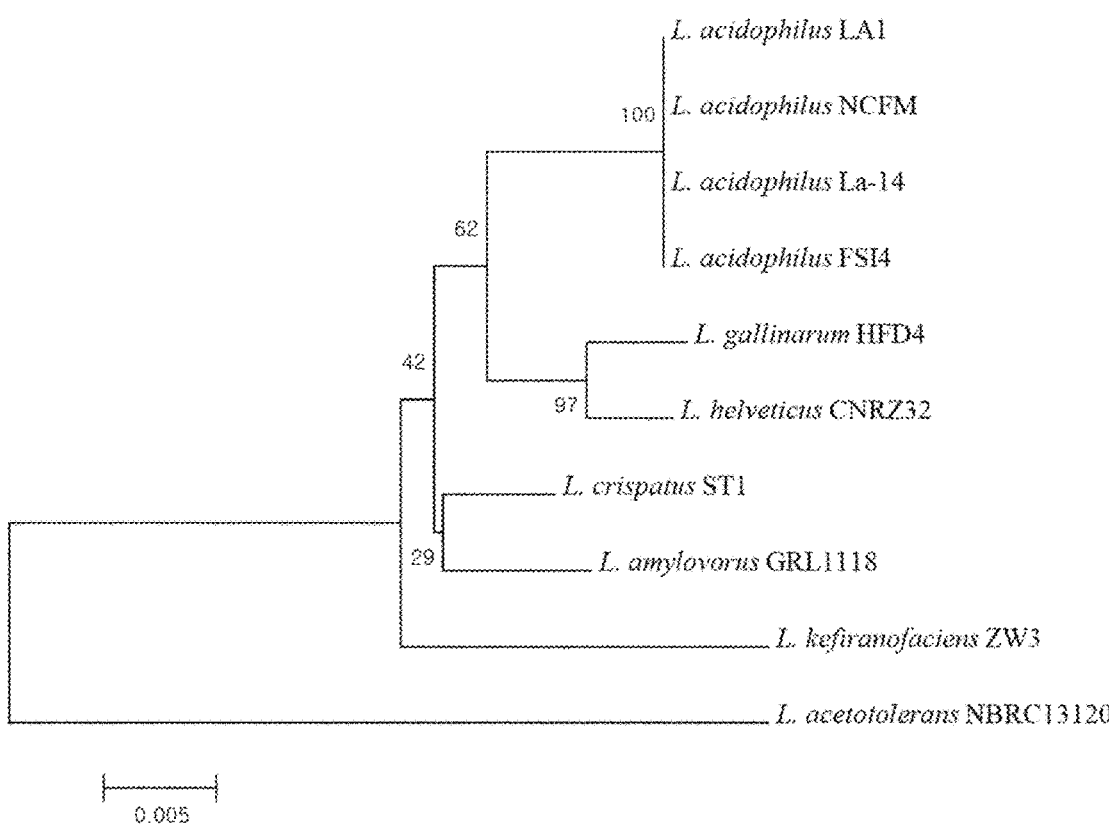
FIG. 5a shows the genealogy of 10 sp. strains including *Lactobacillus acidophilus* LA1 confirmed in Example 4 based on the 16S rRNA gene.
Figure 5B:
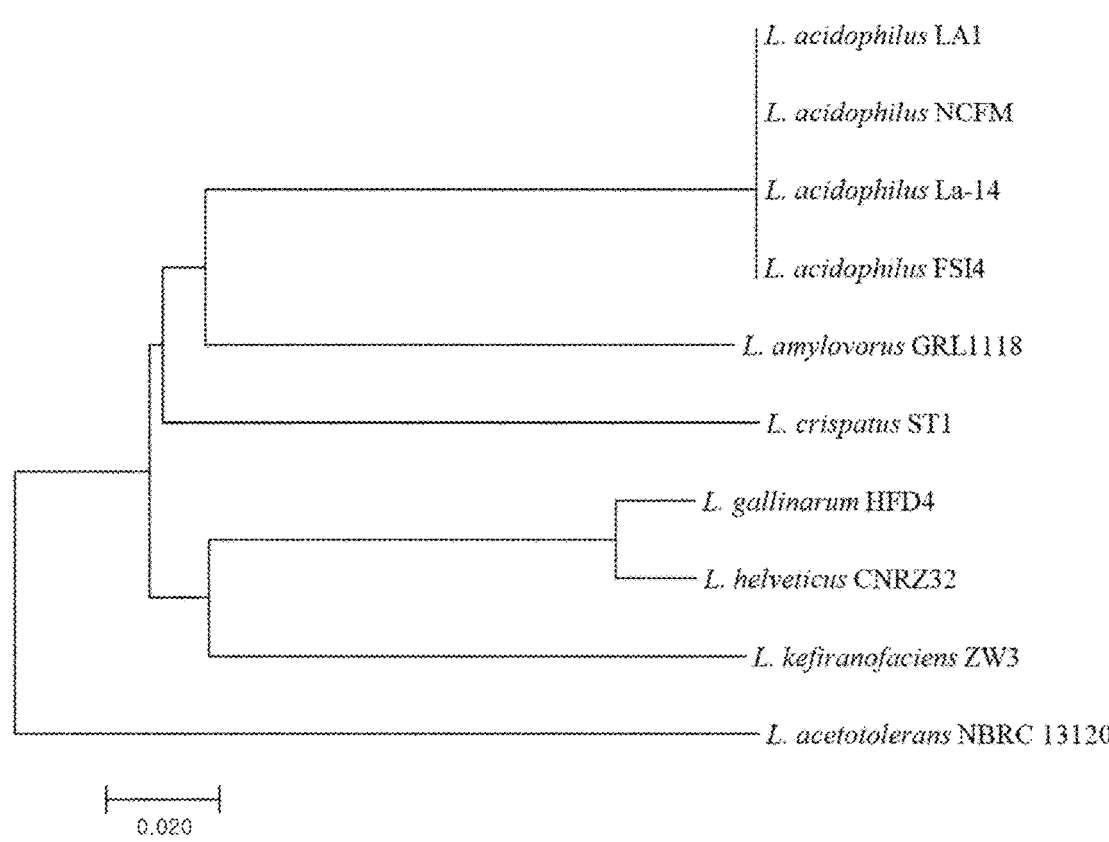
FIG. 5b shows the genealogy of 10 sp. strains including *Lactobacillus acidophilus* LA1 confirmed in Example 4 through comparison of the ANI genome.

FIG. 5*a* shows the genealogy of 10 sp. strains including *Lactobacillus acidophilus* LA1 confirmed in Example 4 based on the 16S rRNA gene, and FIG. 5*b* shows the genealogy of 10 sp. strains including *Lactobacillus acidophilus* LA1 confirmed in Example 4 through comparison of the ANI genome.

As shown in FIGS. 5*a* and 5*b*, it was confirmed through the molecular genealogy using 16S rRNA gene and Ortho-ANI that the 10 sp. strains including *Lactobacillus acidophilus* LA1 have genetic similarity. Specifically, 4 sp. strains belonging to *Lactobacillus acidophilus* (*L. acidophilus* NCFM, Lacidophilus La-14, *L. acidophilus* FSI4 and *L. acidophilus* LA1) were very similar with almost no observable difference between the strains.

FIG. 6 shows the CRISPR structure analysis result for *Lactobacillus acidophilus* NCFM, *Lactobacillus acidophilus* La-14, *Lactobacillus acidophilus* FSI4 and *Lactobacillus acidophilus* LA1 from among the 10 sp. strains including *Lactobacillus acidophilus* LA1 confirmed in Example 4. Specifically, FIG. 6 shows the result of analyzing only the CRISPR region from the whole genome of *L. acidophilus* NCFM, Lacidophilus La-14, *L. acidophilus* FSI4 and *L. acidophilus* LA1 analyzed in Example 4.

Distinct difference in the base sequences of the *L. acidophilus* NCFM, Lacidophilus La-14, *L. acidophilus* FSI4 and *L. acidophilus* LA1 strains in the CRISPR region was identified. Especially, whereas the *L. acidophilus* NCFM, Lacidophilus La-14 and *L. acidophilus* FSI4 strains had 32 spacer regions, the spacer regions 6-17 were lost in the *L. acidophilus* LA1 strain.

Therefore, the inventors have designed a marker capable of specifically identifying and detecting *L. acidophilus* strains in a general sample and capable of specifically detecting the *L. acidophilus* LA1 strain from among the strains based on the difference in the CRISPR structure, which is shown in FIG. 7. More specifically, FIG. 7 shows a primer set capable of specifically detecting *L. acidophilus* LA1 and the size of the PCR product of each strain obtained using the primer set, analyzed by in silico analysis.

As shown in FIG. 7, the *L. acidophilus* strain can be identified specifically since it includes the CRISPR region unlike other strains. In addition, since the *L. acidophilus* LA1 strain lacks the base sequences of 6-17 regions of CRISPR unlike other strains, the *L. acidophilus* LA1 strain can be identified specifically based on this. For this, the inventors have designed a marker capable of specifically detecting the *L. acidophilus* strain, specifically *L. acidophilus* LA1 strain, by developing a primer including the 6-17 regions of CRISPR. Specifically, a left primer was prepared from the spacer 6 region and a right primer was prepared from the spacer 20 region, based on *L. acidophilus* NCFM, Lacidophilus La-14 and *L. acidophilus* FSI4. It was confirmed that the *L. acidophilus* LA1 strain can be certainly distinguished according to the present disclosure.

In addition, the length of a PCR product obtained by performing PCR for each strain using a primer set designed according to the present disclosure was analyzed by in silico modeling, and the result is shown in FIG. 7. As a result, the length of the PCR product of *L. acidophilus* LA1 was 165 bp (150 bp+8 bp primer+7 bp dicer), whereas the length of the PCR product of other *L. acidophilus* strains such as *L. acidophilus* NCFM, Lacidophilus La-14, *L. acidophilus* FSI4, etc. was about 898 bp (883 bp+8 bp primer+7 bp dicer).

That is to say, it can be seen that the presence of the *L. acidophilus* strain in a sample can be detected using the primer set according to the present disclosure and the *L. acidophilus* LA1 can be identified certainly from among the *L. acidophilus* strains only with the length of the PCR product.

Then, the sequence of the primer set for discriminating a *L. acidophilus* strain of the present disclosure was analyzed in silico by referring to the NCBI database using the BLASTN sequence search program.

Short sequences with a size of about 20 bp were searched with a task option as "blastn-short" and e-value as 1.0, with the low-complexity filtering condition dust excluded. The search result was visualized to determine similarity by denoting matching codes as 'O', non-matching codes as '/' and non-aligned portions as '-', as shown in the "align_code" row in Tables 2-9. As a result, all the species of *L. acidophilus* were identical to the primer set, and at least two codes were determined as non-matching or non-aligned for the other species.

In the present disclosure, the most important thing in the preparation of a primer set for discriminating *L. acidophilus* was to design such that the total length of the primer is 18-23 bp (optimum length 20 bp). In addition, the primers were designed to have a melting temperature ($T_m$) of 57-62° C., specifically 59° C., the maximum difference in $T_m$ between the primers of 5° C. or smaller, and GC % of 35-65%, specifically 50%.

The specificity of a composition of the primer set of SEQ ID NOS: 8 and 16 for the *L. acidophilus* strain, particularly *L. acidophilus* LA1, was analyzed through in silico analysis and sequence matching on the NCBI DB. As a result (Tables 2-9), it was confirmed that the primer set composition designed in the present disclosure can amplify only the species *Lactobacillus acidophilus*. In addition, among the detected strains of the species *Lactobacillus acidophilus*, the PCR product for LA1 was smaller by 720 bp. Through this, it was confirmed that the LA1 strain can be discriminated clearly and accurately.

Example 5. Culturing of *Lactobacillus acidophilus* YT1 Strain

For genome sequencing of a *Lactobacillus acidophilus* YT1 strain, the *Lactobacillus acidophilus* YT1 strain published in Korean Patent Publication No. 10-2018-0052569 (accession number KCCM11808P) was cultured in MRS medium (Difco, 288110) at 37° C. for 18 hours.

Example 6. Securing of Genome of *Lactobacillus acidophilus* YT1 Strain

For genome sequencing of a *Lactobacillus acidophilus* YT1 strain, a colony was recovered from the culture medium of Example 5 and genomic DNA was extracted with a QIAamp DNA Mini kit (Qiagen, Germany). Then, whole genome base sequence was obtained using a PacBio RS II sequencing platform.

Sequence read assembly was performed using HGAP 3.0, and the location of the chromosomal replication initiator gene dnaA was identified to determine the initiation point of the whole genome.

Example 7. Comparison of Genome of *Lactobacillus acidophilus* YT1 Strain

The NCBI Prokaryotic Genome Annotation Pipeline (PGAAP) was used to identify the function of the genes existing in the genome of *Lactobacillus acidophilus* YT1.

Then, the genome of 21 sp. strains belonging to the same species as *Lactobacillus acidophilus* YT1 was compared. Specifically, the 21 sp. strains are as follows: *L. acidophilus* NCFM (GCA 000011985.1), *L. acidophilus* ATCC 4796 (GCA 000159715.1), *L. acidophilus* La-14 (GCA 000389675.2), *L. acidophilus* DSM 20242 (GCA 000442825.1), *L. acidophilus* CIRM-BIA 442 (GCA 000442865.1), *L. acidophilus* CIP 76.13 (GCA 000469705.1), *L. acidophilus* DSM 9126 (GCA 000469745.1), *L. acidophilus* CIRM-BIA 445 (GCA 000469765.1), *L. acidophilus* CFH (GCA 000497795.1), *L. acidophilus* JCM 1132 (GCA 000615165.1), *L. acidophilus* ATCC 4356 (GCA 000786395.1), *L. acidophilus* FSI4 (GCA 000934625.1), *L. acidophilus* DSM 20079 (GCA 001433895.1), *L. acidophilus* NBRC 13951 (GCA 001591845.1), *L. acidophilus* WG-LB-IV (GCA 001639165.1), *L. acidophilus* KLDS 1.0901 (GCA 001868765.1), *L. acidophilus* L-55 (GCA 001950045.1), *L. acidophilus* ATCC 53544 (GCA 002224305.1), *L. acidophilus* LA1 (GCA 002286215.1), *L. acidophilus* P2 (GCA 002406675.1) and *L. acidophilus* LMG P-21904 (GCA 002914945.1). Then, the whole genome information was analyzed in the same way as the *Lactobacillus acidophilus* YT1 strain.

Molecular genealogy was constructed by the maximum likelihood method based on the Tamura-Nei model using the 16S rRNA gene information of the 22 *Lactobacillus acidophilus* sp. strains including *Lactobacillus acidophilus* YT1. 16S rRNA of *Lactobacillus helveticus* CAUH18 was used as an out group of molecular genealogy. Computation was conducted for the region of 18-784 based on the 16S rRNA sequence of NCFM in consideration of some genome not having full-length 16S rRNA.

For similarity analysis of the whole genome, molecular genealogy based on the whole genome information was constructed using average nucleotide identity (ANI) to investigate the relationship between the *Lactobacillus acidophilus*-related microorganisms.

Additionally, the CRISPR region providing information about phage infection of each strain was analyzed with a CRISPR finder, and the CRISPR structure of each strain was compared.

Figure 8:
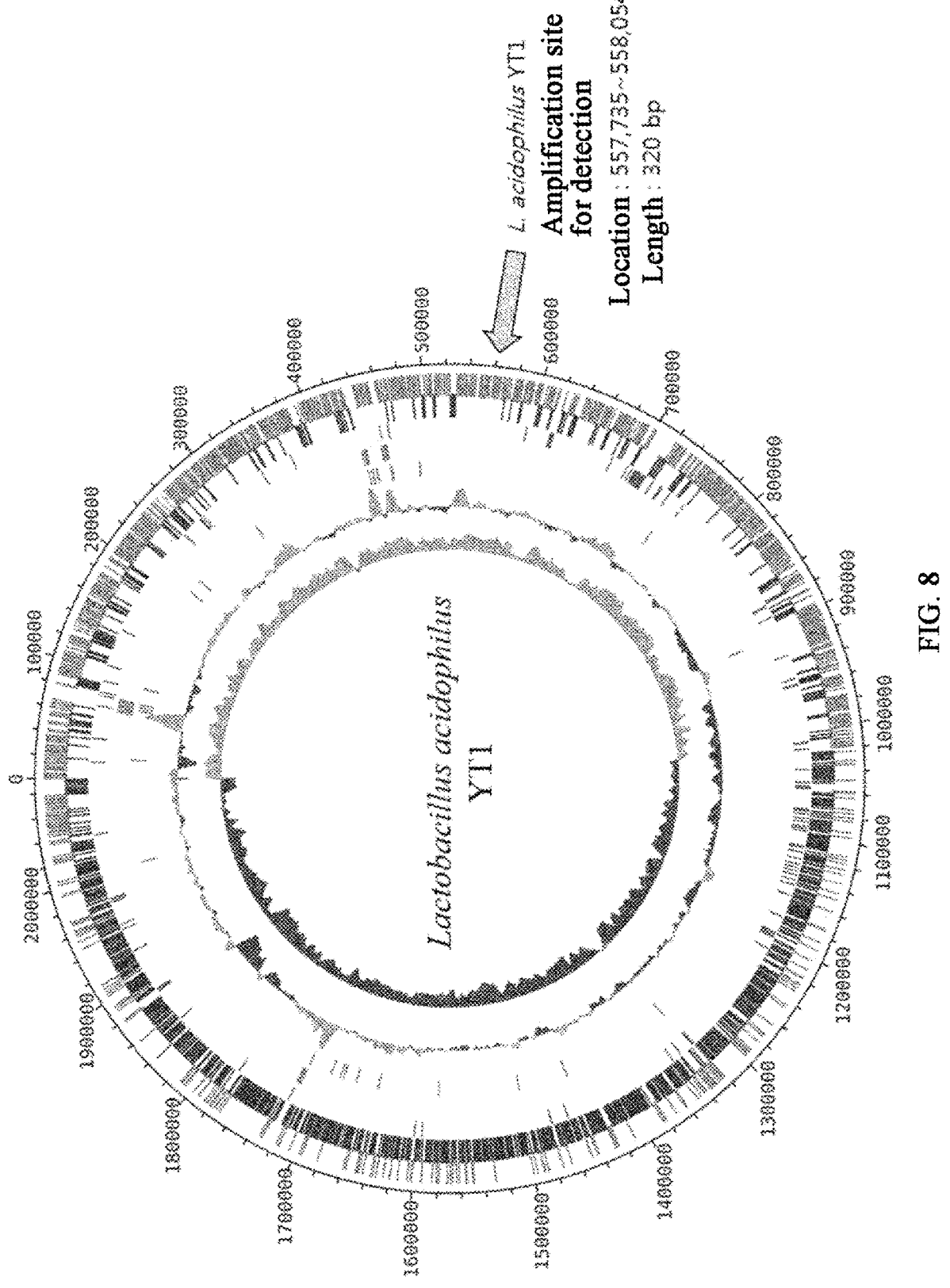
FIG. 8 shows the whole genome configuration of *Lactobacillus acidophilus* YT1 analyzed in Example 6.

FIG. 8 shows the whole genome configuration of *Lactobacillus acidophilus* YT1 analyzed in Example 6. From the analysis result of the *Lactobacillus acidophilus* YT1 genome, it was confirmed that the whole genome of YT1 is a 2.09 Mbp circular chromosome (34.7% G+C content), with 1,913 functional genes, 83 RNA genes and 93 pseudogenes.

Figure 9A:
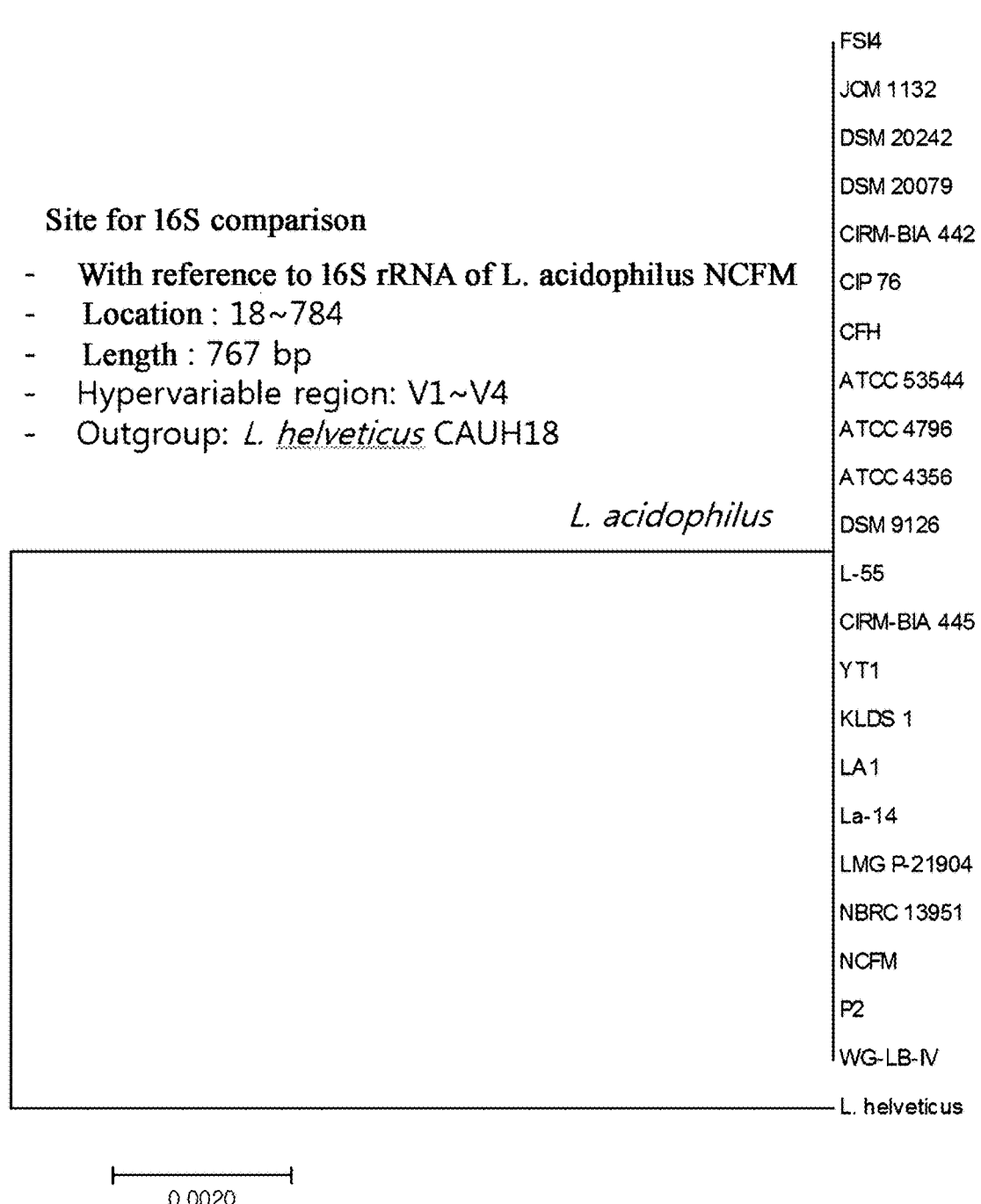
FIG. 9a shows the genealogy of 22 sp. strains of *Lactobacillus acidophilus* including *Lactobacillus acidophilus* YT1 confirmed in Example 7 based on the 16S rRNA gene.
Figure 9B:
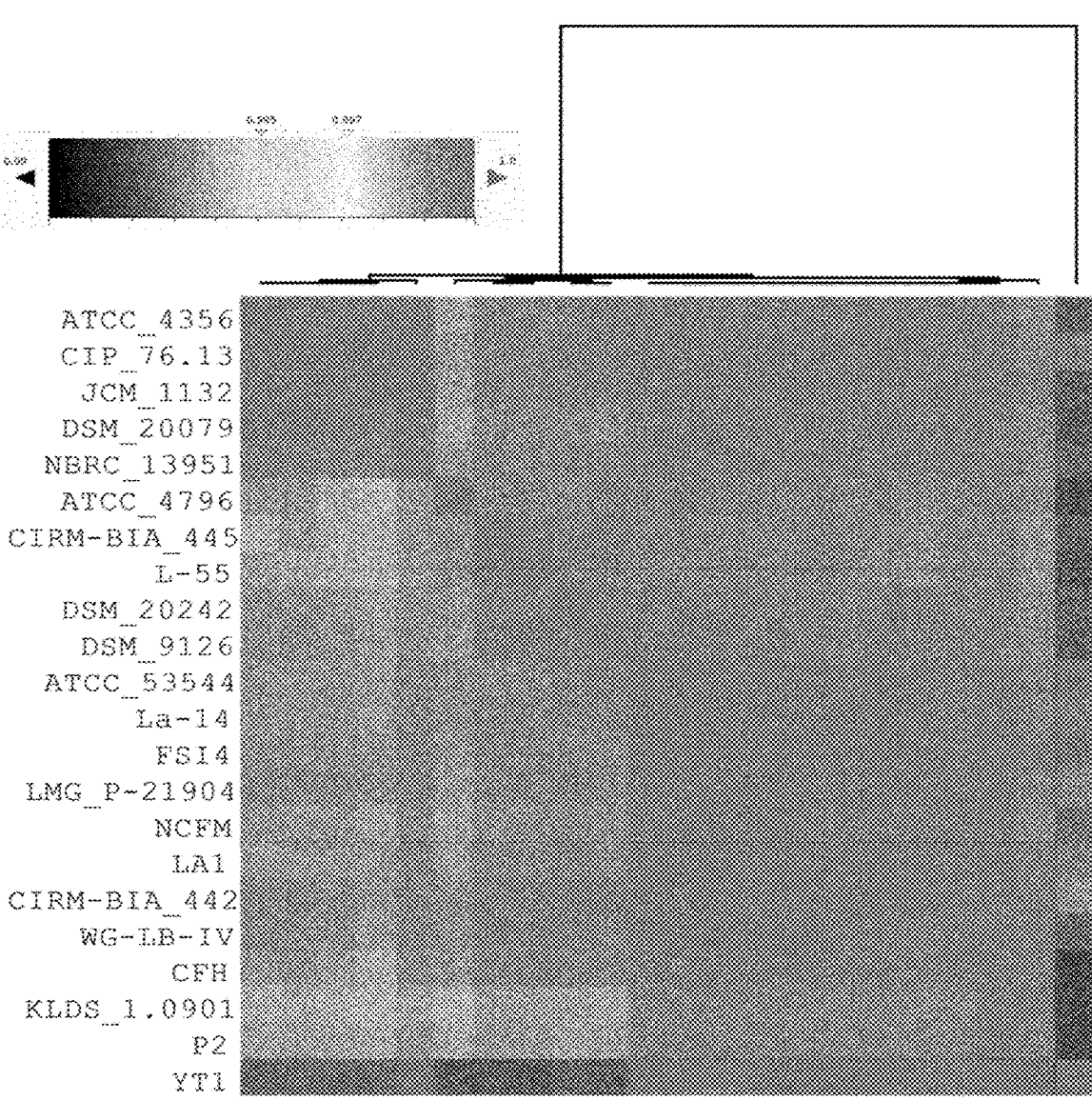
FIG. 9b shows the genealogy of 10 sp. strains including *Lactobacillus acidophilus* YT1 confirmed in Example 7 through comparison of the ANI genome.

FIG. 9a shows the genealogy of the 22 sp. strains of *Lactobacillus acidophilus* including *Lactobacillus acidophilus* YT1 confirmed in Example 7 based on the 16S rRNA gene, and FIG. 9b shows the genealogy of the 22 sp. strains including *Lactobacillus acidophilus* YT1 confirmed in Example 7 through comparison of the ANI genome.

As shown in FIGS. 9a and 9b, it was confirmed through the molecular genealogy using 16S rRNA gene and ANI that the 22 sp. strains including *Lactobacillus acidophilus* YT1 have genetic similarity. Specifically, the 21 sp. strains belonging *Lactobacillus acidophilus* except for YT1 had similarity of 99.7% or higher based on ANI, with almost no observable difference between the strains. YT1 showed slight difference in the whole genome from other strains in the species *L. acidophilus*, with a similarity of 99.5% or lower based on ANI.

FIG. 10 shows the CRISPR structure analysis result for the reference strains *Lactobacillus acidophilus* NCFM and *Lactobacillus acidophilus* YT1 from among the 22 sp. strains including *Lactobacillus acidophilus* YT1 confirmed in Example 7.

Specifically, FIG. 10 shows the result of analyzing only the CRISPR region of the whole genome of *L. acidophilus* NCFM and *L. acidophilus* YT1 analyzed in Example 7.

Clear difference in the base sequence of the CRISPR region was identified between the *L. acidophilus* NCFM and *L. acidophilus* YT1 strains. In particular, it was identified that, whereas 32 spacer regions are present in the *L. acidophilus* NCFM strain, the two CRISPR regions are split and conserved only partially for the *L. acidophilus* YT1 strain. Specifically, the spacers 1-5 of NCFM are present in the first CRISPR of YT1, and the spacers 22-26 of NCFM are present in the second CRISPR of YT1.

Unlike other strains, the *L. acidophilus* YT1 strain consists of two CRISPR regions. Only a portion of the CRISPR coincides with those of other strains and a novel sequence not reported previously is present in the CRISPR. It was identified that the *L. acidophilus* YT1 strain can be clearly identified based on this feature.

Therefore, the inventors have designed a marker capable of specifically detecting the *L. acidophilus* YT1 strain using the difference in the CRISPR structure, which is shown in FIG. 11. More specifically, FIG. 11 shows a primer set capable of specifically detecting *Lactobacillus acidophilus* YT1 and the size of a PCR product obtained by performing PCR using the primer set, analyzed by in silico analysis.

As shown in FIG. 11, they have prepared a marker capable of specifically detecting the *L. acidophilus* YT1 strain by developing a primer including YT1-specific spacers in the first CRISPR region (YT1 CRISPR 1). Specifically, a 20 bp left primer was constructed from the 6th nucleotide to the 25th nucleotide of the spacer 5 region of *L. acidophilus* YT1, and a 20 bp right primer was constructed from the 1st nucleotide to the 20th nucleotide of spacer d region. The *L. acidophilus* YT1 strain could be certainly distinguished with the primer set of the present disclosure.

In addition, the length of a PCR product obtained by performing PCR using the primer set designed according to the present disclosure was analyzed by in silico modeling, and the result is shown in FIG. 11. As a result, the PCR product of *L. acidophilus* YT1 had a length of 320 bp (four 32 bp spacers (spacers a, a, b and c)+five 28 bp dicers (DP5)+27 bp spacer 5 of left primer+20 bp spacer d of right primer).

That is to say, the presence of the *L. acidophilus* YT1 strain in a sample can be detected by using the primer set according to the present disclosure.

In the present disclosure, the most important thing in the preparation of a primer set for discriminating *L. acidophilus* YT1 was to design such that the total length of the primer is 18-23 bp (optimum length 20 bp). In addition, the primers were designed to have a melting temperature ($T_m$) of 57-62° C., specifically 60° C., the maximum difference in $T_m$ between the primers of 5° C. or smaller, and GC % of 35-65%, specifically 50%.

The specificity of a composition of the primer set of SEQ ID NOS: 7 and 15 for the *L. acidophilus* YT1 strain was analyzed through in silico analysis and sequence matching on the NCBI DB. As a result (FIG. 12), it was confirmed that the primer set composition designed in the present disclosure cannot amplify the strains listed in the NCBI database.

Figure 12:
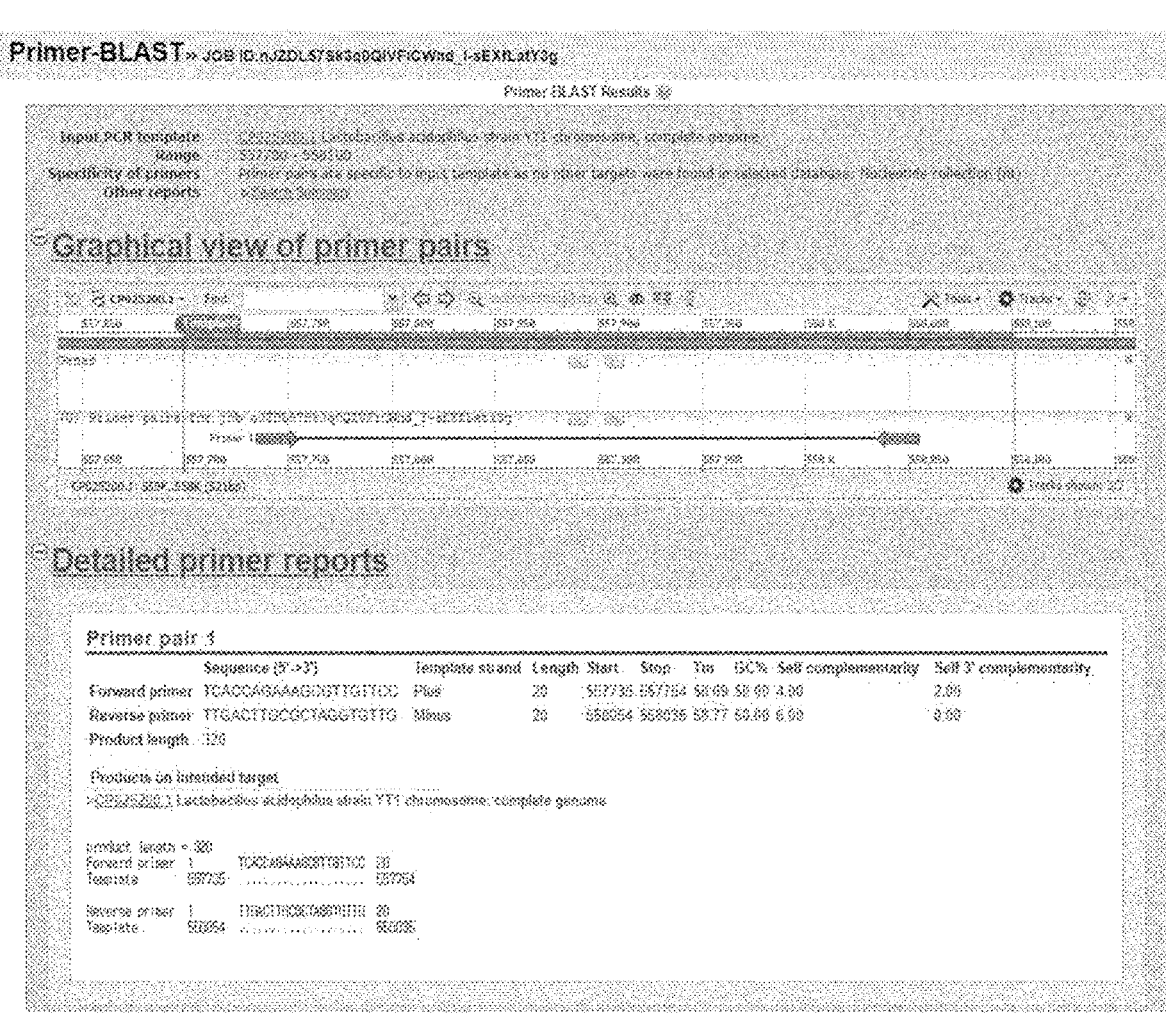
FIG. 12 shows a result of searching a primer set for discriminating a *Lactobacillus acidophilus* YT1 strain (CRISPR_YT1_F, CRISPR_YT1_R) of the present disclosure from the NCBI database using Primer-BLAST in silico.

FIG. 12 shows a result of analyzing the sequence of the primer set for discriminating a *Lactobacillus acidophilus* YT1 strain of the present disclosure from the NCBI database using the sequence search program called Primer-BLAST in silico. On the Primer-BLAST website, PCR template was designated as CP025200.1, forward primer region as 557,700-557,800, and reverse primer region as 558,00-558,100. As the primer parameters, CRISPR_YT1_F was inputted for the forward primer sequence and CRISPR_YT1_F for the reverse primer sequence. The database was designated as "nr". The program was executed with the remaining setting as default setting.

As a result, it was confirmed that the primer set for discriminating the *L. acidophilus* YT1 strain specifically amplifies only the genome sequence of *L. acidophilus* YT1 (Accession No. CP025200.1) from among the sequences listed in the NCBI database. Specifically, it was stated that "Primer pairs are specific to input template as no other targets were found in selected database: Nucleotide collection (nt)" in the "Specificity of primers" section of FIG. 12.

In FIG. 12, it is to be noted that the reverse primer CRISPR_YT1_R is located upstream of the forward primer CRISPR_YT1_F on the genome because the reverse sequence of the genome was used as a primer template. Because Primer-BLAST recognizes the primer located upstream on the genome as the forward primer, the reverse primer is displayed on "Forward primer" and the forward primer is displayed on "Reverse primer".

Test Example 1. 16S rRNA Gene Base Sequence Analysis

1) Comparison of similarity of 16S gene of *Lactobacillus acidophilus* and related species *Lactobacillus acidophilus* is known as the species showing the highest similarity and the 60 sp. strains belonging to *Lactobacillus acidophilus* listed in the NCBI data have 16S rRNA sequence similarity of 97.5-100%. It was identified that *Lactobacillus acidophilus* NCFM and *Lactobacillus acidophilus* EMBS082 exhibit the larges difference in similarity of 97.5%.

Generally, in the 16S rRNA discrimination method, similarity of 97% or higher is judged as the same species. The 16S genes exhibiting similarity to the 16S rRNA gene information of *Lactobacillus acidophilus* NCFM (Accession No. CP000033.3) were searched and compared from the NCBI database. Through BLASTN search from the NCBI NT database, 414 sequences excluding the uncultured strain were found to have similarity of 97% or higher.

With the existing technology of simply comparing the 16S rRNA base sequence, it is highly likely that 354 strains which do not belong to the species *Lactobacillus acidophilus* may be misjudged as *Lactobacillus acidophilus*.

As a result of similarity analysis prior to phylogenetic comparison, besides the strains (60 sp.) belonging to *Lactobacillus acidophilus*, 252 *Lactobacillus helveticus* strains, 33 *Lactobacillus crispatus* strains, 18 *Lactobacillus amylovorus* strains, 16 *Lactobacillus* sp. strains, 9 *Lactobacillus gallinarum* strains, 8 *Lactobacillus kefiranofaciens* strains, 6 *Lactobacillus suntoryeus* strains, 4 *Lactobacillus kitasatonis* strains, 1 *Lactococcus lactis* strain, *Lactobacillus ultunensis*, *Lactobacillus sobrius*, *Lactobacillus fermentum*, *Lactobacillus casei*, Lactobacillusceae *bacterium*, Bacterium ic1256 and *Bacillus pumilus* were identified as strains having 97% or higher similarity to *Lactobacillus acidophilus* NCFM (414 strains in total).

2) Comparison of 16S Gene Genealogy of *Lactobacillus acidophilus* and Related Species FIG. 13 shows the result of analyzing the genealogy of the 16S rRNA sequence of the 414 strains having 97% or higher similarity to *Lactobacillus acidophilus* NCFM identified in 1). In FIG. 13, the sequences other than that of the species *Lactobacillus acidophilus* are shown in red colors and marked with asterisks (*).

That is to say, as a result of conducting phylogenetic comparison as in FIG. 13 by considering the location and arrangement of each base sequence rather than simply comparing the similarity of 16S rRNA base sequence only, only five strains, 3 *Lactobacillus* (*Lactobacillus* sp.) strains and 2 *Lactobacillus kitasatonis* strains, were indistinguishable the species *Lactobacillus acidophilus* (error rate: 7.7%).

Specifically, from the phylogenetic analysis result shown in FIG. 13, it can be seen that *Lactobacillus* (Accession No. EU600905.1, KF952776.1, MH782151.1) and *Lactobacillus kitasatonis* (Accession No. AB186333.1, AB186339.1) strains are in the branch "A", wherein 60 strains belonging to the species *Lactobacillus acidophilus* are classified as one lineage, in the phylogenetic tree.

Accordingly, it was confirmed that, with the current phylogenetic classification of microorganisms based on the 16S rRNA gene information, it is impossible to specifically detect, discriminate and identify only the species *Lactobacillus acidophilus* from the genus *Lactobacillus*.

That is to say, since the 16S rRNA discrimination method classifies even the strains belonging to different species or genus other than the species *Lactobacillus acidophilus* as the species *Lactobacillus acidophilus*, there is limitation in accurately detecting and discriminating the specific strain from an unknown sample. Therefore, for more accurate detection and discrimination, an additional step is necessary.

Test Example 2. PCR Analysis of Composition for Discriminating the Species *Lactobacillus acidophilus* of Example 1

It was investigated whether the primer composition for discriminating the species *Lactobacillus acidophilus* of the present disclosure (primer set of SEQ ID NOS: 1 and 9) shown in FIG. 2 specifically discriminates the species *Lactobacillus acidophilus*.

First, each of *Lactobacillus helveticus* ATCC 13866, *Lactobacillus amylovorus* ATCC 33620, *Lactobacillus acidophilus* ATCC 4356, *Lactobacillus acidophilus* NCFM, *Lactobacillus acidophilus* LA1 and *Lactobacillus acidophilus* YT1 strains was cultured in MRS medium (Difco, 288110) at 37° C. for 18 hours. Then, a colony was recovered from the culture medium of each strain and genomic DNA was extracted using a QIAamp DNA Mini kit (Qiagen, Germany).

Thermal cycling (PCR) was performed for 30 ng of the extracted DNA. For PCR reaction, 30 μL of a reaction mixture wherein 2.0 mM dNTP (Fermentas, USA), 1.0 unit of a thermostable DNA polymerase (e-Taq polymerase, Solgent), 20 pmol CRISPR_LA_uni_F primer (SEQ ID NO: 1), 20 pmol CRISPR_LA_uni_R primer (SEQ ID NO: 9), 20 ng of strain DNA and buffer (10 mM Tris-HCl (pH 8.0), 50 mM KCl, 1.5 mM $MgCl_2$, 0.01% gelatin) were completely mixed was prepared.

PCR reaction was performed using Dyad (Bio-Rad) under the condition of 300 seconds at 95° C. followed by DNA denaturation at 95° C. for 30 seconds, annealing at 60° C. for 30 seconds and extension (DNA polymerization) at 72° C. for 90 seconds. This procedure was repeated for 28 cycles (95° C., 30 seconds (denaturation)→60° C., 30 seconds (reassembly)→72° C., 90 seconds (DNA polymerization)), followed by final synthesis at 72° C. for 300 seconds.

TABLE 1

| PCR reaction solution | Contents (μL) |
|---|---|
| SP Taq | 0.5 |
| 10x SP Taq buffer | 2.5 |
| dNTPs | 2.0 |
| Tuning Buffer | 5.0 |
| Template (strain DNA) | 1.0 |
| Forward primer (5 μM) CRISPR_LA_uni_F primer (SEQ ID NO 1) | 1.0 |
| Reverse primer (5 μM) CRISPR_LA_uni_R primer (SEQ ID NO 9) | 1.0 |
| D.W | 12 |

The amplified amplification product (PCR product) was electrophoresed on 1.2% agarose gel, and polymorphic DNA bands were detected by staining with Safeview (iNtRON Biotechnology, Korea) and irradiating UV and then imaged with the Gel-Doc system (Bio-Rad). The result is shown in FIG. 14.

FIG. 14 shows the result of performing PCR for different strains (*Lactobacillus helveticus* ATCC 13866, *Lactobacillus amylovorus* ATCC 33620, *Lactobacillus acidophilus* ATCC 4356, *Lactobacillus acidophilus* NCFM, *Lactobacillus acidophilus* CB_LA1 and *Lactobacillus acidophilus* YT1) using the primer set represented by SEQ ID NOS: 1 and 9 of the present disclosure, and FIG. 15 shows the result of repeating the process of purifying the PCR amplification product obtained by performing PCR for the *Lactobacillus acidophilus* YT1 strain using the primer set represented by SEQ ID NOS: 1 and 9 of the present disclosure and then analyzing the same by agarose gel electrophoresis twice (Uni-a, Uni-b).

M denotes a DNA size marker (Sizer™ 100 bp DNA marker (Cat. No. 24073), 1 denotes *Lactobacillus helveticus* ATCC 13866, 2 denotes *Lactobacillus amylovorus* ATCC 33620, 3 denotes *Lactobacillus acidophilus* ATCC 4356, 4 denotes *Lactobacillus acidophilus* NCFM strain, 5 denotes

*Lactobacillus acidophilus* LA1 (also referred to as CB_LA1), and 6 denotes *Lactobacillus acidophilus* YT1.

As seen from FIG. 14, it was confirmed that the composition for discriminating the species *Lactobacillus acidophilus* including the primers represented by SEQ ID NO: 1 and SEQ ID NO: 9 of the present disclosure amplified the DNA fragment with a size of about 267 bp.

It was confirmed through genome analysis that all the species *Lactobacillus acidophilus* share spacers 1-5 of the CRISPR region and a primer composition capable of discriminating all the species *Lactobacillus acidophilus* was completed by designing and preparing a universal primer (a primer set including forward primer of SEQ ID NO: 1 and a reverse primer of SEQ ID NO: 9, see FIG. 2) capable of amplifying the spacers 1-5.

If the target sequence (CRISPR region) of the strain belonging to the species *Lactobacillus acidophilus* is amplified using the primer composition according to the present disclosure, a PCR product with a size of 267 bp can be obtained.

When considering the slight difference in gel electrophoresis (high resolution of one base is not achieved in electrophoresis), the detection of a PCR product with a size of 200-300 bp (specifically 260-280 bp) is included in the scope of the present disclosure because the result is derived from the 267 bp-sized PCR product for the CRISPR region of the amplified *Lactobacillus acidophilus* strain.

Accordingly, although it is desired that the PCR product has a size of precisely 267 bp, when considering the various conditions described above (including the regions that can be detected with the marker), a PCR product size of 200-300 bp, specifically 260-280 bp, may be discriminated as *Lactobacillus acidophilus*.

To demonstrate this, the DNA base sequence was investigated only for the PCR product of *Lactobacillus acidophilus*.

Unlike *Lactobacillus acidophilus*, no amplified DNA fragment was observed for *Lactobacillus helveticus* ATCC 13866 or *Lactobacillus amylovorus* ATCC 33620.

Accordingly, the primers represented by SEQ ID NO: 1 and SEQ ID NO: 9 according to the present disclosure may be used as a composition for discriminating the species *Lactobacillus acidophilus* quickly and accurately because an amplicon is produced only for *Lactobacillus acidophilus*.

FIG. 15 shows a result of purifying a product (amplicon) obtained by performing PCR using the primer composition according to the present disclosure and using the DNA of the *Lactobacillus acidophilus* YT1 strain as a template and analyzing its sequence. The amplification product for *Lactobacillus acidophilus* was measured as 267 bp including primers. The amplified sequence is as follows.

```
                                  [SEQ ID NO 17]
TAAAAGCTACAGAGTTACCATCGAGGATCACC

TCCACTTTCGTGGAGAAAATTGGAATCTCATC

GTAAGAAATAAGTCGCATATAGGATCACCTCC

ACATACGTGGAGAAAATCCTTTTCCTAGGATC

TTCATAAGCTTCTCGCCAGGATCACCTCCACA

TACGTGGAGAAAATATCGTAGTCAATCTCGTA
```

-continued
```
CTTAAAACCACCCTGGGATCACCTCCACATAC

GTGGAGAAAATCCAGGTTGACTTGCGCTAGGT

GTTGCATCAAT
```

Since all the strains belonging to the species *Lactobacillus acidophilus* share the spacers 1-5 of the CRISPR region, the same amplicons are produced when amplification is performed in silico using the primer composition according to the present disclosure. As shown in FIG. 15, when the product (amplicon) obtained by performing PCR using the primer composition according to the present disclosure and the DNA of the *Lactobacillus acidophilus* YT1 strain as a template was purified and re-sequencing was performed, it was confirmed to match with the sequence actually present on the genome.

Especially, it was identified that the base sequence read length of the amplified PCR product for *Lactobacillus acidophilus* was 267 bp and corresponded 100% to the base sequence predicted from the genome. That is to say, although the amplified sequence seemed to have a size of about 270 bp as a result of electrophoresis, it actually had a length of 267 bp, matching perfectly with the predicted length.

Through this, it can be seen that a composition for discriminating the species *Lactobacillus acidophilus*, which includes the primers represented by SEQ ID NO: 1 and SEQ ID NO: 9 of the present disclosure, can clearly distinguish all the strains belonging to *Lactobacillus acidophilus* from other sp. strains.

Accordingly, it was confirmed again that the primers represented by SEQ ID NO: 1 and SEQ ID NO: 9 according to the present disclosure can be used as a composition for discriminating the species *Lactobacillus acidophilus* for producing an amplicon for *Lactobacillus acidophilus* only quickly and accurately.

Test Example 3. In Silico Analysis of Composition for Discriminating the Species *Lactobacillus acidophilus* of Example 1

From among the strains identified through the phylogenetic analysis in Test Example 1 as *Lactobacillus acidophilus* owing to high similarity to *Lactobacillus acidophilus* NCFM, the *Lactobacillus kitasatonis* strains DSM 16761 (Genbank Accession No. GCA_001434435.1) and JCM 1039 (Genbank Accession No. GCA_000615285.1) listed in the NCBI database were prepared.

For the strains, it was investigated through in silico analysis whether they have binding sites for a primer set of SEQ ID NOS: 2 and 10, a primer set of SEQ ID NOS: 3 and 11, a primer set of SEQ ID NOS: 4 and 12, a primer set of SEQ ID NOS: 5 and 13 and a primer set of SEQ ID NOS: 6 and 14 in addition to the primer set including the primers represented by SEQ ID NOS: 1 and 9, which was designed in Example 1, and how much they match with the spacers 1-5 of the CRISPR region shared by the species *Lactobacillus acidophilus*.

As a result of investigating the primer sets designed in the present disclosure (SEQ ID NOS: 1 and 9, SEQ ID NOS: 2 and 10, SEQ ID NOS: 3 and 11, SEQ ID NOS: 4 and 12, SEQ ID NOS: 5 and 13, and SEQ ID NOS: 6 and 14) for the genome of *Lactobacillus kitasatonis* DSM 16761 (Genbank Accession No. GCA_001434435.1) and JCM 1039 (Genbank Accession No. GCA_000615285.1) listed in the NCBI database, no binding site was observed for the primer sets, suggesting that there is no possibility of the production of PCR products. In addition, no sequence matching with the PCR amplification products with a size of about 100-300 bp (267 bp, 209 bp, 147 bp, 207 bp, 148 bp and 146 bp, respectively), obtained from *Lactobacillus acidophilus*, was observed.

In addition, it was confirmed that no match was observed for any of the spacers 1-5 of the CRISPR region shared by the species *Lactobacillus acidophilus*.

Taken together, it can be seen that even the *Lactobacillus kitasatonis*, which has a 16S rRNA gene very similar to that of *Lactobacillus acidophilus* and is identified as *Lactobacillus acidophilus* by the 16S rRNA gene-based discrimination method, can be clearly distinguished and discriminated as not belonging to *Lactobacillus acidophilus* with the primer composition of the present disclosure. It can be seen that the primer composition according to the present disclosure can more accurately discriminate, distinguish and detect the strains belonging to the species *Lactobacillus acidophilus* from the other strains than the existing 16S rRNA gene discrimination method, and that the primer composition of the present disclosure may be used to accurately identify the presence of *Lactobacillus acidophilus* in a product or a sample and to determine where an unknown strain belongs to *Lactobacillus acidophilus*.

Test Example 4. PCR Analysis of Composition for Discriminating Individual *Lactobacillus acidophilus* Strains of Example 4 (1)

It was investigated whether the composition for discriminating individual *Lactobacillus acidophilus* strains according to the present disclosure (FIGS. 6-7) can specifically discriminate *L. acidophilus* strains, especially the *L. acidophilus* LA1 strain.

The result of analyzing the sequence of the primer set for discriminating individual *L. acidophilus* strains according to the present disclosure in silico by referring to the NCBI database using the sequence search program called BLASTN in the same way as described in Example 4 is shown in Tables 2-9.

TABLE 2

| | >> region for left primer | | | | |
|---|---|---|---|---|---|
| query | NCFM. spacer5 | NCFM. spacer5 | NCFM. spacer5 | NCFM. spacer5 | NCFM. spacer5 |
| sbjct | CP010432.1 | CP005926.2 | CP000033.3 | XM_0202 60620.1 | LL191556.1 |
| qlen | 33 | 33 | 33 | 33 | 33 |
| blast_ident | 100 | 100 | 100 | 95.652 | 100 |
| blast_cov | 100 | 100 | 100 | 70 | 58 |
| qstart | 1 | 1 | 1 | 10 | 7 |
| qend | 33 | 33 | 33 | 32 | 25 |
| sstart | 1541590 | 1540886 | 1541311 | 2410 | 33751 |
| send | 1541622 | 1540918 | 1541343 | 2432 | 33769 |
| strand | plus | plus | plus | minus | minus |
| evalue | 2.42E-08 | 2.42E-08 | 2.42E-08 | 5.5 | 5.5 |
| align_ident | 100 | 100 | 100 | 78.788 | 78.788 |
| align_match | 33 | 33 | 33 | 26 | 26 |
| align_gap | 0 | 0 | 0 | 0 | 2 |
| xstart | 1541590 | 1540886 | 1541311 | 2409 | 33743 |
| xend | 1541622 | 1540918 | 1541343 | 2441 | 33775 |
| qry_align | CCAGGTTGA CTTGCGCTA GGTGTTGCA TCAATA (SEQ ID NO: 22) | CCAGGTTGA CTTGCGCTA GGTGTTGCA TCAATA (SEQ ID NO: 22) | CCAGGTTG ACTTGCGCT AGGTGTTGC ATCAATA (SEQ ID NO: 22) | CCAGGTTG ACTTGCGCT AGGTGTTGC ATCAATA (SEQ ID NO: 22) | CCAGGT--TG ACTTGCGCT AGGTGTTGC ATCAATA (SEQ ID NO: 22) |

TABLE 2 -continued

| | >> region for left primer | | | | |
|---|---|---|---|---|---|
| query | NCFM. spacer5 | NCFM. spacer5 | NCFM. spacer5 | NCFM. spacer5 | NCFM. spacer5 |
| sbj_ align | CCAGGTTGA CTTGCGCTA GGTGTTGCA TCAATA (SEQ ID NO: 22) | CCAGGTTGA CTTGCGCTA GGTGTTGCA TCAATA (SEQ ID NO: 22) | CCAGGTTG ACTTGCGCT AGGTGTTGC ATCAATA (SEQ ID NO: 22) | GCTGGTGA CCTTGCGCT AGGTGTTGC AACAATT (SEQ ID NO: 22) | --AGCTCCTG ACTTGCGCT AGGTGTTG AAAAAACA (SEQ ID NO: 22) |
| align_ code | OOOOOOOO OOOOOOOO OOOOOOOO OOOOOOOO O | OOOOOOOO OOOOOOOO OOOOOOOO OOOOOOOO O | OOOOOOOO OOOOOOOO OOOOOOOO OOOOOOOO O | /O/OOO///OO OOOOOOOO OOOOOOOOO/ OOOO/ | --OO/O--OOO OOOOOOOO OOOOOOOOO/ O//OO/O |
| sbjct_ title | *Lactobacillus acidophilus* strain FSI4, complete genome | *Lactobacillus acidophilus* La-14, complete genome | *Lactobacillus acidophilus* NCFM, complete genome | *Talaromyces atroroseus* hypotheti-cal Protein mRNA | *Heligmosomoides polygyrus* genome assembly H_bakeri_ Edinburgh, scaffold HPBE_ Scaffold 0003172 |

[TABLE 3]

| query | >>region for right primer 1 | | | | | |
|---|---|---|---|---|---|---|
| | NCFM.spacer20 | NCFM.spacer20 | NCFM.spacer20 | NCFM.spacer20 | NCFM.spacer20 | NCFM.spacer20 |
| sbjct | CP010432.1 | CP006811.1 | CP005926.2 | FN298497.1 | CP000033.3 | AE017198.1 |
| qlen | 33 | 33 | 33 | 33 | 33 | 33 |
| blast_ident | 100 | 100 | 100 | 100 | 100 | 100 |
| blast_cov | 100 | 100 | 100 | 100 | 100 | 100 |
| qstart | 1 | 1 | 1 | 1 | 1 | 1 |
| qend | 33 | 33 | 33 | 33 | 33 | 33 |
| sstart | 233474 | 301267 | 233173 | 273991 | 233176 | 288059 |
| send | 233506 | 301299 | 233205 | 274023 | 233208 | 288091 |
| strand | minus | minus | minus | minus | minus | minus |
| evalue | 2.42E-08 | 2.42E-08 | 2.42E-08 | 2.42E-08 | 2.42E-08 | 2.42E-08 |
| align_ident | 100 | 100 | 100 | 100 | 100 | 100 |
| align_match | 33 | 33 | 33 | 33 | 33 | 33 |
| align_gap | 0 | 0 | 0 | 0 | 0 | 0 |
| xstart | 233474 | 301267 | 233173 | 273991 | 233176 | 288059 |
| xend | 233506 | 301299 | 233205 | 274023 | 233208 | 288091 |
| qry_align | TCAAGAT CAACCAT TCATTTG CCACGCA AATCG (SEQ ID NO: 26) | TCAAGAT CAACCAT TCATTTG CCACGCA AATCG (SEQ ID NO: 26) | TCAAGAT CAACCAT TCATTTG CCACGCA AATCG (SEQ ID NO: 26) | TCAAGAT CAACCAT TCATTTG CCACGCA AATCG (SEQ ID NO: 26) | TCAAGAT CAACCAT TCATTTG CCACGCA AATCG (SEQ ID NO: 26) | TCAAGATC AACCATTC ATTTGCCA CGCAAATC G (SEQ ID NO: 26) |

[TABLE 3]-continued

| | >>region for right primer 1 | | | | | |
|---|---|---|---|---|---|---|
| query | NCFM.spacer20 | NCFM.spacer20 | NCFM.spacer20 | NCFM.spacer20 | NCFM.spacer20 | NCFM.spacer20 |
| sbj_align | TCAAGAT CAACCAT TCATTTG CCACGCA AATCG (SEQ ID NO: 26) | TCAAGAT CAACCAT TCATTTG CCACGCA AATCG (SEQ ID NO: 26) | TCAAGAT CAACCAT TCATTTG CCACGCA AATCG (SEQ ID NO: 26) | TCAAGAT CAACCAT TCATTTG CCACGCA AATCG (SEQ ID NO: 26) | TCAAGAT CAACCAT TCATTTG CCACGCA AATCG (SEQ ID NO: 26) | TCAAGATC AACCATTC ATTTGCCA CGCAAATC G (SEQ ID NO: 26) |
| align_code | 000000 000000 000000 000000 000000 000 | 000000 000000 000000 000000 000000 000 | 000000 000000 000000 000000 000000 000 | 000000 000000 000000 000000 000000 000 | 000000 000000 000000 000000 000000 000 | 0000000 0000000 0000000 0000000 00000 |
| sbjct_title | Lactobacillus acidophilus strain FSI4, complete genome | Lactobacillus johnsonii N6.2, complete genome | Lactobacillus acidophilus La-14, complete genome | Lactobacillus johnsonii FI9785, complete genome | Lactobacillus acidophilus NCFM, complete genome | Lactobacillus johnsonii NCC 533, complete genome |

[TABLE 4]

| | >>region for right primer 2 | | | | | |
|---|---|---|---|---|---|---|
| query | NCFM.spacer20 | NCFM.spacer20 | NCFM.spacer20 | NCFM.spacer20 | NCFM.spacer20 | NCFM.spacer20 |
| sbjct | CP016400.1 | CP002464.1 | CP002609.1 | CP002559.1 | CP002338.1 | AP014808.1 |
| qlen | 33 | 33 | 33 | 33 | 33 | 33 |
| blast_ident | 96.97 | 96.97 | 96.875 | 96.875 | 96.875 | 96.154 |
| blast_coy | 100 | 100 | 97 | 97 | 97 | 79 |
| qstart | 1 | 1 | 2 | 2 | 2 | 8 |
| qend | 33 | 33 | 33 | 33 | 33 | 33 |
| sstart | 1608361 | 297768 | 242626 | 239350 | 266408 | 308621 |
| send | 1608393 | 297800 | 242657 | 239381 | 266439 | 308646 |
| strand | minus | minus | minus | minus | minus | minus |
| evalue | 5.89E-06 | 5.89E-06 | 2.33E-05 | 2.33E-05 | 2.33E-05 | 0.089 |
| align_ident | 96.97 | 96.97 | 93.939 | 93.939 | 93.939 | 87.879 |
| align_match | 32 | 32 | 31 | 31 | 31 | 29 |
| align_gap | 0 | 0 | 0 | 0 | 0 | 0 |
| xstart | 1608361 | 297768 | 242626 | 239350 | 266408 | 308621 |
| xend | 1608393 | 297800 | 242658 | 239382 | 266440 | 308653 |
| qry_align | TCAAGAT CAACCAT TCATTTG CCACGCA AATCG (SEQ ID NO: 26) | TCAAGAT CAACCAT TCATTTG CCACGCA AATCG (SEQ ID NO: 26) | TCAAGAT CAACCAT TCATTTG CCACGCA AATCG (SEQ ID NO: 26) | TCAAGAT CAACCAT TCATTTG CCACGCA AATCG (SEQ ID NO: 26) | TCAAGA TCAACC ATTCAT TTGCCA CGCAAA TCG (SEQ ID NO: 26) | TCAAGATC AACCATTC ATTTGCCA CGCAAATC G (SEQ ID NO: 26) |

[TABLE 4]-continued

| | >>region for right primer 2 | | | | | |
|---|---|---|---|---|---|---|
| query | NCFM.spacer20 | NCFM.spacer20 | NCFM.spacer20 | NCFM.spacer20 | NCFM.spacer20 | NCFM.spacer20 |
| sbj_align | TCAAGAT CAACCAT TTATTTG CCACGCA AATCG (SEQ ID NO: 27) | TCAAGAT CAACCAT TTATTTG CCACGCA AATCG (SEQ ID NO: 27) | CCAAGAT CAACCAT TTATTTG CCACGCA AATCG (SEQ ID NO: 28) | CCAAGAT CAACCAT TTATTTG CCACGCA AATCG (SEQ ID NO: 28) | CCAAGA TCAACC ATTTAT TTGCCA CGCAAA TCG (SEQ ID NO: 28) | TCAGAACC AACCATTC ATTTGTCA CGCAAATC G (SEQ ID NO: 29) |
| align_code | 0000000 0000000 0/00000 0000000 00000 | 0000000 0000000 0/00000 0000000 00000 | /000000 0000000 0/00000 0000000 00000 | /000000 0000000 0/00000 0000000 00000 | /000000 0000000 0/00000 0000000 00000 | 000//0/00 000000000 000/00000 000000 |
| sbjct_title | *Lactobacil- lus johnsonii strain BS15, complete genome* | *Lactobacillus johnsonii DPC6026, complete genome* | *Lactobacillus amylovorus GRL1118, complete genome* | *Lactobacillus amylovorus strain 30SC, complete genome* | *Lactobacillus amylovorus GRL1112, complete genome* | *Lactobacillus acetotolerans DNA, complete genome, strain: NBRC 13120* |

[TABLE 5]

| | >>region for right primer 3 | | | | | |
|---|---|---|---|---|---|---|
| query | NCFM.spacer20 | NCFM.spacer20 | NCFM.spacer20 | NCFM.spacer20 | NCFM.spacer20 | NCFM.spacer20 |
| sbjct | CP002764.1 | LM149353.1 | CP016827.1 | XM_008236577.2 | XM_008236576.2 | CP012890.1 |
| qlen | 33 | 33 | 33 | 33 | 33 | 33 |
| blast_ident | 93.103 | 100 | 95.652 | 100 | 100 | 95.652 |
| blast_coy | 88 | 61 | 70 | 58 | 58 | 70 |
| qstart | 2 | 2 | 1 | 5 | 5 | 1 |
| qend | 30 | 21 | 23 | 23 | 23 | 23 |
| sstart | 2053473 | 27748 | 1189326 | 3966 | 47 | 308956 |
| send | 2053501 | 27767 | 1189348 | 3984 | 65 | 308978 |
| strand | minus | minus | plus | minus | minus | plus |
| evalue | 0.35 | 1.4 | 5.5 | 5.5 | 5.5 | 5.5 |
| align_ident | 87.879 | 63.636 | 84.848 | 69.697 | 69.697 | 84.848 |
| align_match | 29 | 21 | 28 | 23 | 23 | 28 |
| align_gap | 0 | 0 | 0 | 0 | 0 | 0 |
| xstart | 2053470 | 27736 | 1189326 | 3956 | 37 | 308956 |
| xend | 2053502 | 27768 | 1189358 | 3988 | 69 | 308988 |
| qry_align | TCAAGAT CAACCAT TCATTTG CCACGCA AATCG (SEQ ID NO: 26) | TCAAGAT CAACCAT TCATTTG CCACGCA AATCG (SEQ ID NO: 26) | TCAAGAT CAACCAT TCATTTG CCACGCA AATCG (SEQ ID NO: 26) | TCAAGAT CAACCAT TCATTTG CCACGCA AATCG (SEQ ID NO: 26) | TCAAGAT CAACCAT TCATTTG CCACGCA AATCG (SEQ ID NO: 26) | TCAAGATC AACCATTC ATTTGCCA CGCAAATC G (SEQ ID NO: 26) |

[TABLE 5]-continued

| >>region for right primer 3 | | | | | |
|---|---|---|---|---|---|
| query | NCFM.spacer20 | NCFM.spacer20 | NCFM.spacer20 | NCFM.spacer20 | NCFM.spacer20 | NCFM.spacer20 |
| sbj_align | CCAAGAT CAACCTT TCGTTTG CCACGCA AACCG (SEQ ID NO: 29) | GCAAGAT CAACCAT TCATTTG ATTTTCT GTCAA (SEQ ID NO: 30) | TCAAGAT CAACCTT TCATTTG CCGTGCT AACCG (SEQ ID NO: 31) | GTTGGAT CAACCAT TCATTTG CCGCAA AACTGT (SEQ ID NO: 32) | GTTGGAT CAACCAT TCATTTG CCGCAAA ACTGT (SEQ ID NO: 32) | TCAAGATC AACCTTTC ATTTGCCG TGCTAACC G (SEQ ID NO: 31) |
| align_code | /000000 00000/0 00/0000 0000000 00/00 | /000000 0000000 0000000 /////0/ ///// | 0000000 00000/0 0000000 00//00/ 00/00 | ////000 0000000 0000000 00/0//0 0/0// | ////000 0000000 0000000 00/0//0 0/0// | 00000000 0000/000 0000000/ /00/00/0 0 |
| sbjct_title | *Lactobacillus kefiranofaciens ZW3, complete genome* | *Schistosoma mattheei genome assembly S_mattheei_Denwood, scaffold SMTD_scaffold0000035* | *Lactobacillus helveticus strain D76, complete genome* | PREDICTED: *Prunusmume* ABC transporter C family member 10-like (LOC1033 33683), mRNA | PREDICTED: *Prunusmume* ABC transporter C family member 10-like (LOC10333 3682), mRNA | *Lactobacillus gallinarum strain HFD4, complete genome* |

[TABLE 6]

| >>region for right primer 4 | | | | | |
|---|---|---|---|---|---|
| query | NCFM.spacer20 | NCFM.spacer20 | NCFM.spacer20 | NCFM.spacer20 | NCFM.spacer20 | NCFM.spacer20 |
| sbjct | CP012381.1 | CP011386.1 | XM_012224715.1 | CP009907.1 | XM_011037590.1 | LN005319.1 |
| qlen | 33 | 33 | 33 | 33 | 33 | 33 |
| blast_ident | 95.652 | 95.652 | 100 | 95.652 | 100 | 100 |
| blast_coy | 70 | 70 | 58 | 70 | 58 | 58 |
| qstart | 1 | 1 | 2 | 1 | 6 | 6 |
| qend | 23 | 23 | 20 | 23 | 24 | 24 |
| sstart | 251207 | 226916 | 1501 | 426446 | 319 | 825 |
| send | 251229 | 226938 | 1519 | 426468 | 337 | 843 |
| strand | minus | minus | plus | minus | plus | minus |
| evalue | 5.5 | 5.5 | 5.5 | 5.5 | 5.5 | 5.5 |
| align_ident | 84.848 | 84.848 | 69.697 | 84.848 | 78.788 | 66.667 |
| align_match | 28 | 28 | 23 | 28 | 26 | 22 |
| align_gap | 0 | 0 | 0 | 0 | 2 | 0 |
| xstart | 251197 | 226906 | 1500 | 426436 | 314 | 816 |
| xend | 251229 | 226938 | 1532 | 426468 | 346 | 848 |
| qry_align | TCAAGAT CAACCAT TCATTTG CCACGCA AATCG (SEQ ID NO: 26) | TCAAGAT CAACCAT TCATTTG CCACGCA AATCG (SEQ ID NO: 26) | TCAAGAT CAACCAT TCATTTG CCACGCA AATCG (SEQ ID NO: 26) | TCAAGAT CAACCAT TCATTTG CCACGCA AATCG (SEQ ID NO: 26) | TCAAG--A TCAACCAT TCATTTGC CACGCAAA TCG (SEQ ID NO: 26) | TCAAGATC AACCATTC ATTTGCCA CGCAAATC G (SEQ ID NO: 26) |
| sbj_align | TCAAGAT CAACCTT TCATTTG CCGTGCT | TCAAGAT CAACCTT TCATTTG CCGTGCT | CCAAGAT CAACCAT TCATTTC TCAAACT | TCAAGAT CAACCTT TCATTTG CCGTGCT | --AAGCCA TCAACCAT TCATTTGC CAATACAA | AACGCATC AACCATTC ATTTGCCA TTCGACTA |

[TABLE 6]-continued

>>region for right primer 4

| query | NCFM.spacer20 | NCFM.spacer20 | NCFM.spacer20 | NCFM.spacer20 | NCFM.spacer20 | NCFM.spacer20 |
|---|---|---|---|---|---|---|
| | AACCG (SEQ ID NO: 31) | AACCG (SEQ ID NO: 31) | ACCAA | AACCG (SEQ ID NO: 31) | TCA (SEQ ID NO: 33) | T (SEQ ID NO: 34) |
| align_code | 0000000 00000/0 0000000 00//00/ 00/00 | 0000000 00000/0 0000000 00//00/ 00/00 | /000000 0000000 000000/ /00//0/ 0//// | 0000000 00000/0 0000000 00//00/ 00/00 | --000--0 00000000 00000000 00////00 00/ | /////0000 000000000 000000//0 /0/0// |
| sbjct_title | *Lactobacillus helveticus* strain CAUH18, complete genome | *Lactobacillus helveticus* strain MB2-1, complete genome | PREDICTED: *Jatrophacurcas* probable inactive receptor kinase At2g26730 (LOC105640414), | *Lactobacillus helveticus* strain KLDS1.8701, complete genome | PREDICTED: *Populus euphratica* peptide-N4-(N-acetyl-beta-gluco saminyl) asparagine amidase A-like (LOC10513 | *Spirometra erinaceieuropaei* genome assembly S_erinaceieuropaei, scaffold SPER_scaffold0005269 |

[TABLE 7]

>>region for right primer 5

| query | NCFM.spacer20 | NCFM.spacer20 | NCFM.spacer20 | NCFM.spacer20 | NCFM.spacer20 | NCFM.spacer20 |
|---|---|---|---|---|---|---|
| sbjct | LM433701.1 | LL911802.1 | XM_008611536.1 | XM_008611535.1 | XM_007218824.1 | CP002427.1 |
| qlen | 33 | 33 | 33 | 33 | 33 | 33 |
| blast_ident | 100 | 100 | 100 | 100 | 100 | 95.652 |
| blast_coy | 58 | 58 | 58 | 58 | 58 | 70 |
| qstart | 7 | 12 | 2 | 2 | 5 | 1 |
| qend | 25 | 30 | 20 | 20 | 23 | 23 |
| sstart | 16932 | 11466 | 732 | 681 | 3396 | 214426 |
| send | 16950 | 11484 | 750 | 699 | 3414 | 214448 |
| strand | minus | plus | minus | minus | minus | minus |
| evalue | 5.5 | 5.5 | 5.5 | 5.5 | 5.5 | 5.5 |
| align_ident | 69.697 | 60.606 | 69.697 | 69.697 | 69.697 | 84.848 |
| align_match | 23 | 20 | 23 | 23 | 23 | 28 |
| align_gap | 0 | 0 | 1 | 1 | 0 | 0 |
| xstart | 16924 | 11455 | 719 | 668 | 3386 | 214416 |
| xend | 16956 | 11487 | 751 | 700 | 3418 | 214448 |
| qry_align | TCAAGAT CAACCAT TCATTTG CCACGCA AATCG (SEQ ID NO: 26) | TCAAGA TCAACC ATTCAT TTGCCA CGCAAA TCG (SEQ ID NO: 26) | TCAAGAT CAACCAT TCATTTG CCACGCA AATCG- (SEQ ID NO: 35) | TCAAGAT CAACCAT TCATTTG CCACGCA AATCG- (SEQ ID NO: 35) | TCAAGA TCAACC ATTCAT TTGCCA CGCAAA TCG (SEQ ID NO: 26) | TCAAGATC AACCATTC ATTTGCCA CGCAAATC G (SEQ ID NO: 26) |
| sbj_align | GCTCAGT CAACCAT TCATTTG CCACTCT GACCT (SEQ ID NO: 36) | ATTTAT CAACC TTTGGC ATTCAT TTGCCA CGCAAA CGT (SEQ ID NO: 37) | ACAAGAT CAACCAT TCATTT- TCGTTTA GACCTT (SEQ ID NO: 38) | ACAAGAT CAACCAT TCATTT- TCGTTTA GACCTT (SEQ ID NO: 38) | GTTGGA TCAACC ATTCAT TTGCCG CAAAAC TGT (SEQ ID NO: 32) | TCAAGATC AACCTTTC ATTTGCCG TGCTAACC G (SEQ ID NO: 31) |

[TABLE 7]-continued

| | >>region for right primer 5 | | | | | |
|---|---|---|---|---|---|---|
| query | NCFM.spacer20 | NCFM.spacer20 | NCFM.spacer20 | NCFM.spacer20 | NCFM.spacer20 | NCFM.spacer20 |
| align_code | /0////000<br>000000000<br>0000000/0<br>//0/0/ | //////0<br>////000<br>0000000<br>0000000<br>00/// | /000000<br>0000000<br>000000-<br>/0////0<br>/0/0/- | /000000<br>0000000<br>000000-<br>/0////0<br>/0/0/- | ////000<br>0000000<br>0000000<br>00/0//0<br>0/0// | 00000000<br>0000/000<br>0000000/<br>/00/00/0<br>0 |
| sbjct_title | *Nippostrongylus brasiliensis* genome assembly N_brasil-iensis_RM07_v | *Schistocephalus solidus* genome assembly S_solidus_NST_G2, | *Saprolegnia diclina* VS20 hypothetical protein rnRNA | *Saprolegnia diclina* VS20 hypothetical protein, variant rnRNA | *Primus persica* hypothetical protein (PRUPE_ppa-000197mg) | *Lactobacillus helvelicus* H9, complete genome |

[TABLE 8]

| | >>region for right primer 6 | | | | | |
|---|---|---|---|---|---|---|
| query | NCFM.spacer20 | NCFM.spacer20 | NCFM.spacer20 | NCFM.spacer20 | NCFM.spacer20 | NCFM.spacer20 |
| sbjct | XM_002316157.2 | CP002081.1 | CP003799.1 | FQ310506.3 | CP002429.1 | CP000517.1 |
| qlen | 33 | 33 | 33 | 33 | 33 | 33 |
| blast_ident | 100 | 95.652 | 95.652 | 100 | 95.652 | 95.652 |
| blast_coy | 58 | 70 | 70 | 58 | 70 | 70 |
| qstart | 6 | 1 | 1 | 1 | 1 | 1 |
| qend | 24 | 23 | 23 | 19 | 23 | 23 |
| sstart | 214 | 2121640 | 242872 | 12901448 | 245193 | 255376 |
| send | 232 | 2121662 | 242894 | 12901466 | 245215 | 255398 |
| strand | plus | plus | minus | minus | minus | minus |
| evalue | 5.5 | 5.5 | 5.5 | 5.5 | 5.5 | 5.5 |
| align_ident | 72.727 | 84.848 | 84.848 | 75.758 | 84.848 | 84.848 |
| align_match | 24 | 28 | 28 | 25 | 28 | 28 |
| align_gap | 0 | 0 | 0 | 1 | 0 | 0 |
| xstart | 209 | 2121640 | 242862 | 12901434 | 245183 | 255366 |
| xend | 241 | 2121672 | 242894 | 12901466 | 245215 | 255398 |
| qry_align | TCAAGAT CAACCAT TCATTTG CCACGCA AATCG (SEQ ID NO: 26) | TCAAGAT CAACCAT TCATTTG CCACGCA AATCG (SEQ ID NO: 26) | TCAAGAT CAACCAT TCATTTG CCACGCA AATCG (SEQ ID NO: 26) | TCAAGAT CAACCAT TCATT-TG CCACGCA AATCG | TCAAGAT CAACCAT TCATTTG CCACGCA AATCG (SEQ ID NO: 26) | TCAAGAT CAACCAT TCATTTG CCACGCA AATCG (SEQ ID NO: 26) |
| sbj_align | AAACCAT CAACCAT TCATTTG CCAATAC AATCA (SEQ ID NO: 39) | TCAAGAT CAACCTT TCATTTG CCGTGCT AACCG (SEQ ID NO: 31) | TCAAGAT CAACCTT TCATTTG CCGTGCT AACCG (SEQ ID NO: 31) | TCAAGAT CAACCAT TCATTAA GCCCTGC TTGCC- (SEQ ID NO: 40) | TCAAGAT CAACCTT TCATTTG CCGTGCT AACCG (SEQ ID NO: 31) | TCAAGAT CAACCTT TCATTTG CCGTGCT AACCG (SEQ ID NO: 31) |
| aligncode | //0//00 0000000 0000000 000//// 0000/ | 0000000 00000/0 0000000 00//00/ 00/00 | 0000000 00000/0 0000000 00//00/ 00/00 | 0000000 0000000 00000-/ 000//00 ////0- | 0000000 0000000 0000000 00//00/ 00/00 | 0000000 00000/0 0000000 00//00/ 00/00 |

[TABLE 8]-continued

| | >>region for right primer 6 | | | | | |
|---|---|---|---|---|---|---|
| query | NCFM.spacer20 | NCFM.spacer20 | NCFM.spacer20 | NCFM.spacer20 | NCFM.spacer20 | NCFM.spacer20 |
| sbjct_title | *Populus trichocarpa* hypothetical protein (POPTR_0010s19250g) mRNA, | *Lactobacillus helveticus* CNRZ32, complete genome | *Lactobacillus helveticus* R0052, complete genome | *Dicentrarchus labrax* chromosome sequence corresponding to linkage | *Lactobacillus helveticus* H10, complete genome | *Lactobacillus helveticus* DPC 4571, complete genome |

[TABLE 9]

| | >>region for right primer 7 | | | |
|---|---|---|---|---|
| query | NCFM.spacer20 | NCFM.spacer20 | NCFM.spacer20 | NCFM.spacer20 |
| sbjct | BX248127.9 | BX119963.5 | Z38063.1 | U34257.1 |
| qlen | 33 | 33 | 33 | 33 |
| blast_ident | 100 | 95.652 | 95.652 | 95.652 |
| blast_coy | 58 | 70 | 70 | 70 |
| qstart | 3 | 8 | 1 | 1 |
| qend | 21 | 30 | 23 | 23 |
| sstart | 22022 | 19894 | 1020 | 1151 |
| send | 22040 | 19916 | 1042 | 1173 |
| strand | plus | plus | plus | plus |
| evalue | 5.5 | 5.5 | 5.5 | 5.5 |
| align_ident | 69.697 | 78.788 | 84.848 | 84.848 |
| align_match | 23 | 26 | 28 | 28 |
| align_gap | 0 | 0 | 0 | 0 |
| xstart | 22020 | 19887 | 1020 | 1151 |
| xend | 22052 | 19919 | 1052 | 1183 |
| qry_align | TCAAGATCAA CCATTCATTT GCCACGCAAA TCG (SEQ ID NO: 26) | TCAAGATCAAC CATTCATTTGC CACGCAAATCG (SEQ ID NO: 26) | TCAAGATCAA CCATTCATTT GCCACGCAAA TCG (SEQ ID NO: 26) | TCAAGATCAA CCATTCATTT GCCACGCAAA TCG (SEQ ID NO: 26) |
| sbj_align | TTAAGATCAA CCATTCATTT GTGAATTACA GGC (SEQ ID NO: 41) | TCATTGGCAAC CATTCATTTGT CACGCAAAACC (SEQ ID NO: 42) | TCAAGATCAA CCTTTCATTT GCCGTGCTAA CCG (SEQ ID NO: 31) | TCAAGATCAA CCTTTCATTT GCCGTGCTAA CCG (SEQ ID NO: 31) |
| align_code | 0/00000000 0000000000 0//0///0/0 /// | 000////0000 0000000000/ 00000000/0/ | 0000000000 00/0000000 000//00/00 /00 | 0000000000 00/0000000 000//00/00 /00 |
| sbjct_title | Zebrafish DNA sequence from clone CH211-117N7 in linkage group 13, complete sequence | Zebrafish DNA sequence from clone DKEY-6A5 in linkage group 4, complete sequence | *L. helveticus* pepD gene for dipeptidase | *Lactobacillus helveticus* hypothetical XylS/AraC-type transcription factor gene, partial cds, and dipeptidase gene, complete cds |

First, each of *Lactobacillus acidophilus* LA1, *Lactobacillus helveticus* ATCC 13866, *Lactobacillus amylovorus* ATCC 33620, *Lactobacillus acidophilus* ATCC 4356 and *Lactobacillus acidophilus* NCFM strains was cultured in MRS medium (Difco, 288110) at 37° C. for 18 hours. Then, a colony was recovered from the culture medium of each strain and genomic DNA was extracted with a QIAamp DNA Mini kit (Qiagen, Germany).

Thermal cycling (PCR) was performed for 30 ng of the extracted DNA. For PCR reaction, 20 μL of a reaction mixture wherein 2.0 mM dNTP (Fermentas, USA), 1.0 unit of a thermostable DNA polymerase (e-Taq polymerase, Solgent), 20 pmol CRISPR F primer (SEQ ID NO: 8), 20 pmol CRISPR R primer (SEQ ID NO: 16), 20 ng of strain DNA and buffer (10 mM Tris-HCl (pH 8.0), 50 mM KCl, 1.5 mM MgCl$_2$, 0.01% gelatin) were completely mixed was prepared.

PCR reaction was performed using Dyad (Bio-Rad) under the condition of 300 seconds at 95° C. followed by DNA denaturation at 95° C. for 30 seconds, annealing at 55° C. for 30 seconds and extension (DNA polymerization) at 72° C. for 90 seconds. This procedure was repeated for 30 cycles (95° C., 30 seconds (denaturation)→55° C., 30 seconds (reassembly)→72° C., 90 seconds (DNA polymerization)), followed by final synthesis at 72° C. for 300 seconds.

The amplified amplification product (PCR product) was electrophoresed on 1.2% agarose gel, and polymorphic DNA bands were detected by staining with Safeview (iN-tRON Biotechnology, Korea) and irradiating UV and then imaged with the Gel-Doc system (Bio-Rad). The result is shown in FIG. 16.

FIG. 16 shows the result of performing PCR for different strains (*Lactobacillus acidophilus* LA1, *Lactobacillus helveticus* ATCC 13866, *Lactobacillus amylovorus* ATCC 33620, *Lactobacillus acidophilus* ATCC 4356 and *Lactobacillus acidophilus* NCFM) using the primer set for discriminating individual *Lactobacillus acidophilus* strains of the present disclosure.

M denotes a DNA size marker (Sizer™ 100 bp DNA marker (Cat. No. 24073), 1 denotes *Lactobacillus helveticus* ATCC 13866, 2 denotes *Lactobacillus amylovorus* ATCC 33620, 3 denotes *Lactobacillus acidophilus* ATCC 4356, 4 denotes *Lactobacillus acidophilus* NCFM strain, and 5 denotes *Lactobacillus acidophilus* LA1 (also referred to as CB_LA1).

As seen from the figure, it was confirmed that the composition for discriminating *Lactobacillus acidophilus* strains including the primers represented by SEQ ID NO: 8 and SEQ ID NO: 16 of the present disclosure produced PCR products (100-1000 bp) specifically only for the *Lactobacillus acidophilus* strains.

In addition, it was confirmed that the composition for discriminating *Lactobacillus acidophilus* strains including the primers represented by SEQ ID NO: 8 and SEQ ID NO: 16 of the present disclosure amplified DNA fragments with a size of about 200 bp for *Lactobacillus acidophilus* LA1.

Because it was found through genome analysis that the spacers 6-17 were lost in the base sequence of the CRISPR region of the *Lactobacillus acidophilus* LA1 strain unlike other strains (of the same species and genus), it was expected that the size of the PCR product (amplified DNA fragment, amplicon) obtained with the composition for discriminating a *Lactobacillus acidophilus* LA1 strain including the primers represented by SEQ ID NOS: 8 and 16 would be 165 bp (150 bp+8 bp primer+7 bp dicer). However, PCR products with a size of about 200 bp were identified. This difference is due to the length of the primers of SEQ ID NO: 8 and SEQ ID NO: 16 was added. Specifically, it can be seen that the size of about 190 bp was measured as the primer set sequence (40 bp) of SEQ ID NOS: 8 and 16 was added to the amplified PCR product (150 bp) for the CRISPR region of the *Lactobacillus acidophilus* LA1 strain.

In addition, when considering the slight difference in gel electrophoresis (high resolution of one base is not achieved in electrophoresis), the detection of a PCR product with a size of 200 bp is included in the scope of the present disclosure because the result is derived from the 165 bp-sized PCR product for the CRISPR region of the amplified *Lactobacillus acidophilus* LA1 strain (150 bp+8 bp primer+7 bp dicer).

Accordingly, although it is desired that the PCR product has a size of precisely 165 bp (150 bp+8 bp primer+7 bp dicer), when considering the various conditions described above (including the regions that can be detected with the marker), a PCR product size of 150-250 bp, specifically 150-200 bp, may be discriminated as the *Lactobacillus acidophilus* LA1 strain.

To demonstrate this, the DNA base sequence was investigated for the PCR product of three *L. acidophilus* strains.

Unlike the LA1 strain, no amplified DNA fragment was observed for *Lactobacillus helveticus* ATCC 13866 or *Lactobacillus amylovorus* ATCC 33620. For the *Lactobacillus acidophilus* ATCC 4356 and *Lactobacillus acidophilus* NCFM strains of the same species, amplified DNA fragments of about 900 bp and 1000 bp were observed.

Accordingly, the primers represented by SEQ ID NO: 8 and SEQ ID NO: 16 according to the present disclosure can detect and discriminate the *Lactobacillus acidophilus* LA1 strain from among various strains since they amplify the sequence of the CRISPR selectively for the LA1 strain among the species *Lactobacillus acidophilus*. In addition, the primers represented by SEQ ID NO: 8 and SEQ ID NO: 16 according to the present disclosure may be used as a composition for clearly discriminating only the *Lactobacillus acidophilus* LA1 strain from among the species *Lactobacillus acidophilus* quickly and accurately because amplicons of different sizes are produced depending on strains.

Test Example 5. PCR Analysis of Composition for Discriminating Individual *Lactobacillus acidophilus* Strains of Example 4 (2)

As in Test Example 4, PCR products were obtained by performing polymerase chain reaction for DNAs isolated from *Lactobacillus acidophilus* LA1, *Lactobacillus acidophilus* ATCC 4356 and *Lactobacillus acidophilus* NCFM using the composition for discriminating individual *Lactobacillus acidophilus* strains according to the present disclosure, which include the primers represented by SEQ ID NO: 8 and SEQ ID NO: 16, and their size was analyzed.

First, each of *Lactobacillus acidophilus* LA1, *Lactobacillus acidophilus* ATCC 4356 and *Lactobacillus acidophilus* NCFM strains was cultured in MRS medium (Difco, 288110) at 37° C. for 18 hours. Then, a colony was recovered from the culture medium of each strain and genomic DNA was extracted with a QIAamp DNA Mini kit (Qiagen, Germany).

Thermal cycling (PCR) was performed for the extracted DNA using a PCR reaction mixture described in Table 10. A reaction mixture wherein the extracted *Lactobacillus acidophilus* LA1 strain DNA and buffer (10 mM Tris-HCl (pH 8.0), 50 mM KCl, 1.5 mM MgCl$_2$, 0.01% gelatin) were completely mixed was prepared.

PCR reaction was performed using Dyad (Bio-Rad) under the condition of 5 minutes at 95° C. followed by DNA denaturation at 95° C. for 30 seconds, annealing at 55° C. for 30 seconds and extension (DNA polymerization) at 72° C. for 90 seconds. This procedure was repeated for 30 cycles (95° C., 30 seconds (denaturation)→55° C., 30 seconds (reassembly)→72° C., 90 seconds (DNA polymerization)), followed by final synthesis at 72° C. for 5 minutes.

TABLE 10

| PCR reaction solution | Contents (μL) |
| --- | --- |
| SP Taq | 0.5 |
| 10x SP Taq buffer | 2.5 |
| dNTPs | 2.0 |
| Tuning Buffer | 5.0 |
| Template (strain DNA) | 1.0 |
| Forward primer (5 μM) CRISPR F primer (SEQ ID NO 8) | 1.0 |
| Reverse primer (5 μM) CRISPR R primer (SEQ ID NO 16) | 1.0 |
| D.W | 12 |

The amplified amplification product (PCR product) was electrophoresed on 1.2% agarose gel, and polymorphic DNA bands were detected by staining with Safeview (iN-tRON Biotechnology, Korea) and irradiating UV and then imaged with the Gel-Doc system (Bio-Rad). The result is shown in FIGS. 17-19.

FIG. 17 shows the result of performing PCR for DNA size markers, FIG. 18 shows the result of performing PCR for different strains (*Lactobacillus acidophilus* LA1, *Lactobacillus acidophilus* ATCC 4356 and *Lactobacillus acidophilus* NCFM) using the primer set for discriminating the *L. acidophilus* strain of the present disclosure and conducting agarose gel electrophoresis, and FIG. 19 shows the result of purifying the PCR amplification product obtained by performing PCR for different strains (*Lactobacillus acidophilus* LA1, *Lactobacillus acidophilus* ATCC 4356 and *Lactobacillus acidophilus* NCFM) using the primer set for discriminating the *L. acidophilus* strain of the present disclosure and then analyzing the same by agarose gel electrophoresis.

The lanes with no mark on both sides denote DNA size markers, 1, 4, 7 and 10 denote the *Lactobacillus acidophilus* ATCC 4356 strain, 2, 5, 8 and 11 denote the *Lactobacillus acidophilus* NCFM strain, and 3, 6, 9 and 12 denote the *Lactobacillus acidophilus* LA1 strain (also referred to as CB_LA1).

The sequence of the amplification products shown in FIGS. 17-19 was analyzed. First, the amplification product for the *Lactobacillus acidophilus* NCFM strain had a size of 898 bp excluding the primers. The amplified sequence is as follows.

[SEQ ID NO 18]
CATCAATAGGATCACCTCCACATACGTGGAGAAAATTAGGCAAATAGCCA

ATTTTTATCATACATTCCGGGATCACCTCCACATACGTGGAGAAAATCGG

CAATTTTTGAAACAAACAACTATGTATATAGGATCACCTCCACATACGTG

GAGAAAATAAATAAGGAAGATATTGCCACCCTCGGTACCCAGGATCACCT

CCACATACGTGGAGAAAATACAAGTTTTGCTCTAACCATGATGTTGTAAA

CAGGATCACCTCCACATACGTGGAGAAAATACGTTAAAGCGGACAATAAG

CTTCAACGTTTTAGGATCACCTCCACATACGTGGAGAAAATCGTGCTTGA

-continued
AATTGCTCTCGGGGTTTCGCCTAAGGATCACCTCCACATACGTGGAGAAA

ATATTTGCTGCGAGTAACTCTGACTTGTTTACCCGGGATCACCTCCACAT

ACGTGGAGAAAATTTTAGCTAAGTTTAAGACCGAAGATGGCCAAAGGGAT

CACCTCCACATACGTGGAGAAAATCGGCAATTTTTGAAACAAACAACTAT

GTATATAGGATCACCTCCACATACGTGGAGAAAATCGGCAATTTTTGAAA

CAAACAACTATGTATATAGGATCACCTCCACATACGTGGAGAAAATACAA

GTTTTGCTCTAACCATGATGTTGTAAACAGGATCACCTCCACATACGTGG

AGAAAATAGCTATCCAAATATTAAATTTGCACTAGTTAAGGGGATCACCT

CCACATACGTGGAGAAAATGAAGAATTTTATCTTCTAGGTGGCTTTTTTG

TGGGATCACCTCCACATACGTGGAGAAAATAGAAATATTTGATTTTGATA

GTGAAAAGAATAGGATCACCTCCACATACGTGGAGAAATTCAGTCC

Because the predicted length of the *Lactobacillus acidophilus* NCFM strain is based on the CRISPR region on the *Lactobacillus acidophilus* NCFM strain and the initially predicted length is based on the dicer sequence adjacent to primers rather than the primers, the actually predicted length is 898 bp when considering the 8 bp sequence between the left primer the adjacent dicer and the 7 bp sequence between the right primer and the adjacent dicer.

1 bp deletion was identified in 890 bp when compared with the genome sequence of *Lactobacillus acidophilus* NCFM, which may be due to the quality deterioration of Sanger sequencing. Accordingly, it was confirmed that amplification was performed as predicted when the composition for discriminating the *Lactobacillus acidophilus* LA1 strain, including the primers represented by SEQ ID NO: 8 and SEQ ID NO: 16 according to the present disclosure, was applied to the *Lactobacillus acidophilus* NCFM strain.

Next, a product with a size of 837 bp excluding the primers was observed for the *Lactobacillus acidophilus* ATCC 4356 strain. The amplified sequence is as follows.

[SEQ ID NO 19]
CATCAATAGGATCACCTCCACATACGTGGAGAAAATTAGGCAAATAGCCA

ATTTTTATCATACATTCCGGGATCACCTCCACATACGTGGAGAAAATCGG

CAATTTTTGAAACAAACAACTATGTATATAGGATCACCTCCACATACGTG

GAGAAAATAAATAAGGAAGATATTGCCACCCTCGGTACCCAGGATCACCT

CCACATACGTGGAGAAAATACGTTAAAGCGGACAATAAGCTTCAACGTTT

TAGGATCACCTCCACATACGTGGAGAAAATCGTGCTTGAAATTGCTCTCG

GGGTTTCGCCTAAGGATCACCTCCACATACGTGGAGAAAATATTTGCTGC

GAGTAACTCTGACTTGTTTACCCGGGATCACCTCCACATACGTGGAGAAA

ATTTTAGCTAAGTTTAAGACCGAAGATGGCCAAAGGGATCACCTCCACAT

ACGTGGAGAAAATCGGCAATTTTTGAAACAAACAACTATGTATATAGGAT

CACCTCCACATACGTGGAGAAAATCGGCAATTTTTGAAACAAACAACTAT

GTATATAGGATCACCTCCACATACGTGGAGAAAATACAAGTTTTGCTCTA

ACCATGATGTTGTAAACAGGATCACCTCCACATACGTGGAGAAAATAGCT

ATCCAAATATTAAATTTGCACTAGTTAAGGGGATCACCTCCACATACGTG

GAGAAAATGAAGAATTTTATCTTCTAGGTGGCTTTTTTGTGGGATCACCT

-continued

CCACATACGTGGAGAAAATAGAAATATTTGATTTTGATAGTGAAAAAGAA

TAGGATCACCTCCACATACGTGGAGAAATTCAGATAC

Because the predicted length of the *Lactobacillus aci-dophilus* ATCC 4356 strain is based on the CRISPR region on the *Lactobacillus acidophilus* NCFM strain and the initially predicted length is based on the dicer sequence adjacent to primers rather than the primers, the actually predicted length is 898 bp when considering the 8 bp sequence between the left primer the adjacent dicer and the 7 bp sequence between the right primer and the adjacent dicer.

However, deletion of the spacer 9 (33 bp) and dicer (28 bp) of *Lactobacillus acidophilus* NCFM was identified for the CRISPR region of *Lactobacillus acidophilus* ATCC 4356. It was expected that the length of the CRISPR region of *Lactobacillus acidophilus* ATCC 4356 would be 837 bp, which is shorter than *Lactobacillus acidophilus* NCFM by 61 bp.

Actually, the sequence length of the amplified *Lactobacillus acidophilus* ATCC 4356 was identified to be 837 bp, 61 bp shorter than the sequence of *Lactobacillus acidophilus* NCFM.

Through this, it was confirmed that the composition for discriminating the *Lactobacillus acidophilus* LA1 strain, including the primers represented by SEQ ID NO: 8 and SEQ ID NO: 16 according to the present disclosure, can accurately distinguish *Lactobacillus acidophilus* NCFM not only from *Lactobacillus acidophilus* ATCC 4356 but also from *Lactobacillus acidophilus* LA1.

Finally, a product with a size of 165 bp excluding the primers was observed for the *Lactobacillus acidophilus* LA1 strain. The amplified sequence is as follows.

[SEQ ID NO 20]

CATCAATAGGATCACCTCCACATACGTGGAGAAAATGAAGAATTTTATCT

TCTAGGTGGCTTTTTTGTGGGATCACCTCCACATACGTGGAGAAAATAGA

AATATTTGATTTTGATAGTGAAAAAGAATAGGATCACCTCCACATACGTG

GAGAAAATTCAAGAT

Because the predicted length of the *Lactobacillus aci-dophilus* LA1 strain is based on the CRISPR region on the *Lactobacillus acidophilus* LA1 strain and the initially predicted length is based on the dicer sequence adjacent to primers rather than the primers, the actually predicted length was 165 bp when considering the 8 bp sequence between the left primer the adjacent dicer and the 7 bp sequence between the right primer and the adjacent dicer.

Actually, the sequence length of the amplified *Lactobacillus acidophilus* LA1 was identified to be 165 bp, matching 100% with the predicted length. That is to say, although the amplified sequence seemed to have a size of about 200 bp as a result of electrophoresis, it actually had a length of 165 bp, matching perfectly with the predicted length.

Through this, it can be seen that the composition for discriminating the *Lactobacillus acidophilus* LA1 strain, which includes the primers represented by SEQ ID NO: 8 and SEQ ID NO: 16 of the present disclosure, can clearly distinguish *Lactobacillus acidophilus* LA1 from the strains belonging to the same species and genus.

Accordingly, since the primers represented by SEQ ID NO: 8 and SEQ ID NO: 16 according to the present disclosure selectively amplifies the sequence of the CRISPR target region only for the strain of the species *Lactobacillus acidophilus*, they can detect and discriminate *Lactobacillus acidophilus* strains from among different strains. In addition, since primers represented by SEQ ID NO: 8 and SEQ ID NO: 16 according to the present disclosure produce amplicons of different sizes for different strains of the species *Lactobacillus acidophilus*, they can be used as a composition for discriminating the *Lactobacillus acidophilus* LA1 strain quickly and accurately.

Test Example 6. PCR Analysis of Composition for Discriminating *Lactobacillus acidophilus* Strains of Example 7

It was investigated whether the composition of the present disclosure for discriminating *Lactobacillus acidophilus* strains shown in FIG. 11 can specifically discriminate *L. acidophilus* strains, especially the *L. acidophilus* YT1 strain.

First, each of *Lactobacillus helveticus* ATCC 13866, *Lactobacillus amylovorus* ATCC 33620, *Lactobacillus acidophilus* ATCC 4356, *Lactobacillus acidophilus* NCFM, *Lactobacillus acidophilus* LA1 and *Lactobacillus acidophilus* YT1 strains was cultured in MRS medium (Difco, 288110) at 37° C. for 18 hours. Then, a colony was recovered from the culture medium of each strain and genomic DNA was extracted with a QIAamp DNA Mini kit (Qiagen, Germany).

Thermal cycling (PCR) was performed for 30 ng of the extracted DNA. For PCR reaction, 20 μL of a reaction mixture wherein 2.0 mM dNTP (Fermentas, USA), 1.0 unit of a thermostable DNA polymerase (e-Taq polymerase, Solgent), 20 pmol CRISPR YT1 F (SEQ ID NO: 7), 20 pmol CRISPR YT1 R primer (SEQ ID NO: 15), 20 ng of strain DNA and buffer (10 mM Tris-HCl (pH 8.0), 50 mM KCl, 1.5 mM MgCl$_2$, 0.01% gelatin) were completely mixed was prepared.

PCR reaction was performed using Dyad (Bio-Rad) under the condition of 300 seconds at 95° C. followed by DNA denaturation at 95° C. for 30 seconds, annealing at 60° C. for 30 seconds and extension (DNA polymerization) at 72° C. for 90 seconds. This procedure was repeated for 28 cycles (95° C., 30 seconds (denaturation)→60° C., 30 seconds (reassembly)→72° C., 90 seconds (DNA polymerization)), followed by final synthesis at 72° C. for 300 seconds.

TABLE 11

| PCR reaction solution | Contents (μL) |
|---|---|
| SP Taq | 0.5 |
| 10x SP Taq buffer | 2.5 |
| dNTPs | 2.0 |
| Tuning Buffer | 5.0 |
| Template (strain DNA) | 1.0 |
| Forward primer (5 μM) | 1.0 |
| CRISPR YT1 F primer (SEQ ID NO 7) | |
| Reverse primer (5 μM) | 1.0 |
| CRISPR YT1 R primer (SEQ ID NO 15) | |
| D.W | 12 |

The amplified amplification product (PCR product) was electrophoresed on 1.2% agarose gel, and polymorphic DNA bands were detected by staining with Safeview (iN-tRON Biotechnology, Korea) and irradiating UV and then imaged with the Gel-Doc system (Bio-Rad). The result is shown in FIG. 20.

FIG. 20 shows the result of performing PCR for different strains (*Lactobacillus helveticus* ATCC 13866, *Lactobacillus amylovorus* ATCC 33620, *Lactobacillus acidophilus*

ATCC 4356, *Lactobacillus acidophilus* NCFM, *Lactobacillus acidophilus* LA1 and *Lactobacillus acidophilus* YT1) using the primer set for discriminating a *Lactobacillus acidophilus* YT1 strain of the present disclosure.

M denotes a DNA size marker (Sizer™ 100 bp DNA marker (Cat. No. 24073), 1 denotes *Lactobacillus helveticus* ATCC 13866, 2 denotes *Lactobacillus amylovorus* ATCC 33620, 3 denotes *Lactobacillus acidophilus* ATCC 4356, 4 denotes *Lactobacillus acidophilus* NCFM strain, 5 denotes *Lactobacillus acidophilus* LA1 (also referred to as CB_LA1), and 6 denotes *Lactobacillus acidophilus* YT1.

It was confirmed that the composition for discriminating *Lactobacillus acidophilus* strains, including the primers represented by SEQ ID NO: 7 and SEQ ID NO: 15 of the present disclosure, amplified a DNA fragment with a size of about 320 bp for *Lactobacillus acidophilus* YT1.

It was confirmed through genome analysis that the *Lactobacillus acidophilus* YT1 strain has two CRISPR regions with different base sequences unlike other strains (of the same species and genus) and only a portion of the CRISPR regions is conserved. Specifically, the spacers 1-5 of NCFM were present in the first CRISPR of YT1, and the spacers 22-26 of NCFM were present in the second CRISPR of YT1. 320 bp from the 6th nucleotide of spacer 5 to the 20th nucleotide of spacer d was the target of amplification. The PCR product obtained using the composition for discriminating the *Lactobacillus acidophilus* YT1 strain, including the primers represented by SEQ ID NOS: 7 and 15, had a size of 320 bp.

When considering the slight difference in gel electrophoresis (high resolution of one base is not achieved in electrophoresis), the detection of a PCR product with a size of 320 bp is included in the scope of the present disclosure because the result is derived from the 320 bp-sized PCR product for the CRISPR region of the amplified *Lactobacillus acidophilus* YT1 strain.

Accordingly, although it is desired that the PCR product has a size of precisely 320 bp, when considering the various conditions described above, a PCR product size of 250-400 bp, specifically 300-350 bp, may be discriminated as the *Lactobacillus acidophilus* YT1 strain.

To demonstrate this, the DNA base sequence was investigated for the PCR product of the *L. acidophilus* YT1 strain.

Unlike the YT1 strain, no amplified DNA fragment was observed for *Lactobacillus helveticus* ATCC 13866, *Lactobacillus amylovorus* ATCC 33620, *Lactobacillus acidophilus* ATCC 4356, *Lactobacillus acidophilus* NCFM and *Lactobacillus acidophilus* LA1.

Accordingly, the primers represented by SEQ ID NO: 7 and SEQ ID NO: 15 according to the present disclosure can be used as a composition for discriminating the *Lactobacillus acidophilus* YT1 strain quickly and accurately, because it produces amplicons only for *Lactobacillus acidophilus* YT1.

The PCR amplification product of the YT1 strain was purified and sequenced. FIG. 21 shows the result of purifying the PCR amplification product obtained by performing PCR for the *Lactobacillus acidophilus* YT1 strain using the primer set for discriminating a *Lactobacillus acidophilus* YT1 strain of the present disclosure and analyzing the same by agarose gel electrophoresis. A representative result of 10 repeated experiments is shown.

In FIG. 21, M denotes a Sizer™ 100 bp DNA marker (Cat. No. 24073), N denotes blank, and YT1-a and YT1-b denote the experimental results for *Lactobacillus acidophilus* YT1.

As shown in FIG. 21, it was confirmed that a consistent result was obtained with the composition for discriminating the *Lactobacillus acidophilus* YT1 strain of the present disclosure for repeated experiments. It was also confirmed that the *Lactobacillus acidophilus* YT1 strain can be discriminated quickly, conveniently, accurately and reproducibly.

As a result of analyzing the sequence of the amplification product shown in FIG. 21, the size of the amplification product of the *Lactobacillus acidophilus* YT1 strain was identified to be 320 bp including the primers for the two experiments. The amplified sequence is as follows.

```
                                     [SEQ ID NO 21]
TTGACTTGCGCTAGGTGTTGCATCAATAGGATCACCTCCACATACGTGGA

GAAAATGACACCAAAAAGGGCGGTGGAAAACTTTTCAAAGGATCACCTCC

ACATACGTGGAGAAAATGACACCAAAAAGGGCGGTGGAAAACTTTTCAAA

GGATCACCTCCACATACGTGGAGAAAATACTTCAACTAATCCTAATTATC

CTGGCAATCCAGGATCACCTCCACATACGTGGAGAAAATGCCTAGTGCCT

TACCAGCCTCGGCAAAACTGTGGGATCACCTCCACATACGTGGAGAAAAT

GGAACAACGCTTTCTGGTGA
```

Actually, the sequence length of the amplified *Lactobacillus acidophilus* YT1 was identified to be 320 bp, matching 100% with the predicted length. That is to say, although the amplified sequence seemed to have a size of about 300 bp as a result of electrophoresis, it actually had a length of 320 bp, matching perfectly with the predicted length.

Through this, it can be seen that the composition for discriminating the *Lactobacillus acidophilus* YT1 strain, which includes the primers represented by SEQ ID NO: 7 and SEQ ID NO: 15 of the present disclosure, can clearly distinguish *Lactobacillus acidophilus* YT1 from the strains belonging to the same species and genus.

Accordingly, since the primers represented by SEQ ID NO: 7 and SEQ ID NO: 15 according to the present disclosure produces amplicons only for *Lactobacillus acidophilus* YT1, they can be used as a composition for discriminating the *Lactobacillus acidophilus* YT1 strain quickly and accurately.

---

We claim:

1. A method for identifying presence of *Lactobacillus acidophilus* strains *Lactobacillus acidophilus* LA1, *Lactobacillus acidophilus* YT1, *Lactobacillus acidophilus* ATCC 4356, or *Lactobacillus acidophilus* NCFM in a target sample comprising a mixture of *Lactobacillus acidophilus* strains, comprising:

a) using a primer composition to obtain a PCR product through polymerase chain reaction (PCR) by using a template comprising DNA isolated from the target sample to be discriminated;

wherein the primer set comprises:

i) a primer set consisting of a forward primer having the sequence of SEQ ID NO: 7 and a reverse primer having the sequence of SEQ ID NO: 16; and/or ii) a primer set consisting of a forward primer having the sequence of SEQ ID NO: 7 and a reverse primer having the sequence of SEQ ID NO: 15;

wherein the forward primer further comprises one or more labels selected from the group consisting of a fluorophore, a chromophore, a chemiluminophore, a magnetic particle and a radioisotope, wherein the one or more labels is linked to the 5'-end of the forward primer;

and b) identifying the presence of *Lactobacillus acidophilus* LA1, *Lactobacillus acidophilus* YT 1, *Lactobacillus acidophilus* ATCC 4356, or *Lactobacillus acidophilus* NCFM from the PCR product;

wherein identifying the presence of *Lactobacillus acidophilus* LA1, *Lactobacillus acidophilus* YT1, *Lactobacillus acidophilus* ATCC 4356, or *Lactobacillus acidophilus* NCFM comprises determining a size of the PCR product;

wherein the size of the PCR product obtained in step a) corresponds to the presence of *Lactobacillus acidophilus* LA1, *Lactobacillus acidophilus* YT1, *Lactobacillus acidophilus* ATCC 4356, or *Lactobacillus acidophilus* NCFM;

wherein if the size of the PCR product is 150-200 bp, then the *Lactobacillus acidophilus* strain that is present is *Lactobacillus acidophilus* LA1;

wherein if the size of the PCR product is 300-350 bp, then the *Lactobacillus acidophilus* strain that is present is *Lactobacillus acidophilus* YT1;

wherein if the size of the PCR product is 800-1000 bp, then the *Lactobacillus acidophilus* strain that is present is *Lactobacillus acidophilus* ATCC 4356 or *Lactobacillus acidophilus* NCFM.

2. The method according to claim 1, wherein the primer set consists of the forward primer having the sequence of SEQ ID NO: 7 and the reverse primer having the sequence of SEQ ID NO: 15.

3. The method of claim 1, wherein the forward primer further comprises the chromophore linked to the 5'-end of the forward primer.

4. The method of claim 1, wherein the forward primer further comprises the chemiluminophore linked to the 5'-end of the forward primer.

5. The method of claim 1, wherein the forward primer further comprises the magnetic particle linked to the 5'-end of the forward primer.

6. The method of claim 1, wherein the forward primer further comprises the radioactive isotope linked to the 5'-end of the forward primer.

7. The method of claim 1, wherein the PCR product has a size of 165 bp and the *Lactobacillus acidophilus* strain is *Lactobacillus acidophilus* LA1.

8. The method of claim 1, wherein the PCR product has a size of 320 bp and the *Lactobacillus acidophilus* strain is *Lactobacillus acidophilus* YT1.

9. The method of claim 1, wherein the PCR product has a size of 837 bp and the *Lactobacillus acidophilus* strain is *Lactobacillus acidophilus* ATCC 4356.

10. The method of claim 1, wherein the PCR product has a size of 898 bp and the *Lactobacillus acidophilus* strain is *Lactobacillus acidophilus* NCFM.

* * * * *